United States Patent
Fischer-Lougheed et al.

(10) Patent No.: US 11,992,524 B2
(45) Date of Patent: May 28, 2024

(54) COMPOSITIONS AND METHODS FOR THERAPEUTIC OR VACCINE DELIVERY

(71) Applicant: GenVivo, Inc., San Marino, CA (US)

(72) Inventors: Jacqueline Fischer-Lougheed, Duarte, CA (US); Bradford H. Steele, Pasadena, CA (US); Cecilia Roh, South Pasadena, CA (US); Robert G. Johnson, Lafayette, CA (US)

(73) Assignee: Genvivo, Inc., San Marino, CA (US)

( * ) Notice: Subject to any disclaimer, the term of this patent is extended or adjusted under 35 U.S.C. 154(b) by 0 days.

(21) Appl. No.: 18/049,267

(22) Filed: Oct. 24, 2022

(65) Prior Publication Data

US 2023/0277647 A1   Sep. 7, 2023

Related U.S. Application Data

(60) Provisional application No. 63/413,188, filed on Oct. 4, 2022, provisional application No. 63/271,675, filed on Oct. 25, 2021.

(51) Int. Cl.
| | |
|---|---|
| *A61K 39/12* | (2006.01) |
| *A61K 39/145* | (2006.01) |
| *A61P 31/14* | (2006.01) |
| *A61K 39/00* | (2006.01) |

(52) U.S. Cl.
CPC ............ *A61K 39/12* (2013.01); *A61K 39/145* (2013.01); *A61P 31/14* (2018.01); *A61K 2039/5256* (2013.01); *A61K 2039/575* (2013.01)

(58) Field of Classification Search
None
See application file for complete search history.

(56) References Cited

U.S. PATENT DOCUMENTS

| | | | | |
|---|---|---|---|---|
| 2006/0127981 A1* | 6/2006 | Bergman | ............ | C07K 14/005 435/5 |
| 2006/0281128 A1 | 12/2006 | Lu et al. | | |
| 2016/0230190 A1 | 8/2016 | Serguera et al. | | |

FOREIGN PATENT DOCUMENTS

| | | |
|---|---|---|
| WO | WO-2015078999 A1 | 6/2015 |
| WO | WO-2021062419 A1 | 4/2021 |
| WO | WO-2023076180 A2 | 5/2023 |

OTHER PUBLICATIONS

Schambach et al., Human Gene Therapy, 2013, 24(2):132-142. (Year: 2013).*
Genbank, Accession No. AAB07105.1, E2 structural protein of Sindbis virus (Sep. 1996). (Year: 1996).*
Aiyer et al.: Structural and sequencing analysis of local target DNA recognition by MLV integrase. Nucleic Acids Res. 43(11):5647-5663 (2015).
Freyn et al.: A Multi-Targeting, Nucleoside-Modified mRNA Influenza Virus Vaccine Provides Broad Protection in Mice. Mol Ther. 28(7):1569-1584 doi:10.1016/j.ymthe.2020.04.018 (2020).
Gardner et al.: Infection of human dendritic cells by a sindbis virus replicon vector is determined by a single amino acid substitution in the E2 glycoprotein. J Virol. 74(24):11849-11857 doi:10.1128/jvi.74.24.11849-11857 (2000).
Heinz et al.: Distinguishing features of current COVID-19 vaccines: knowns and unknowns of antigen presentation and modes of action. NPJ Vaccines 6(1):104:1-13 doi:10.1038/s41541-021-00369-6 (2021).
Hsieh et al.: Structure-based design of prefusion-stabilized SARS-COV-2 spikes. Science 369(6510):1501-1505 doi:10.1126/science.abd0826 (2020).
Impagliazzo et al.: A stable trimeric influenza hemagglutinin stem as a broadly protective immunogen. Science 49(6254):1301-1306 doi:10.1126/science.aac7263 (2015).
Lai et al.: Moloney murine leukemia virus integrase protein augments viral DNA synthesis in infected cells. J Virol. 75(23):11365-11372 doi:10.1128/JVI.75.23.11365-11372.2001 (2001).
Lesbats et al.: Retroviral DNA Integration. Chem Rev. 116(20):12730-12757 (2015).
Maetzig et al.: Gammaretroviral vectors: biology, technology and application. Viruses 3(6):677-713 doi:10.3390/v3060677 (2011).
Martinez-Flores et al.: SARS-COV-2 Vaccines Based on the Spike Glycoprotein and Implications of New Viral Variants. Front Immunol. 12:701501:1-21 doi:10.3389/fimmu.2021.701501 (2021).
Pallesen, J. et al., Immunogenicity and structures of a rationally designed prefusion MERS-CoV spike antigen. Proceedings of the National Academy of Sciences 114, E7348-E7357 (2017).
PCT/US2022/047599 Invitation to Pay Additional Fees dated Apr. 3, 2023.
Ponce-De-Leon et al.: Safety and immunogenicity of a live recombinant Newcastle disease virus-based COVID-19 vaccine (Patria) administered via the intramuscular or intranasal route: Interim results of a non-randomized open label phase I trial in Mexico. medRxiv, pp. 1-28 doi:10.1101/2022.02.08.22270676 Preprint (2022).
Sengupta et al.: An Optimized Protocol for Packaging Pseudotyped Integrase Defective Lentivirus. Biol Proced Online 18:14 doi:10.1186/s12575-016-0044-z [1-9] (2016).

(Continued)

*Primary Examiner* — Stacy B Chen
(74) *Attorney, Agent, or Firm* — Wilson Sonsini Goodrich & Rosati

(57) ABSTRACT

Described herein are compositions for delivering a therapeutic or vaccine. Also described herein are methods for using the compositions described herein for delivering a therapeutic or a vaccine.

19 Claims, 24 Drawing Sheets

Specification includes a Sequence Listing.

(56) References Cited

OTHER PUBLICATIONS

Zhang et al.: A second functional furin site in the SARS-COV-2 spike protein. Emerg Microbes Infect. 11(1):182-194 doi:10.1080/22221751.2021.2014284 (2022).
Arora et al.: The HIV-1 Integrase: Modeling and Beyond. An Integrated View of the Molecular Recognition and Toxinology—From Analytical Procedures to Biomedical Applications. InTech, 377-403. doi:10.5772/52344.DOI:10.5772/52344 (2013).
PCT/US2022/047599 International Search Report and Written Opinion dated Jun. 27, 2023.

\* cited by examiner

Catalytic Core Domain

Fig. 2

Sanger Sequencing of mutant vector aligned with WT MLV Integrase

1 = wild-type GP340VKS      SEQ ID NO: 25
2 = sequencing with primer 1   SEQ ID NO: 26
3 = sequencing with primer 2   SEQ ID NO: 26

No visible difference with wtGP and mutant GP (mutGP) restriction enzyme mapping, as expected.

Fig. 3

Sequencing of integrase mutants D125A and E220A (expended in bacteria)
D125A correct in bacteria colonies 1,3,4; E220A mutation correct in col 3,4,5.

Sequence identifiers

Top

| | |
|---|---|
| WT | SEQ ID NO: 27 |
| D125A Col1 | SEQ ID NO: 28 |
| D125A Col2 | SEQ ID NO: 29 |
| D125A Col3 | SEQ ID NO: 28 |
| D125A Col4 | SEQ ID NO: 28 |
| D125A col5 | SEQ ID NO: 30 |

Bottom

| | |
|---|---|
| WT | SEQ ID NO:31 |
| E220A Col1 | SEQ ID NO:32 |
| E220A Col3 | SEQ ID NO:33 |
| E220A Col4 | SEQ ID NO:33 |
| E220A Col5 | SEQ ID NO:33 |

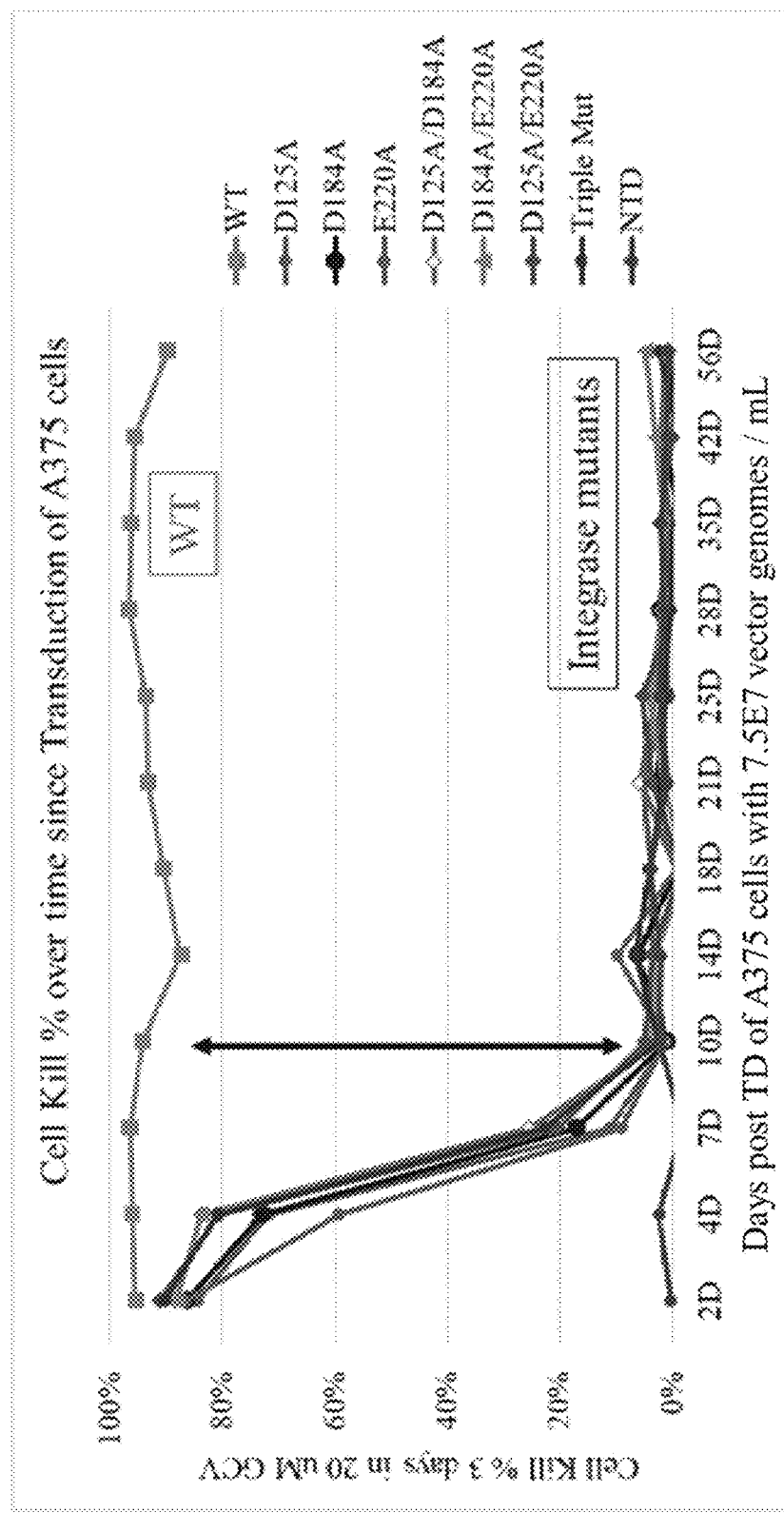

Cell Kill of GEN2 (3 days in GCV)

Cell Kill of Integrase-Deficient GEN2 (3 days in GCV)

Cancer Cell Line Integration by qPCR

Fig. 16A IDRV1/Spike  WT-GP/Spike

Fig. 16B IDRV1/NTD-S2  WT-GP/NTD-S2

Fig. 16C IDRV2/NTD-S2  IDRV2/Spike

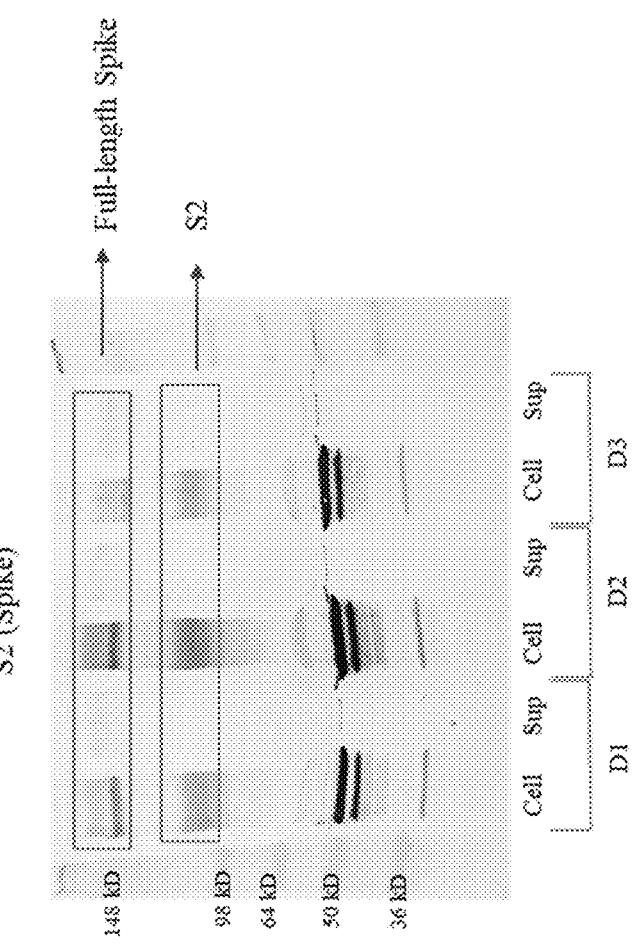

pCL-M2e-HA4900

COMPOSITIONS AND METHODS FOR THERAPEUTIC OR VACCINE DELIVERY

CROSS-REFERENCE

This application claims the benefit of U.S. Provisional Application Ser. No. 63/271,675 filed on Oct. 25, 2021, and U.S. Provisional Application Ser. No. 63/413,188 filed on Oct. 4, 2022, the entirety of which is hereby incorporated by reference herein.

SEQUENCE LISTING

The instant application contains a Sequence Listing which has been submitted electronically in XML format and is hereby incorporated by reference in its entirety. Said XML copy, created on Apr. 20, 2023, is named 30863-731_201_SL.xml and is 29,573 bytes in size.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BACKGROUND

The use of genetic material such as viral vectors for delivering therapeutics has emerged as one of the foundations of modern medicine. However, such genetic material can lead to undesired mitogenic effects. For example, retroviral vectors may integrate into genomes of cells, thus transforming such cells into cancer cells. One remedy for such problem is to use RNA-based vehicle for delivering genetic material.

SUMMARY

The use of RNA-based vehicle can be complex and laborious. Additionally, RNA-based vehicles are prone to degradation and may exhibit a short half-life. Other DNA-based vehicles (e.g., non-viral DNA) for delivering therapeutics face challenges including efficiency of transporting and targeting the vehicle to target cells and induction of immune response or toxicity in the subject. Accordingly, there remains a need for a vehicle for delivering therapeutics.

Described herein, in some aspects, is a recombinant retroviral vector comprising a first nucleic acid sequence encoding a mutant integrase and a second nucleic acid sequence encoding at least one payload, said mutant integrase, when compared to a wild-type integrase, comprises at least one mutation in a $Mg^{2+}$ binding motif of a catalytic core domain; and said at least one payload comprises an antigen. In some embodiments, the mutant integrase is defective in retroviral integration activity. In some embodiments, the antigen comprises a pathogen polypeptide or fragment thereof or a cancer polypeptide or fragment thereof. In some embodiments, the cancer polypeptide or fragment thereof is associated with a cancer cell or a tumor microenvironment. In some embodiments, the pathogen polypeptide or fragment thereof comprises a virus polypeptide or fragment thereof. In some embodiments, the pathogen polypeptide or fragment thereof comprises a bacterium polypeptide or fragment thereof. In some embodiments, the pathogen polypeptide or fragment thereof comprises a fungus polypeptide or fragment thereof. In some embodiments, the pathogen polypeptide or fragment thereof comprises a protist polypeptide or fragment thereof. In some embodiments, the pathogen polypeptide or fragment thereof comprises a protozoa polypeptide or fragment thereof. In some embodiments, the viral polypeptide or fragment thereof comprises a coronavirus polypeptide or fragment thereof. In some embodiments, the coronavirus polypeptide or fragment thereof comprises a Severe Acute Respiratory Syndrome (SARS-CoV) polypeptide or fragment thereof, a SARS-CoV-2 polypeptide or fragment thereof, or a Middle East Respiratory Syndrome (MERS-CoV) polypeptide or fragment thereof. In some embodiments, the coronavirus polypeptide or fragment thereof comprises the SARS-CoV-2 polypeptide or fragment thereof. In some embodiments, the SARS-Cov-2 polypeptide or fragment thereof comprises a Spike protein or fragment thereof. In some embodiments, the Spike protein or fragment thereof is a full-length Spike protein. In some embodiments, the Spike protein or fragment thereof is a truncated Spike protein. In some embodiments, the truncated Spike protein comprises N-terminal domain of the Spike protein or S2 domain of the Spike protein. In some embodiments, the truncated Spike protein comprises N-terminal domain of the Spike protein and S2 domain of the Spike protein. In some embodiments, the Spike protein or fragment thereof is a recombinant Spike protein. In some embodiments, the Spike protein or fragment thereof comprises at least one modification. In some embodiments, the at least one modification comprises codon optimization. In some embodiments, the codon optimization optimizes or increases expression of the at least one payload in a human cell. In some embodiments, the at least one modification comprises at least one amino acid mutation. In some embodiments, the at least one amino acid mutation eliminates a cleavage site in the Spike protein. In some embodiments, the cleavage site is a furin cleavage site. In some embodiments, the furin cleavage site comprises amino acid residues 682-685, amino acid residues 679-682, or amino acid residue 811 in SEQ ID NO: 21 or SEQ ID NO: 22. In some embodiments, the cleavage site is a serine protease cleavage site. In some embodiments, the serine protease cleavage site comprises amino acid residues 986 and 987; or 983 and 984 in SEQ ID NO: 21 or SEQ ID NO: 22. In some embodiments, the at least one amino acid mutation comprises amino acid substitution at amino acid residue 814, 889, 896, 939, 682-685, 679-682, 811, 986, 987, 983, 984, or a combination thereof in SEQ ID NO: 21 or SEQ ID NO: 22. In some embodiments, the at least one amino acid mutation comprises amino acid substitution at amino acid residue 814, 889, 896, and 939 in SEQ ID NO: 21 or SEQ ID NO: 22. In some embodiments, the Spike protein or fragment thereof comprises a signal peptide. In some embodiments, the signal peptide is a secretory peptide. In some embodiments, the signal peptide comprises an amino acid sequence of SEQ ID NO: 13: MDAMKRGLCCVLLLCGAVFVSASQEIHARFRR. In some embodiments, the secretory peptide comprises an amino acid sequence that is at least 70% identical to IgE Fc receptor alpha. In some embodiments, the viral polypeptide or fragment thereof comprises an influenza polypeptide or fragment thereof. In some embodiments, the influenza polypeptide or fragment thereof comprises an influenza A polypeptide or fragment thereof, an influenza B polypeptide or fragment thereof, an influenza C polypeptide or fragment thereof, or an influenza D polypeptide or fragment thereof. In some embodiments, the influenza polypeptide or fragment thereof is the influenza A polypeptide or fragment thereof. In some embodiments, the influenza A polypeptide or fragment thereof comprises neuraminidase (NA) or fragment thereof or hemagglutinin (HA) or fragment thereof. In some embodiments, the influenza A polypeptide or fragment thereof comprises the hemagglutinin (HA) or fragment thereof. In some embodiments, the hemagglutinin (HA) or fragment thereof is a full-length hemagglutinin (HA). In some embodiments, the hemagglutinin (HA) or fragment thereof is a truncated hemagglutinin (HA). In some embodiments, the truncated hemagglutinin (HA) comprises Stalk domain. In some embodiments, the hemagglutinin (HA) or fragment thereof is a recombinant hemagglutinin (HA). In some embodiments, the hemagglutinin (HA) or fragment thereof comprises at least one modification. In some embodiments, the at least one modification comprises codon optimization. In some embodiments, the codon optimization optimizes or increases expression of the at least one payload in a human cell. In some embodiments, the at least one modification comprises at least one amino acid mutation. In some embodiments, the at least one modification comprises the hemagglutinin (HA) or fragment thereof comprising an amino acid sequence of extracellular domain of M2 protein (M2e) of influenza A: SEQ ID NO: 14: MSLLTEVET-PIRNEWGCRCNDSSD. In some embodiments, the recombinant retroviral vector encodes at least one envelope protein. In some embodiments, the at least one envelope protein comprises at least one alphavirus envelope protein. In some embodiments, the at least one alphavirus envelope protein comprises at least one Sindbis virus envelope protein. In some embodiments, the at least one Sindbis virus envelope protein comprises E3 protein, E2 protein, 6K protein, E1 protein, or a combination thereof. In some embodiments, the at least one Sindbis virus envelope protein comprises at least one mutation. In some embodiments, the at least one mutation increases binding affinity between the at least one Sindbis virus envelope protein and a human cell. In some embodiments, the human cell is a dendritic cell. In some embodiments, the at least one mutation is E160G of the E2 protein. In some embodiments, at least one mutation in the Mg2+ binding motif of the catalytic core domain comprises D125A, D184A, or a combination thereof. In some embodiments, the recombinant retroviral vector comprises at least one modified untranslated region (UTR). In some embodiments, the at least one modified UTR comprises a 5'-UTR. In some embodiments, the at least one modified UTR comprises a 3'-UTR. In some embodiments, the at least one modified UTR comprises a 5'-UTR and a 3'-UTR.

Described herein, in some aspects, is a recombinant virus comprising a recombinant retroviral vector described herein. In some embodiments, the recombinant virus is a recombinant Sindbis virus. In some embodiments, the recombinant Sindbis virus comprises E160G mutation of the E2 protein.

Described herein, in some aspects, is a cell comprising a recombinant retroviral vector described herein or a recombinant virus of described herein. In some embodiments, the cell expresses the at least one payload. In some embodiments, the cell secretes the at least one payload. In some embodiments, the cell expresses and secretes the at least one payload. In some embodiments, the cell expresses the at least one payload for at least one day, at least three days, at least five days, or at least nine days. In some embodiments, the cell secretes the at least one payload for at least one day, at least three days, at least five days, or at least nine days. In some embodiments, the cell expresses and secretes the at least one payload for at least one day, at least three days, at least five days, or at least nine days.

Described herein, in some aspects, is a pharmaceutical composition comprising a recombinant retroviral vector described herein, a recombinant virus described herein, or a cell comprising a recombinant retroviral vector described herein or a recombinant virus described herein. In some embodiments, the pharmaceutical composition comprises at least one additional active ingredient. In some embodiments, the at least one additional active ingredient comprises an adjuvant. In some embodiments, the pharmaceutical composition comprises at least one pharmaceutically acceptable excipient.

Described herein, in some aspects, is a method of treating or preventing a disease or condition in a subject, comprising administering to the subject a recombinant retroviral vector described herein, a recombinant virus described herein, a cell comprising a recombinant retroviral vector described herein or a recombinant virus described herein, or a pharmaceutical composition described herein, wherein the at least one payload comprising the antigen induces immune response in the subject, thereby treating or preventing the disease or condition in the subject. In some embodiments, the immune response comprises induction of neutralizing antibody targeting the antigen, thereby generating immunity against the antigen in the subject. In some embodiments, the immune response comprises induction of immunoglobulin antibody targeting the antigen, thereby generating immunity against the antigen in the subject. In some embodiments, the immunoglobulin antibody comprises IgG antibody, IgM antibody, IgA antibody, IgD antibody, IgE antibody, or a combination thereof. In some embodiments, the immunoglobulin antibody comprises IgG antibody. In some embodiments, the at least one payload is expressed in the subject for at least one day, at least three days, at least five days, or at least nine days. In some embodiments, the at least one payload is secreted in the subject for at least one day, at least three days, at least five days, or at least nine days. In some embodiments, a duration of the immune response induced by the at least one payload is expressed for at least one day, at least three days, at least five days, or at least nine days is increased by at least 10%, at least 20%, at least 50%, at least 100%, at least 5-fold, at least 10-fold, or more compared to a duration of an immune response induced by a comparable payload that is expressed for fewer than one day, three days, five days, or nine days. In some embodiments, a duration of the immune response induced by the at least one payload is secreted for at least one day, at least three days, at least five days, or at least nine days is increased by at least 10%, at least 20%, at least 50%, at least 100%, at least 5-fold, at least 10-fold, or more compared to a duration of an immune response induced by a comparable payload that is expressed for fewer than one day, three days, five days, or nine days. In some embodiments, the immune response persists in the subject for at least three months, at least four months, at least five months, at least six months, at least 12 months, or longer Described herein, in some aspects, is a recombinant retroviral vector comprising a nucleic acid construct comprising a polynucleotide sequence encoding a mutant integrase, wherein the mutant integrase, compared with a wild-type integrase, comprises a first mutation in $Mg^{2+}$ binding motif of catalytic core domain. In some embodiments, the first mutation comprises changing an aspartic acid (D) or a glutamic acid (E) to an amino acid having a hydrophobic side chain. In some embodiments, the amino acid is selected from the group consisting of a valine (V), an alanine (A), a leucine (L), an isoleucine (I), and a phenylalanine (F). In some embodiments, the amino acid comprises the phenylalanine (F). In some embodiments, the amino acid comprises the alanine (A). In some embodiments, the first mutation comprises changing an aspartic acid (D) or a glutamic acid (E) to an amino acid having a positive charge side chain. In some embodiments, the amino acid comprises a histidine (H). In some embodiments, the first mutation comprises changing an aspartic acid (D) or a glutamic acid (E) to an amino acid having a polar side chain. In some embodiments, the amino acid comprises a serine (S). In some embodiments, the first mutation comprises changing an aspartic acid (D) or a glutamic acid (E) to a cysteine (C). In some embodiments, the first mutation comprises a D125A mutation. In some embodiments, the first mutation comprises a D184A mutation. In some embodiments, the first mutation comprises a E220A mutation. In some embodiments, the mutant integrase further comprises a second mutation in the $Mg^{2+}$ binding motif of the catalytic core domain. In some embodiments, the second mutation comprises changing an aspartic acid (D) or a glutamic acid (E) to an amino acid having a hydrophobic side chain. In some embodiments, the second mutation comprises an amino acid selected from the group consisting of a valine (V), an alanine (A), a leucine (L), an isoleucine (I), and a phenylalanine (F). In some embodiments, the second mutation comprises the phenylalanine (F). In some embodiments, the second mutation comprises the alanine (A). In some embodiments, the second mutation comprises changing an aspartic acid (D) or a glutamic acid (E) to an amino acid having a positive charge side chain. In some embodiments, the second mutation comprises a histidine (H). In some embodiments, the second mutation comprises changing an aspartic acid (D) or a glutamic acid (E) to an amino acid having a polar charge side chain. In some embodiments, the second mutation comprises a serine (S). In some embodiments, the second mutation comprises changing an aspartic acid (D) or a glutamic acid (E) to a cysteine (C). In some embodiments, the first mutation comprises a D125A mutation and the second mutation comprises a D184A mutation. In some embodiments, the first mutation comprises a D184A mutation and the second mutation comprises a E220A mutation. In some embodiments, the first mutation comprises a D125A mutation and the second mutation comprises a E220A mutation. In some embodiments, the mutant integrase further comprises a third mutation in the $Mg^{2+}$ binding motif of the catalytic core domain. In some embodiments, the third mutation comprises changing an aspartic acid (D) or a glutamic acid (E) to an amino acid having a hydrophobic side chain. In some embodiments, the third mutation comprises an amino acid selected from the group consisting of a valine (V), an alanine (A), a leucine (L), an isoleucine (I), and a phenylalanine (F). In some embodiments, the third mutation comprises the phenylalanine (F). In some embodiments, the third mutation comprises the alanine (A). In some embodiments, the third mutation comprises changing an aspartic acid (D) or a glutamic acid (E) to an amino acid having a positive charge side chain. In some embodiments, the third mutation comprises a histidine (H). In some embodiments, the third mutation comprises changing an aspartic acid (D) or a glutamic acid (E) to an amino acid having a polar charge side chain. In some embodiments, the third mutation comprises a serine (S). In some embodiments, the third mutation comprises changing an aspartic acid (D) or a glutamic acid (E) to a cysteine (C). In some embodiments, the first and second mutations each comprises changing an aspartic acid (D) to an amino acid having a hydrophobic side chain, and the third mutation comprises changing a glutamic acid (E) to an amino acid having a hydrophobic side chain. In some embodiments, the recombinant retroviral vector is murine leukemia virus (MLV), wherein the first mutation is selected from the group consisting of D125A, D184A, and E220A. In some embodiments, the mutant integrase further comprises a second mutation in the $Mg^{2+}$ binding motif of the catalytic core domain, wherein the second mutation is selected from the group consisting of D125A, D184A, and E220A. In some embodiments, the mutant integrase further comprises a third mutation in the $Mg^{2+}$ binding motif of the catalytic core domain, wherein the first mutation comprises D125A, the second mutation comprises E220A, and the third mutation comprises D184A. In some embodiments, the mutant integrase further comprises a third mutation in the Mg2+ binding motif of the catalytic core domain, wherein the first mutation comprises D125A and the second mutation comprises D184A.

Described herein, in some aspects, is a recombinant retroviral vector comprising a nucleic acid construct comprising a polynucleotide sequence encoding a mutant integrase, wherein the mutant integrase, compared with a wild-type integrase, consists of a single mutation in the $Mg^{2+}$ binding motif of the catalytic core domain. In some embodiments, the single mutation consists of changing an aspartic acid (D) or a glutamic acid (E) to an amino acid having a hydrophobic side chain. In some embodiments, the single mutation comprises an amino acid selected from the group consisting of a valine (V), an alanine (A), a leucine (L), an isoleucine (I), and a phenylalanine (F). In some embodiments, the single mutation comprises the phenylalanine (F). In some embodiments, the single mutation comprises the alanine (A). In some embodiments, the single mutation comprises changing an aspartic acid (D) or a glutamic acid (E) to an amino acid having a positive charge side chain. In some embodiments, the single mutation comprises a histidine (H). In some embodiments, the single mutation comprises changing an aspartic acid (D) or a glutamic acid (E) to an amino acid having a polar charge side chain. In some embodiments, the single mutation comprises a serine (S). In some embodiments, the single mutation comprises changing an aspartic acid (D) or a glutamic acid (E) to a cysteine (C). In some embodiments, the mutant integrase comprises a peptide sequence that is at least 80%, at least 85%, at least 90%, at least 95%, at least 99%, or more identical to SEQ ID NO: 1. In some embodiments, the single mutation comprises a D125A mutation. In some embodiments, the mutant integrase comprises a peptide sequence that is at least 80%, at least 85%, at least 90%, at least 95%, at least 99%, or more identical to SEQ ID NO: 2. In some embodiments, the single mutation comprises a D184A mutation. In some embodiments, the mutant integrase comprises a peptide sequence that is at least 80%, at least 85%, at least 90%, at least 95%, at least 99%, or more identical to SEQ ID NO: 3. In some embodiments, the single mutation comprises a E220A mutation. In some embodiments, the mutant integrase comprises a peptide sequence that is at least 80%, at least 85%, at least 90%, at least 95%, at least 99%, or more identical to SEQ ID NO: 4.

Described herein, in some aspects, is a recombinant retroviral vector comprising a nucleic acid construct comprising a polynucleotide sequence encoding a mutant integrase, wherein the mutant integrase, compared with a wild-type integrase, consists of two mutations in the $Mg^{2+}$ binding motif of the catalytic core domain. In some embodiments, at least one of two mutations consists of changing an aspartic acid (D) or a glutamic acid (E) to an amino acid having a hydrophobic side chain. In some embodiments, the at least one of two mutations comprises an amino acid selected from the group consisting of a valine (V), an alanine (A), a leucine (L), an isoleucine (I), and a phenylalanine (F). In some embodiments, the at least one of two mutations comprises the phenylalanine (F). In some embodiments, the at least one of two mutations comprises the alanine (A). In some embodiments, at least one of two mutations comprises changing an aspartic acid (D) or a glutamic acid (E) to an amino acid having a positive charge side chain. In some embodiments, the at least one of two mutations comprises a histidine (H). In some embodiments, the at least one of two mutations comprises changing an aspartic acid (D) or a glutamic acid (E) to an amino acid having a polar charge side chain. In some embodiments, the at least one of two mutations comprises a serine (S). In some embodiments, the at least one of two mutations comprises changing an aspartic acid (D) or a glutamic acid (E) to a cysteine (C). In some embodiments, the mutant integrase comprises a peptide sequence that is at least 80%, at least 85%, at least 90%, at least 95%, at least 99%, or more identical to SEQ ID NO: 1. In some embodiments, the at least one of two mutations comprises a D125A mutation, a D184A mutation, or an E220A mutation. In some embodiments, the two mutations are comprised of a D125A mutation and an D184A mutation. In some embodiments, the mutant integrase comprises a peptide sequence that is at least 80%, at least 85%, at least 90%, at least 95%, at least 99%, or more identical to SEQ ID NO: 5. In some embodiments, the two mutations are comprised of a D125A mutation and an E220A mutation. In some embodiments, the mutant integrase comprises a peptide sequence that is at least 80%, at least 85%, at least 90%, at least 95%, at least 99%, or more identical to SEQ ID NO: 6. In some embodiments, the two mutations comprises a D184A mutation and an E220A mutation. In some embodiments, the mutant integrase comprises a peptide sequence that is at least 80%, at least 85%, at least 90%, at least 95%, at least 99%, or more identical to SEQ ID NO: 7.

Described herein, is some aspects, is a recombinant retroviral vector comprising a nucleic acid construct comprising a polynucleotide sequence encoding a mutant integrase, wherein the mutant integrase, compared with a wild-type integrase, consists of three mutations in the $Mg^{2+}$ binding motif of the catalytic core domain. In some embodiments, at least one of three mutations consists of changing an aspartic acid (D) or a glutamic acid (E) to an amino acid having a hydrophobic side chain. In some embodiments, the at least one of three mutations comprises an amino acid selected from the group consisting of a valine (V), an alanine (A), a leucine (L), an isoleucine (I), and a phenylalanine (F). In some embodiments, the at least one of three mutations comprises the phenylalanine (F). In some embodiments, the at least one of three mutations comprises the alanine (A). In some embodiments, at least one of three mutations comprises changing an aspartic acid (D) or a glutamic acid (E) to an amino acid having a positive charge side chain. In some embodiments, the at least one of three mutations comprises a histidine (H). In some embodiments, at least one of three mutations comprises changing an aspartic acid (D) or a glutamic acid (E) to an amino acid having a polar charge side chain. In some embodiments, the at least one of three mutations comprises a serine (S). In some embodiments, the at least one of three mutations comprises changing an aspartic acid (D) or a glutamic acid (E) to a cysteine (C). In some embodiments, the mutant integrase comprises a peptide sequence that is at least 80%, at least 85%, at least 90%, at least 95%, at least 99%, or more identical to SEQ ID NO: 1. In some embodiments, the at least one of three mutations comprises a D125A mutation, a D184A mutation, or an E220A mutation. In some embodiments, the three mutations comprises a D125A mutation, a D184A mutation, or an E220A mutation. In some embodiments, the three mutations comprises a D125A mutation, a D184A mutation, and an E220A mutation. In some embodiments, the mutant integrase comprises a peptide sequence that is at least 80%, at least 85%, at least 90%, at least 95%, at least 99%, or more identical to SEQ ID NO: 8. In some embodiments, the nucleic acid construct further encodes a payload. In some embodiments, the payload comprises a cytokine. In some embodiments, the cytokine comprises an interleukin-7. In some embodiments, the cytokine comprises an interleukin-12. In some embodiments, the cytokine comprises an interferon. In some embodiments, the interferon comprises IFN-α. In some embodiments, the payload comprises a thymidine kinase. In some embodiments, the thymidine kinase comprises a mutant thymidine kinase. In some embodiments, the payload comprises an antigen. In some embodiments, the antigen comprises a viral protein. In some embodiments, the viral protein comprises a SARS-CoV-2 protein. In some embodiments, the viral protein comprises an influenza protein. In some embodiments, the antigen comprises a pathogen protein.

Described herein, in some aspects, is a method of treating a disease or condition in a subject, comprising administering a therapeutically effective amount of a pharmaceutical composition comprising the recombinant retroviral vector described herein to the subject.

Described herein, in some aspects, is a method of vaccinating a subject, comprising administering a pharmaceutical composition comprising the recombinant retroviral vector described herein to the subject.

BRIEF DESCRIPTION OF THE DRAWINGS

This patent application contains at least one drawing executed in color. Copies of this patent or patent application with color drawing(s) will be provided by the Office upon request and payment of the necessary fee.

FIG. 2 illustrates sequencing results of the D184A mutant.

FIG. 3 illustrates sequencing results of the D125A/E220A mutant.

FIG. 5 illustrates vTK/GCV cell kill activities with 7 different mutants.

FIG. 12C illustrates relative integration of the vector by qPCR between wtGP and integrase-defective mutants.

FIG. 16A illustrates Western blotting of secreted Spike proteins from retroviral vector transduced A375 cells. "IDRV1" denotes retroviral vector encoding a mutant integrase (integrase with D184A mutation). Each day presents accumulated proteins.

FIG. 16B illustrates Western blotting of secreted S2 proteins from retroviral vector transduced A375 cells. "IDRV1" denotes retroviral vector encoding a mutant integrase (integrase with D184A mutation). Each day presents accumulated proteins.

FIG. 16C illustrates Western blotting of secreted full-length Spike proteins and S2 proteins from retroviral vector transduced A375 cells. Retroviral vector also expressed a mutant integrase (IDRV2: D125A mutation and D184A mutation) described herein. Each day presents accumulated proteins.

FIG. 18A illustrates expression of Omicron Spike proteins detected by Western blotting after testing cells were transduced with retroviral vector described herein.

The novel features of the disclosure are set forth with particularity in the appended claims. A better understanding of the features and advantages of the present disclosure will be obtained by reference to the following detailed description that sets forth illustrative embodiments.

DETAILED DESCRIPTION

Overview

Described herein, in some aspects, is a vector comprising at least one amino acid mutation. In some aspects, the vector is a recombinant retroviral vector (or a retrovector) comprising the at least one amino acid mutation, where the at least one amino acid mutation is in the integrase encoded by the recombinant retroviral vector, thus creating a mutant integrase. In some aspects, the mutant integrase comprising the at least one amino acid mutation is dysfunctional and can no longer integrate the recombinant retroviral vector into genome of the host cell. In some embodiments, the vector comprises a nucleic acid construct comprising at least one polynucleotide sequence encoding a mutant reverse transcriptase. In some aspects, the mutant reverse transcriptase comprises at least one amino acid mutation, where the mutant reverse transcriptase can no longer convert the vector into DNA for inserting into the genome of the host cell. In some embodiments, the vector comprises a nucleic acid construct comprising at least one polynucleotide sequence encoding both the mutant integrase and the mutant reverse transcriptase.

Figure 1:
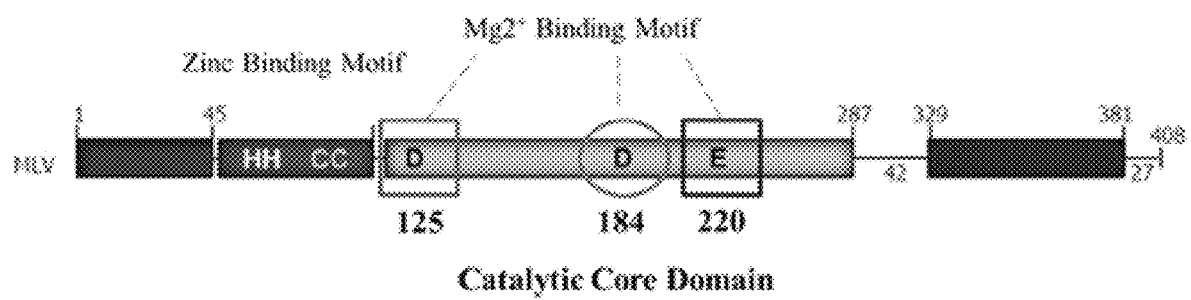
FIG. 1 illustrates s schematic representation of MLV integrase highlighting the triad D125, D184, and E220 forming the $Mg^{2+}$ binding motif in the catalytic core domain. HH-CC motif involves in Zinc binding domain. The HH-CC motif is a specific type of $Zn^{2+}$ ion chelation site found in zinc finger protein.

In some aspects, the recombinant retroviral vector comprising a nucleic acid construct comprising a polynucleotide sequence encoding a mutant integrase, wherein the mutant integrase, compared with a wild-type integrase, comprises the at least one amino acid mutation in $Mg^{2+}$ binding motif of catalytic core domain of the mutant integrase. FIG. 1 illustrates an exemplary vector diagram showing the location of the at least one mutation in the $Mg^{2+}$ binding motif of catalytic core domain of the integrase. In embodiments, the mutant integrase comprises one, two, three, or more amino acid mutations in the $Mg^{2+}$ binding motif of catalytic core domain of the mutant integrase. In some aspects, the vector comprising the mutant integrase can also encode a payload. In some embodiments, the payload comprises a therapeutic. In some embodiments, the vector described herein comprises a recombinant retroviral vector comprising the payload encoding an antigen, where the antigen can stimulate innate immunity (e.g., as a vaccine). In some embodiments, the antigen comprises a pathogen polypeptide or fragment thereof or a cancer polypeptide or fragment thereof. In some embodiments, the cancer polypeptide or fragment thereof is associated with a cancer cell or a tumor microenvironment. In some embodiments, the pathogen polypeptide or fragment thereof comprises a virus polypeptide or fragment thereof. In some embodiments, the virus polypeptide or fragment thereof comprises a coronavirus polypeptide or fragment thereof. In some embodiments, the virus polypeptide or fragment thereof comprises an influenza polypeptide or fragment thereof.

In some embodiments, the pathogen polypeptide or fragment thereof comprises a bacterium polypeptide or fragment thereof. In some embodiments, the pathogen polypeptide or fragment thereof comprises a fungus polypeptide or fragment thereof. In some embodiments, the pathogen polypeptide or fragment thereof comprises a protist polypeptide or fragment thereof. In some embodiments, the pathogen polypeptide or fragment thereof comprises a protozoa polypeptide or fragment thereof.

In some embodiments, the payload comprises an antigen, where the antigen can elicit immune response, thus vaccinating a subject administered with the vector. In some aspects, described herein is a method of treating a disease or condition in a subject by administering the vector (e.g., the recombinant retroviral vector described herein) to the subject, where the vector delivers a therapeutic as payload of the vector. In some aspects, described herein is a method of vaccinating a subject by administering the vector (e.g., the recombinant retroviral vector described herein) to the subject, where the vector delivers an antigen as payload. The antigen can then trigger innate immune response against the antigen, thus vaccinating the subject.

Vector

Described herein, in some aspects, is a vector such as a recombinant retroviral vector comprising a nucleic acid construct comprising at least one polynucleotide sequence encoding a mutant integrase. In some embodiments, the vector comprises a nucleic acid construct comprising at least one polynucleotide sequence encoding a mutant reverse transcriptase. In some embodiments, the vector comprises a nucleic acid construct comprising at least one polynucleotide sequence encoding both the mutant integrase and the mutant reverse transcriptase.

Figure 4:
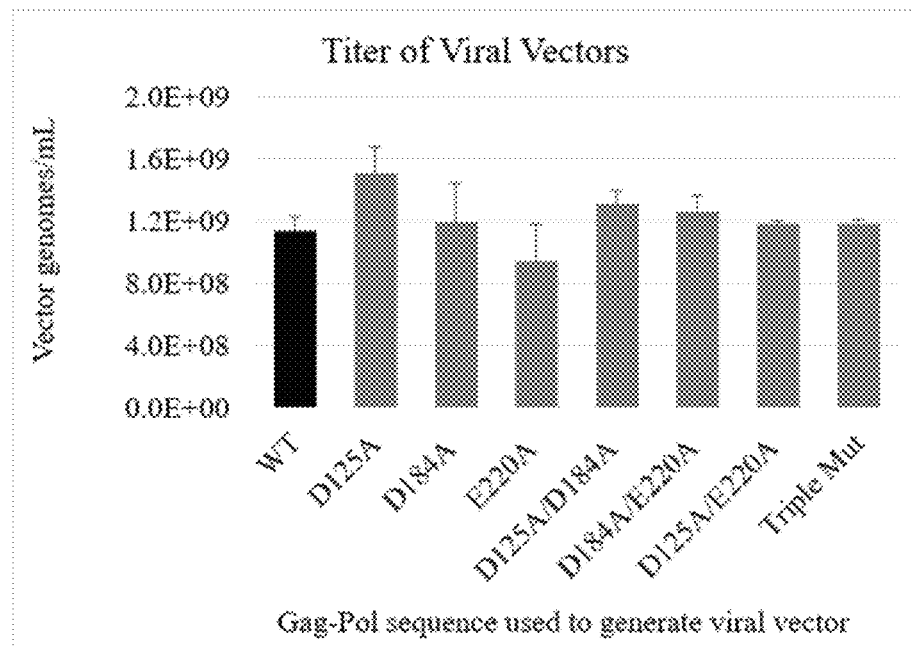
FIG. 4 illustrates physical titers of vectors generated with 7 different mutants.
Figure 6A:
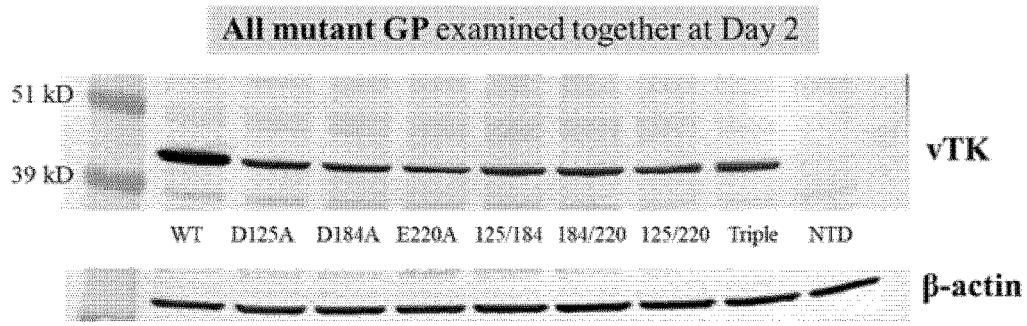
FIG. 6A illustrates early vTK expression detected by Western blotting.
Figure 6B:
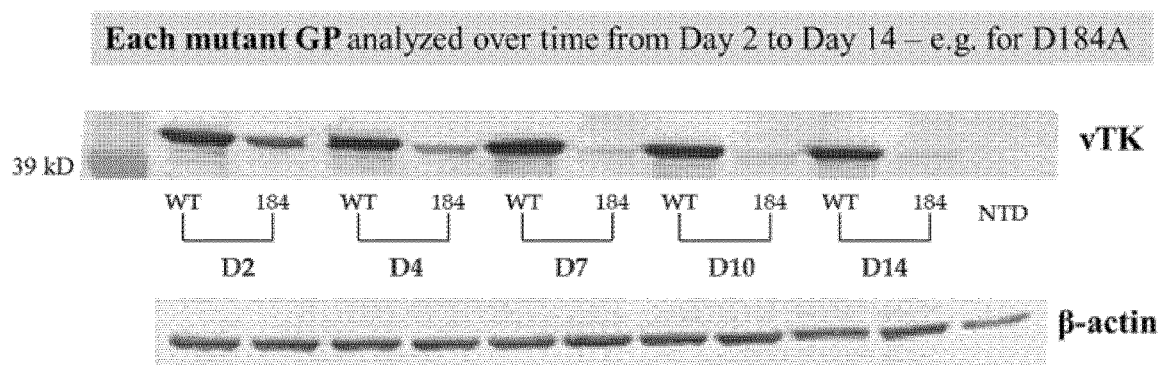
FIG. 6B illustrates exemplary Western blot expression analysis from days 2 to 14 for D184A mutant.
Figure 7:
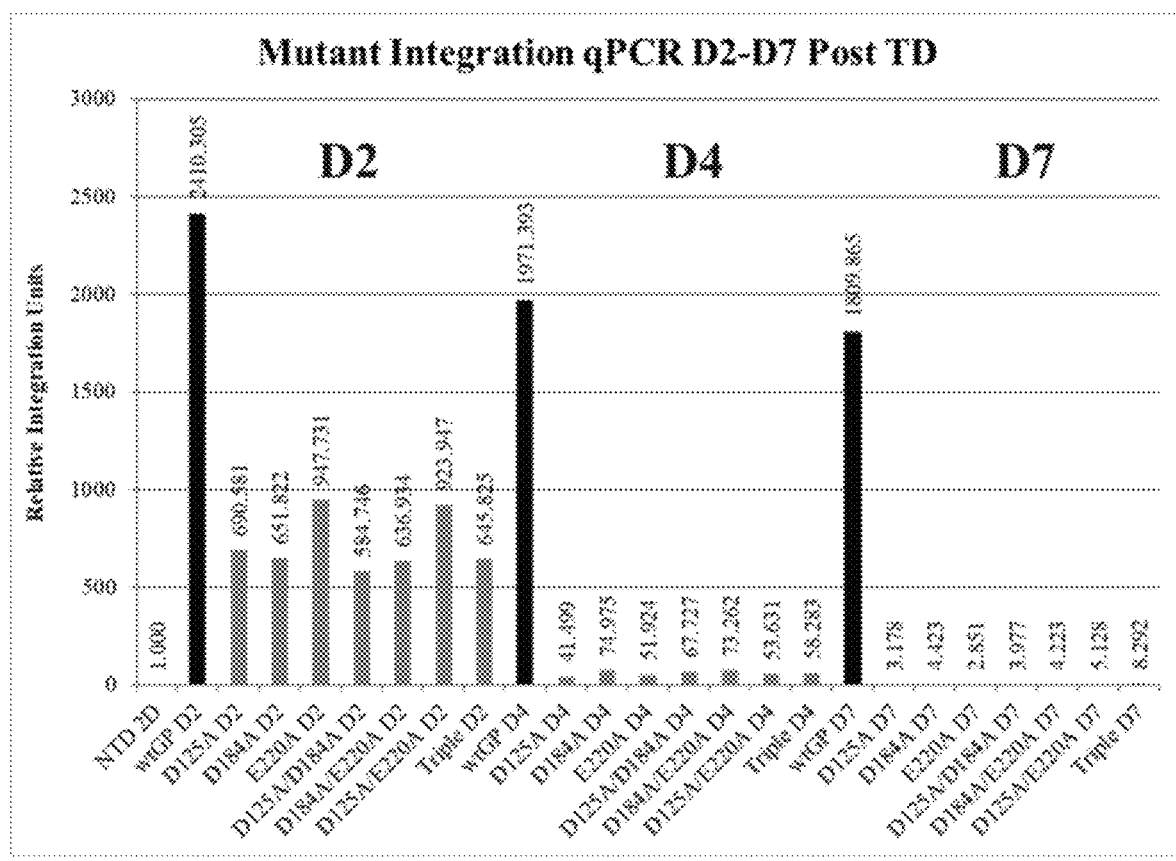
FIG. 7 illustrates relative integration qPCR with 7 different mutants at Day 2, 4, and 7.
Figure 8:
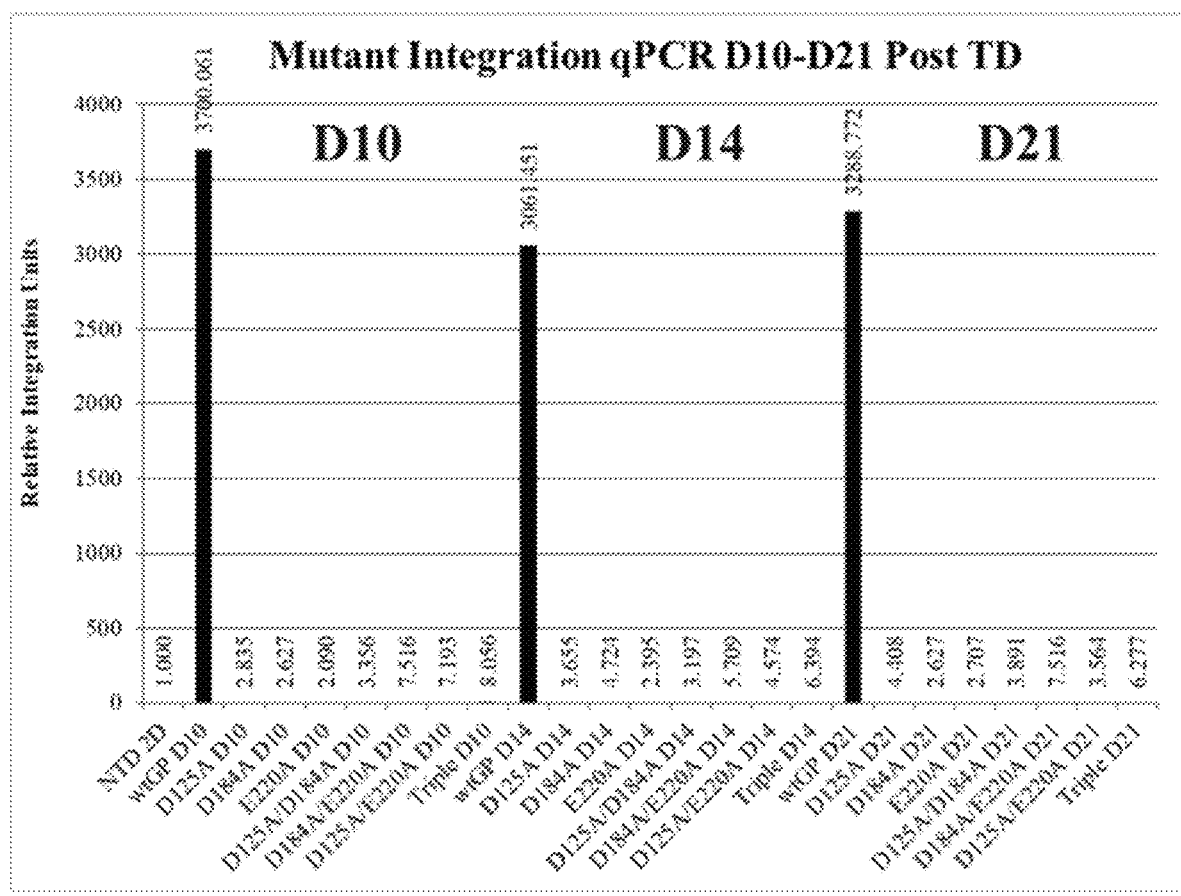
FIG. 8 illustrates relative Integration qPCR with 7 different mutants at Day 10, 14, and 21.
Figure 9:
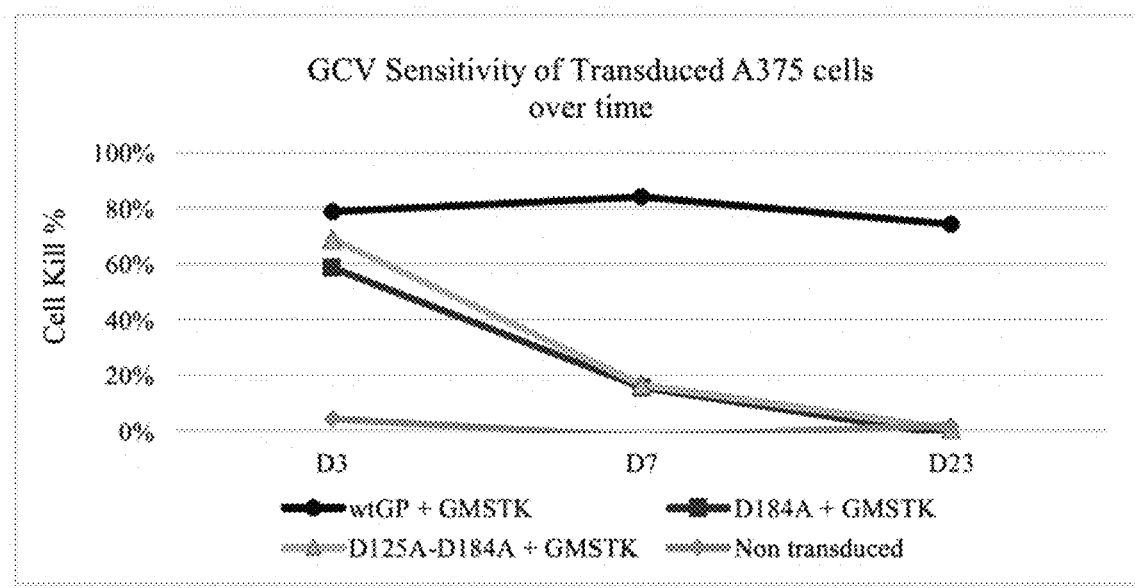
FIG. 9 illustrates vTK/GCV cell kill activities of retroviral vectors produced from integrase-defective gagpol cell lines.

In some embodiments, the mutant integrase, compared with a wild-type integrase comprising a polypeptide sequence of SEQ ID NO: 1, comprises at least one amino acid mutation. In some embodiments, the mutant integrase comprises a polypeptide sequence that is at least 80%, at least 85%, at least 90%, at least 95%, at least 99%, or more identical to SEQ ID NO: 1. FIG. 2 and FIG. 3 illustrate alignment of polypeptide sequences of exemplary mutant integrase described herein against wild-type integrase polypeptide sequence. FIG. 4 illustrates that the mutant integrases described herein, while dysfunctional for integrating the vector into the host genome, did not alter viral titer. FIG. 5 and FIG. 9-12 illustrate that the vector comprising the mutant integrase could deliver a payload (a thymidine kinase described herein) for killing cells in the presence of a prodrug (GCV). FIG. 6 illustrates that the expression of the payload (thymidine kinase, vTK) was not altered by the mutant integrase. FIG. 7 and FIG. 8 illustrate the vector comprising the mutant integrase was not integrated into the host genome for at least 21 days after the host cell was contacted with the vector.

In some embodiments, the mutant integrase comprises at least one, at least two, at least three, or more amino acid mutations. In some embodiments, the mutant integrase comprises one, two, three, or more amino acid mutations. In some embodiments, the mutant integrase comprises one amino acid mutation. In some embodiments, the mutant integrase comprises two amino acid mutations. In some embodiments, the mutant integrase comprises three amino acid mutations. In some embodiments, the mutant integrase comprises at least one, at least two, at least three, or more amino acid mutations in the $Mg^{2+}$ binding motif of catalytic core domain of the mutant integrase. In some embodiments, the mutant integrase comprises one, two, three, or more amino acid mutations in the $Mg^{2+}$ binding motif of catalytic core domain of the mutant integrase. In some embodiments, the mutant integrase comprises one amino acid mutation in the $Mg^{2+}$ binding motif of catalytic core domain of the mutant integrase. In some embodiments, the mutant integrase comprises two amino acid mutations in the $Mg^{2+}$ binding motif of catalytic core domain of the mutant integrase. In some embodiments, the mutant integrase comprises three amino acid mutations in the $Mg^{2+}$ binding motif of catalytic core domain of the mutant integrase.

In some embodiments, the mutant integrase comprises at least one amino acid mutation, where the at least one amino acid mutation comprises changing an aspartic acid (D) or a glutamic acid (E) of the wild-type integrase to an amino acid having a hydrophobic side chain. In some embodiments, the amino acid having a hydrophobic side chain is selected from the group consisting of a valine (V), an alanine (A), a leucine (L), an isoleucine (I), and a phenylalanine (F). In some embodiments, the mutant integrase comprises at least one amino acid mutation, where the at least one amino acid mutation comprises changing an aspartic acid (D) or a glutamic acid (E) of the wild-type integrase to a phenylalanine (F). In some embodiments, the mutant integrase comprises at least one amino acid mutation, where the at least one amino acid mutation comprises changing an aspartic acid (D) or a glutamic acid (E) of the wild-type integrase to an alanine (A). In some embodiments, the mutant integrase comprises at least one amino acid mutation, where the at least one amino acid mutation comprises changing an aspartic acid (D) or a glutamic acid (E) of the wild-type integrase to an amino acid having a positive charge side chain. In some embodiments, the mutant integrase comprises at least one amino acid mutation, where the at least one amino acid mutation comprises changing an aspartic acid (D) or a glutamic acid (E) of the wild-type integrase to an amino acid having a positive charge side chain, where the positive charge side chain is a histidine (H). In some embodiments, the mutant integrase comprises at least one amino acid mutation, where the at least one amino acid mutation comprises changing an aspartic acid (D) or a glutamic acid (E) of the wild-type integrase to an amino acid having a polar charge side chain. In some embodiments, the mutant integrase comprises at least one amino acid mutation, where the at least one amino acid mutation comprises changing an aspartic acid (D) or a glutamic acid (E) of the wild-type integrase to an amino acid having a polar charge side chain, where the positive charge side chain is a serine (S). In some embodiments, the mutant integrase comprises at least one amino acid mutation, where the at least one amino acid mutation comprises changing an aspartic acid (D) or a glutamic acid (E) of the wild-type integrase to cysteine (C).

In some embodiments, the mutant integrase comprises at least one amino acid mutation in the $Mg^{2+}$ binding motif of catalytic core domain of the mutant integrase, where the at least one amino acid mutation comprises changing an aspartic acid (D) or a glutamic acid (E) of the wild-type integrase to an amino acid having a hydrophobic side chain. In some embodiments, the amino acid having a hydrophobic side chain is selected from the group consisting of a valine (V), an alanine (A), a leucine (L), an isoleucine (I), and a phenylalanine (F). In some embodiments, the mutant integrase comprises at least one amino acid mutation in the $Mg^{2+}$ binding motif of catalytic core domain of the mutant integrase, where the at least one amino acid mutation comprises changing an aspartic acid (D) or a glutamic acid (E) of the wild-type integrase to a phenylalanine (F). In some embodiments, the mutant integrase comprises at least one amino acid mutation in the $Mg^{2+}$ binding motif of catalytic core domain of the mutant integrase, where the at least one amino acid mutation comprises changing an aspartic acid (D) or a glutamic acid (E) of the wild-type integrase to an alanine (A). In some embodiments, the mutant integrase comprises at least one amino acid mutation in the $Mg^{2+}$ binding motif of catalytic core domain of the mutant integrase, where the at least one amino acid mutation comprises changing an aspartic acid (D) or a glutamic acid (E) of the wild-type integrase to an amino acid having a positive charge side chain. In some embodiments, the mutant integrase comprises at least one amino acid mutation in the $Mg^{2+}$ binding motif of catalytic core domain of the mutant integrase, where the at least one amino acid mutation comprises changing an aspartic acid (D) or a glutamic acid (E) of the wild-type integrase to an amino acid having a positive charge side chain, where the positive charge side chain is a histidine (H). In some embodiments, the mutant integrase comprises at least one amino acid mutation in the $Mg^{2+}$ binding motif of catalytic core domain of the mutant integrase, where the at least one amino acid mutation comprises changing an aspartic acid (D) or a glutamic acid (E) of the wild-type integrase to an amino acid having a polar charge side chain. In some embodiments, the mutant integrase comprises at least one amino acid mutation in the $Mg^{2+}$ binding motif of catalytic core domain of the mutant integrase, where the at least one amino acid mutation comprises changing an aspartic acid (D) or a glutamic acid (E) of the wild-type integrase to an amino acid having a polar charge side chain, where the positive charge side chain is a serine (S). In some embodiments, the mutant integrase comprises at least one amino acid mutation in the $Mg^{2+}$ binding motif of catalytic core domain of the mutant integrase, where the at least one amino acid mutation comprises changing an aspartic acid (D) or a glutamic acid (E) of the wild-type integrase to cysteine (C).

In some embodiments, the mutant integrase comprises a single mutation. In some embodiments, the mutant integrase comprises a single mutation at position 125 of the wild-type integrase. In some embodiments, the mutant integrase comprises a single mutation comprising a substitution of an aspartic acid (D) to alanine (A) at position 125, a D125A mutation, of the wild-type integrase. In some embodiments, the mutant integrase comprising a single mutation comprising a substitution of the D125A mutation comprises a polypeptide sequence that is at least 80%, at least 85%, at least 90%, at least 95%, at least 99%, or more identical to SEQ ID NO: 2. In some embodiments, the mutant integrase comprising a single mutation comprising a substitution of the D125A mutation comprises a polypeptide sequence that is SEQ ID NO: 2.

In some embodiments, the mutant integrase comprises a single mutation at position 184 of the wild-type integrase. In some embodiments, the mutant integrase comprises a single mutation comprising a substitution of an aspartic acid (D) to alanine (A) at position 184, a D184A mutation, of the wild-type integrase. In some embodiments, the mutant integrase comprising a single mutation comprising a substitution of the D184A mutation comprises a polypeptide sequence that is at least 80%, at least 85%, at least 90%, at least 95%, at least 99%, or more identical to SEQ ID NO: 3. In some embodiments, the mutant integrase comprising a single mutation comprising a substitution of the D184A mutation comprises a polypeptide sequence that is SEQ ID NO: 3.

In some embodiments, the mutant integrase comprises a single mutation at position 220 of the wild-type integrase. In some embodiments, the mutant integrase comprises a single mutation comprising a substitution of a glutamic acid (E) to alanine (A) at position 220, a E220A mutation, of the wild-type integrase. In some embodiments, the mutant integrase comprising a single mutation comprising a substitution of the E220A mutation comprises a polypeptide sequence that is at least 80%, at least 85%, at least 90%, at least 95%, at least 99%, or more identical to SEQ ID NO: 4. In some embodiments, the mutant integrase comprising a single mutation comprising a substitution of the E220A mutation comprises a polypeptide sequence that is SEQ ID NO: 4.

In some embodiments, the mutant integrase comprises two mutations. In some embodiments, the mutant integrase comprises two mutations, where the first mutation comprises a substitution of an aspartic acid (D) to alanine (A) at position 125, a D125A mutation, of the wild-type integrase; and the second mutation comprises a substitution of an aspartic acid (D) to alanine (A) at position 184, a D184A mutation, of the wild-type integrase. In some embodiments, the mutant integrase comprising two mutations comprising a substitution of the D125A mutation and a substitution of the D184A mutations comprises a polypeptide sequence that is at least 80%, at least 85%, at least 90%, at least 95%, at least 99%, or more identical to SEQ ID NO: 5. In some embodiments, the mutant integrase comprising two mutations comprising a substitution of the D125A mutation and a substitution of the D184A mutations comprises a polypeptide sequence that is SEQ ID NO: 5.

In some embodiments, the mutant integrase comprises two mutations, where the first mutation comprises a substitution of an aspartic acid (D) to alanine (A) at position 125, a D125A mutation, of the wild-type integrase; and the second mutation comprises a substitution of a glutamic acid (E) to alanine (A) at position 220, a E220A mutation, of the wild-type integrase. In some embodiments, the mutant integrase comprising two mutations comprising a substitution of the D125A mutation and a substitution of the E220A mutations comprises a polypeptide sequence that is at least 80%, at least 85%, at least 90%, at least 95%, at least 99%, or more identical to SEQ ID NO: 6. In some embodiments, the mutant integrase comprising two mutations comprising a substitution of the D125A mutation and a substitution of the E220A mutations comprises a polypeptide sequence that is SEQ ID NO: 6.

In some embodiments, the mutant integrase comprises two mutations, where the first mutation comprises a substitution of an aspartic acid (D) to alanine (A) at position 184, a D184A mutation, of the wild-type integrase; and the second mutation comprises a substitution of a glutamic acid (E) to alanine (A) at position 220, a E220A mutation, of the wild-type integrase. In some embodiments, the mutant integrase comprising two mutations comprising a substitution of the D184A mutation and a substitution of the E220A mutations comprises a polypeptide sequence that is at least 80%, at least 85%, at least 90%, at least 95%, at least 99%, or more identical to SEQ ID NO: 7. In some embodiments, the mutant integrase comprising two mutations comprising a substitution of the D184A mutation and a substitution of the E220A mutations comprises a polypeptide sequence that is SEQ ID NO: 7.

In some embodiments, the mutant integrase comprises three mutations. In some embodiments, the mutant integrase comprises three mutations, where the first mutation comprises a substitution of an aspartic acid (D) to alanine (A) at position 125, a D125A mutation, of the wild-type integrase; the second mutation comprises a substitution of an aspartic acid (D) to alanine (A) at position 184, a D184A mutation, of the wild-type integrase; and the third mutation comprises a substitution of an glutamic acid (E) to alanine (A) at position 220, a E220A mutation, of the wild-type integrase. In some embodiments, the mutant integrase comprising three mutations comprises a polypeptide sequence that is at least 80%, at least 85%, at least 90%, at least 95%, at least 99%, or more identical to SEQ ID NO: 8. In some embodiments, the mutant integrase comprising three mutations comprises a polypeptide sequence that is SEQ ID NO: 8.

In some embodiments, the vector comprising the at least one amino acid mutation renders the integrase dysfunctional. In some embodiments, the mutant integrase can no longer introduce the vector (e.g., a recombinant retroviral vector) into genome of a host cell comprising the vector. In some embodiments, the vector comprising the mutant integrase encodes at least one therapeutic or at least one antigen. In some embodiments, the at least one therapeutic comprises a cytokine. In some embodiments, cytokine comprises an interleukin or an interferon. In some embodiments, the vector encodes at least one interleukin subunit. In some embodiments, the vector encodes at least two interleukin subunits, where the at least two interleukin subunits are the same or different. In some embodiments, the vector encodes one interleukin subunit. In some embodiments, the vector encodes two interleukin subunits. In some embodiments, the vector encodes two different interleukin subunits. In some embodiments, the vector encodes two or more different interleukin subunits. In some embodiments, the vector comprises at least one start codon for expressing the interleukin, the subunit of the interleukin, or a combination thereof. In some embodiments, the vector comprises at least two start codons for expressing two interleukins, two subunits of the interleukin, or a combination thereof. In some embodiments, the vector comprises two codons each for expressing an interleukin subunit. Non-limiting example of the interleukin can include IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, IL-36, IL-37, IL-38, IL-39, IL-40, or IL-41. In some embodiments, the interleukin comprises IL-7. In some embodiments, the interleukin comprises IL-12.

In some embodiments, the vector comprising the mutant integrase encodes a therapeutic comprising an interferon. In some embodiments, the interferon comprises IFNα, IFNβ, IFNγ, or a combination thereof.

In some embodiments, the vector comprises at least one promoter for expressing the at least one polynucleotide. For example, the vector comprises a CMV promoter for expressing the at least one polynucleotide encoding the interleukin (e.g., the P40 subunit and the P35 subunit) described herein. In some aspects, the promoter comprises a muscle specific promoter such as HSA (human skeletal α-actin promoter), a muscle creatine kinase (MCK)-gene based promoter such as CK6 or MHCK7 promoter; a Desmin gene promoter (DES); a constitutive human promoter EF-1α (Elongation Factor 1α). Other example of the promoter can include the retroviral LTR; the SV40 promoter; the Rous Sarcoma Virus (RSV) promoter; the histone promoter; the polIII promoter, the 3-actin promoter; inducible promoters, such as the MMTV promoter, the metallothionein promoter; heat shock promoters; adenovirus promoters; the albumin promoter; the ApoAI promoter; B19 parvovirus promoters; human globin promoters; viral thymidine kinase promoters, such as the Herpes Simplex Virus thymidine kinase promoter; retroviral LTRs; human growth hormone promoters, and the MxIFN inducible promoter. In some embodiments, the promoter is a tissue-specific promoter. In some embodiments, a tissue specific promoter is chosen from the group including the tyrosinase related promoters (TRP-1 and TRP-2), DF3 enhancer (for breast cells), SLPI promoter (secretory leucoprotease inhibitor-expressed in many types of carcinomas), TRS (tissue specific regulatory sequences), α-fetoprotein promoters (specific for normal hepatocytes and transformed hepatocytes, respectively), the carcino-embryonic antigen promoter (for use in transformed cells of the gastrointestinal tract, lung, breast and other tissues), the tyrosine hydroxylase promoter (for melanocytes), choline acetyl transferase or neuron specific enolase promoters for use in neuroblastomas, the regulatory sequence for glial fibroblastomas, the tyrosine hydroxylase promoter, c-erb B-2 promoter, PGK promoter, PEPCK promoter, whey acidic promoter (breast tissue), and casein promoter (breast tissue) and the adipocyte P2 promoter. In some embodiments, the promoter is a viral-specific promoter (e.g., retroviral promoters, as well as others such as HIV promoters), hepatitis, herpes (e.g., EBV). In some embodiments, the promoter is the native HSV-TK promoter. In some embodiments, the promoter is a bacterial, fungal or parasitic (e.g., malarial)-specific promoter utilized in order to target a specific cell or tissue which is infected with a virus, bacteria, fungus or parasite. In some aspects, the vector comprises a nucleic acid sequence for encoding a tag such as His tag or a Flag tag for purification, imaging, or expression control purpose.

In some embodiments, the vector (e.g., a recombinant retroviral vector described herein) comprises at least one modified untranslated region (UTR). In some embodiments, the at least one UTR is a 5'-UTR located at 5' end of the nucleic acid sequence of the payload. In some embodiments, the at least one UTR is a 3'-UTR located at 3' end of the nucleic acid sequence of the payload. In some embodiments, the at least one UTR comprises both a 5'-UTR and a 3'-UTR located at both 5' end and 3' end of the nucleic acid sequence of the payload. In some embodiments, the at least one modified UTR increases expression of the payload compared to if the payload is flanked by a wild-type UTR.

In some aspects, the vector is a viral vector such as a retroviral vector. Viral vectors, and especially retroviral vectors, have become the most widely used method for inserting genes into mammalian, e.g., human cells. Other viral vectors, in some embodiments, are derived from lentivirus, poxviruses, herpes simplex virus I, adenoviruses, adeno-associated viruses, or Sindbis viruses. Non-limiting examples of viral vectors can include retroviral vectors, adenoviral vectors, adeno-associated viral vectors (AAVs), pox vectors, parvoviral vectors, baculovirus vectors, measles viral vectors, or herpes simplex virus vectors (HSVs). In some instances, the recombinant retroviral vectors include gamma-retroviral vectors such as vectors derived from the Moloney Murine Leukemia Virus (MoMLV, MMLV, MuLV, or MLV) or the Murine Stem cell Virus (MSCV) genome. In some instances, the recombinant retroviral vectors also include lentiviral vectors such as those derived from the human immunodeficiency virus (HIV) genome. In some instances, AAV vectors include AAV1, AAV2, AAV4, AAV5, AAV6, AAV7, AAV8, or AAV9 serotype. In some instances, viral vector is a chimeric viral vector, comprising viral portions from two or more viruses. In additional instances, the viral vector is a recombinant viral vector.

In some embodiments, the recombinant retroviral vector comprises at least one modification, where the recombinant retroviral vector can encode at least one amino acid mutation for increasing targeting efficiency of the virus to a cell type. For example, a recombinant Sindbis retroviral vector can encode an E160G mutation in E2 protein of the Sindbis virus, where the E160G mutation increases targeting of the Sindbis virus to a dendritic cell. In such, the targeting of the dendritic can increase immune response and the efficacy of vaccination by contacting the dendritic cell with an antigen encoded by the recombinant retroviral vector.

Described herein, in some aspects, is a recombinant retroviral vector comprising a first nucleic acid sequence encoding a mutant integrase described herein and a second nucleic acid sequence encoding at least one payload. In some embodiments, the mutant integrase, when compared to a wild-type integrase, comprises at least one mutation in $Mg^{2+}$ binding motif of a catalytic core domain. For example, the at least one mutation can include a D125A mutation, a D184A mutation, or a combination of both D125 and D184A mutations. In some embodiments, the at least one payload comprises an antigen. In some embodiments, the antigen induces immune response in a cell. In some embodiments, the antigen comprises a pathogen polypeptide. In some embodiments, the pathogen polypeptide includes polypeptide derived from a bacterial pathogen, an alveolate pathogen, an amoebal pathogen, a fungal pathogen, a protozoan pathogen, a nematodal pathogen, a platyhelminthes pathogen, a viral pathogen, or a combination thereof. Table 1 provides a non-limiting example list for such pathogen(s) as described above, which may serve as a basis for the design of nucleotide sequences encoding pathogen-derived polypeptides for incorporation into retroviral vector(s) for transduction and eventual expression as antigenic payloads by transduced cells.

TABLE 1

Exemplary list of pathogens for obtaining the antigen comprising the pathogen polypeptide

| Pathogen | | |
|---|---|---|
| Class | Genus | Member |
| Bacterial | *Listeria* | *Listeria monocytogenes* |
| | *Bordetella* | *Bordetella brionchiseptica* |
| | | *Bordatella pertussis* |
| | | *Bordatella parapertussis* 1 |
| | | *Bordatella parapertussis* 2 |
| | *Rickettsia* | *Rickettsia rickettsii* |
| | | *Rickettsia akari* |
| | | *Rickettsia conorii* |
| | | *Rickettsia sibirica* |
| | | *Rickettsia australis* |
| | | *Rickettsia felis* |
| | | *Rickettsia japonica* |
| | | *Rickettsia africae* |
| | | *Rickettsia hoogstraalii* |
| | | *Rickettsia prowazekii* |
| | | *Rickettsia typhi* |
| | *Orientia* | *Orientia tsutsugamushi* |
| | | *Orientia chuto* |
| | *Piscireckettsia* | *Piscirickettsia salmonis* |
| | *Corynebacterium* | *Corynebacterium diptheria* |
| | | *Corynebacterium ulcerans* |

TABLE 1-continued

Exemplary list of pathogens for obtaining the antigen comprising the pathogen polypeptide

| Pathogen | | |
|---|---|---|
| Class | Genus | Member |
| | *Streptococcus* | *Streptococcus aureus* |
| | | *Streptococcus pyroenes* |
| | | *Streptococcus pneumoniae* |
| | | *Streptococcus agalactiae* (Group B Strep) |
| | *Clostridium* | *Clostridium botulinum* |
| | | *Clostridium perfringens* |
| | | *Clostridium difficle* |
| | | *Clostridium tetani* |
| | *Borrelia* | *Borrelia turcica* |
| | | *Borrelia coriaceae* |
| | | *Borrelia miyamotoi* |
| | | *Borrelia mayonii* |
| | | *Borrelia americana* |
| | | *Borrelia lanei* |
| | | *Borrelia turdi* |
| | | *Borrelia tanukii* |
| | | *Borrelia californiensis* |
| | | *Borrelia kurtenbachii* |
| | | *Borrelia yangtzensis* |
| | | *Borrelia valaisiana* |
| | | *Borrelia afzelii* |
| | | *Borrelia spielmanii* |
| | | *Borrelia maritima* |
| | | *Borrelia lusitaniae* |
| | | *Borrelia garinii garinii* |
| | | *Borrelia garinii bavariensis* |
| | | *Borrelia japonica* |
| | | *Borrelia sinica* |
| | | *Borrelia burgdorferi* |
| | | *Borrelia bissettii* |
| | | *Borrelia carolinensis* |
| | *Leptospira* | *Leptospira alexanderi* |
| | | *Leptospira borgpetersenii* |
| | | *Leptospira interrogans* |
| | | *Leptospira kirchneri* |
| | | *Leptospira mayottensis* |
| | | *Leptospira noguchii* |
| | | *Leptospira santorosai* |
| | | *Leptospira weilii* |
| | *Mycobacterium* | *Mycobacterium tuberculosis* |
| | | *Mycobacterium africanum* |
| | | *Mycobacterium orygis* |
| | | *Mycobacterium bovis* |
| | | *Mycobacterium microti* |
| | | *Mycobacterium canetti* |
| | | *Mycobacterium caprae* |
| | | *Mycobacterium pinnipedii* |
| | | *Mycobacterium suricattae* |
| | | *Mycobacterium mungi* |
| | *Vibrio* | *Vibrio vulnificus* |
| | | *Vibrio cholerae* |
| | *Bacillus* | *Bacillus anthracis* |
| | *Neorickettsia* | *Neorickettsia risticii* |
| | *Proteus* | *Proteus hauseri* |
| | | *Proteus mirabilis* |
| | | *Proteus myxofaciens* |
| | | *Proteus penneri* |
| | | *Proteus vulgaris* |
| | *Serratia* | *Serratia marcescens* |
| | | *Serratia plymuthica* |
| | | *Serratia liquefaciens* |
| | | *Serratia rubidaea* |
| | | *Serratia odorifera* |
| | | *Serratia fonticola* |
| | *Yersinia* | *Yersinia pestis* |
| | | *Yersina enterocolitica* |
| | | *Yersinia pseudotuberculosis* |
| | | *Yersenia Ruckerii* |
| | *Klebsiella* | *Klebsiella aerogenes* |
| | | *Klebsiella granulomatis* |
| | | *Klebsiella grimontii* |
| | | *Klebsiella huaxiensis* |
| | | *Klebsiella kielensis* |

TABLE 1-continued Exemplary list of pathogens for obtaining the antigen comprising the pathogen polypeptide

| Class | Genus | Member |
|---|---|---|
| | | Klebsiella michiganensis |
| | | Klebsiella milletis |
| | | Klebsiella oxytoca |
| | | Klebsiella pneumoniae |
| | | Klebsiella quasipneumoniae |
| | | Klebsiella similipneumoniae |
| | | Klebsiella quasivariicola |
| | | Klebsiella senegalensis |
| | | Klebsiella steroids |
| | | Klebsiella variicola |
| | Enterobacter | Enterobacter cloacae |
| | | Enterobacter cancerogenous |
| | | Enterobacter aerogenes |
| | | Enterobacter hormaechei |
| | Pluralibacter | Pluralibacter gergoviae |
| | Citrobacter | Citrobacter diversus |
| | | Citrobacter freundii |
| | | Citrobacter amalonaticus |
| | | Citrobacter braakii |
| | | Citrobacter farmeri |
| | | Citrobacter koseri |
| | | Citrobacter sedlakii |
| | | Citrobacter werkmanii |
| | | Citrobacter Youngae |
| | Salmonella | Salmonella bongori |
| | | Salmonella enterica subsp. Enterica |
| | | Salmonella choleraesuis |
| | | Salmonella dublin |
| | | Salmonella enteritidis |
| | | Salmonella gallinarum |
| | | Salmonella hadar |
| | | Salmonella heidelberg |
| | | Salmonella infantis |
| | | Salmonella paratyphi |
| | | Salmonella typhi |
| | | Salmonella typhimurium |
| | Shigella | Shigella boydii |
| | | Shigella dysenteriae |
| | | Shigella flexneri |
| | | Shigella sonnei |
| | Escherichia | Escherichia albertii |
| | | Escherichia coli |
| | | Escherichia fergusonii |
| | | Escherichia hermannii |
| | | Escherichia marmotae |
| | | Escherichia vulneris |
| Alveolate | Plasmodium | Plasmodium falciparum |
| | | Plasmodium knowlesi |
| | | Plasmodium vivax |
| | | Plasmodium ovale wallikeri |
| | | Plasmodium ovale curtisi |
| | | Plasmodium malariae |
| | Toxoplasma | Toxoplasma gondii |
| Amoebal | Naegleria | Naegleria fowleri |
| | Entabloeba | Entamoeba hystolytica |
| Fungal | Blastomyces | Blastomyces dermatitidis |
| | | Blasomyces gilchristi |
| | | Blastomyces helicus |
| | | Blastomyces percursus |
| | | Blastomyces emzantsi |
| | Coccidioides | Coccidioides immitis |
| | | Coccidioides posadasii |
| | Histoplasma | Histoplasma capsulatum |
| | Pneumocystis | Pneumocystis jirovecii |
| | Talaromyces | Talaromyces marneffei |
| | Sporothrix | Sporothrix schenkii |
| Protozoan | Leishmania | Leishmania aethiopica |
| | | Leishmania amazonensis |
| | | Leishmania arabica |
| | | Leishmania archibaldi |
| | | Leishmania aristedesi |
| | | Leishmania (Viannia) braziliensis |
| | | Leishmania chagasi |
| | | Leishmania donovani |
| | | Leishmania (Mundinia) enriettii |
| | | Leishmania forattinii |
| | | Leishmania garnhami |
| | | Leishmania gerbili |
| | | Leishmania (Viannia) guyanensis |
| | | Leishmania infantum |
| | | Leishmania killicki |
| | | Leishmania (Viannia) lainsoni |
| | | Leishmania major |
| | | Leishmania (Mundinia) macropodum |
| | | Leishmania (Mundinia) martiniquensis |
| | | Leishmania mexicana |
| | | Leishmania (Viannia) naiffi |
| | | Leishmania (Viannia) panamensis |
| | | Leishmania (Viannia) peruviana |
| | | Leishmania pifanoi |
| | | Leishmania (Viannia) shawi |
| | | Leishmania tarentolae |
| | | Leishmania tropica |
| | | Leishmania turanica |
| | | Leishmania waltoni |
| | | Leishmania venezuelensis |
| | Trypanosoma | Trypanosoma brucei |
| | | Trypanosoma rhodesiense |
| | | Trypanosoma equiperdum |
| | | Trypanosoma vivax |
| | | Trypanosoma congolense |
| | | Trypanosoma cruzi |
| | | Trypanosoma lewisi |
| | | Trypanosoma melophagium |
| | | Trypanosoma nabiasi |
| | | Trypanosoma rangeli |
| | | Trypanosoma theileri |
| | | Trypanosoma theodori |
| | | Trypanosoma cruzi |
| | | Trypanosoma cruzi marinkellei |
| | | Trypanosoma dionisii |
| | | Trypanosoma erneyi |
| | | Trypanosoma livingstonei |
| | | Trypanosoma wauwau |
| | | Trypanosoma conorhini |
| | | Trypanosoma rangeli |
| | Giardia | Giardia duodenalis |
| Nematodal | Onchocerca | Onchocerca volvulus |
| Platyhelminthes | Taenia | Taenia solium (pork) |
| | | Taenia saginata (beef) |
| | Diphyllobothrium | Diphyllobothrium latum |
| | | Diphyllobothrium dendriticum |
| | | Diphyllobothrium nihonkainense/klebanovskii |
| | Schistoma | Schistosoma bomfordi |
| | | Schistosoma bovis |
| | | Schistosoma curassoni |
| | | Schistosoma datta |
| | | Schistosoma edwardiense |
| | | Schistosoma guineensis |
| | | Schistosoma haematobium |
| | | Schistosoma harinasutai |
| | | Schistosoma hippopotami |
| | | Schistosoma incognitum |
| | | Schistosoma indicum |
| | | Schistosoma intercalatum |
| | | Schistosoma japonicum |
| | | Schistosoma kisumuensis |
| | | Schistosoma leiperi |
| | | Schistosoma malayensis |
| | | Schistosoma mansoni |

TABLE 1-continued

Exemplary list of pathogens for obtaining the antigen comprising the pathogen polypeptide

| Class | Genus | Member |
|---|---|---|
| | | *Schistosoma margrebowiei* |
| | | *Schistosoma mattheei* |
| | | *Schistosoma mekongi* |
| | | *Schistosoma ovuncatum* |
| | | *Schistosoma nasale* |
| | | *Schistosoma rodhaini* |
| | | *Schistosoma sinensium* |
| | | *Schistosoma spindale* |
| | | *Schistosoma turkestanicum* |
| Arthropod | *Sarcoptes* | *Sarcoptes scabiei* |
| Viral | Hepatovirus | Hepatitis A |
| | Orthohepadnavirus | Hepatitis B |
| | Deltavirus | Deltavirus italiense [HDV-1] |
| | | Deltavirus japanense [HDV-2] |
| | | Deltavirus peruense [HDV-3] |
| | | Deltavirus taiwanense [HDV-4] |
| | | Deltavirus togense [HDV-5] |
| | | Deltavirus carense [HDV-6] |
| | | Deltavirus cameroonense [HDV-7] |
| | | Deltavirus senegalense [HDV-8] |
| | Orthoherpesvirus | Orthoherpesvirus A (Hepatitis E) |
| | Alphavirus | Aura virus |
| | | Barmah Forest virus |
| | | Bebaru virus |
| | | Caaingua virus |
| | | Cabassou virus |
| | | Chikungunya virus |
| | | Eastern equine encephalitis virus |
| | | Eilat virus |
| | | Everglades virus |
| | | Fort Morgan virus |
| | | Getah virus |
| | | Highlands J virus |
| | | Madariaga virus |
| | | Mayaro virus |
| | | Middelburg virus |
| | | Mosso das Pedras virus |
| | | Mucambo virus |
| | | Ndumu virus |
| | | O'nyong'nyong virus |
| | | Pixuna virus |
| | | Rio Negro virus |
| | | Ross River virus |
| | | Salmon pancreas disease virus |
| | | Semliki Forest virus |
| | | Sindbis virus |
| | | Southern elephant seal virus |
| | | Tonate virus |
| | | Trocara virus |
| | | Una virus |
| | | Venezuelan equine encephalitis virus |
| | | Western equine encephalitis virus |
| | | Whataroa virus |
| | Novirhabdovirus | infectious hematopoetic necrosis virus (salmonid norvirhabdovirus) |
| | Gammaretrovirus | Feline leukemia virus |
| | Protoparvovirus | Feline panleukopenia virus |
| | | Canine parvovirus |
| | | Mink enteritis virus |
| | Deltaretrovirus | Bovine leukemia virus |
| | | Human T-cell lymphotropic virus |
| | Betacoronovirus/Embecovirus | Bovine coronavirus |
| | | Human coronavirus OC43 |
| | | China Rattus coronavirus HKU24 |
| | | Human coronavirus HKU1 |
| | | Murine coronavirus |
| | | Myodes coronavirus 2JL14 |
| | Betacoronovirus/Sarbecovirus | Severe Acute Respiratory Syndrome Coronavirus 1 |
| | | Severe Acute Respiratory Syndrome Coronavirus 2 |
| | | Bat SARS-like coronavirus WIV1 |
| | | Bat coronavirus RaTG13 |
| | Betacoronovirus/Merbecovirus | Middle East Respiratory Syndrome-Related Coronavirus |
| | | Pipistrellus bat coronavirus HKU5 |
| | | Tylonycteris bat coronavirus HKU4 |
| | Betacoronovirus/Nobecovirus | Eidolon bat coronavirus C704 |
| | | Rousettus bat coronavirus GCCDC1 |
| | | Rousettus bat coronavirus HKU9 |
| | Betacoronovirus/Hibbecovirus | Bat Hp-betacoronavirus Zhejiang2013 |
| | Paramyxovirus | Sosuga pararubulavirus |
| | Henipavirus | Hendra hinipivirus |
| | | Nipah virus |
| | Arenavirus | Lassa virus |
| | Ebolavirus | Ebola virus |
| | | Bundibugyo virus |
| | | Sudan virus |
| | | Tai Forest virus |
| | | Reston virus |
| | | Bombali virus |
| | Marburgvirus | Marburgh virus |
| | | Ravn virus |
| | Flavivirus | West Nile virus |
| | | Zika virus |
| | | dengue virus |
| | | yellow fever virus |
| | | Japanese encephalitis virus |
| | | Hepatitis C |
| | | Tick-borne encephalitis virus (and subtypes) |
| | Rotavirus | Rotavirus A |
| | | Rotavirus B |
| | | Rotavirus C |
| | | Rotavirus D |
| | | Rotavirus F |
| | | Rotavirus G |
| | | Rotavirus H |
| | | Rotavirus I |
| | | Rotavirus J |
| | Simplexvirus | Herpes simplex virus 1 |
| | | Herpes simplex virus 2 |
| | | Cercopihtecine herpesvirus |
| | Varicellovirus | Bovine alphaherpesvirus 1 |
| | | Bovine alphaherpesvirus 5 |
| | | Bubaline alphaherpesvirus 1 |
| | | Canid alphaherpesvirus 1 |
| | | Caprine alphaherpesvirus 1 |
| | | Cercopithecine alphaherpesvirus 9 |
| | | Cervid alphaherpesvirus 1 |
| | | Cervid alphaherpesvirus 2 |
| | | Cervid alphaherpesvirus 3 |
| | | Equid alphaherpesvirus 1 |
| | | Equid alphaherpesvirus 3 |
| | | Equid alphaherpesvirus 4 |
| | | Equid alphaherpesvirus 8 |
| | | Equid alphaherpesvirus 9 |
| | | Felid alphaherpesvirus 1 |
| | | Human alphaherpesvirus 3 |
| | | Monodontid alphaherpesvirus 1 |
| | | Phocid alphaherpesvirus 1 |
| | | Suid alphaherpesvirus 1 |
| | Lymphocryptovirus | Human gammaherpesvirus 4 (Epstein-Barr virus) |

TABLE 1-continued

Exemplary list of pathogens for obtaining the antigen comprising the pathogen polypeptide

| Class | Genus | Member |
|---|---|---|
| | Cytomegalovirus | Human betaherpesvirus 5 |
| | Rhadinovirus | Kaposi's sarcoma-associated herpesvirus |
| | | Murid gammaherpesvirus 4 |
| | Enterovirus | Enterovirus A (including subtype A71) |
| | | Enterovirus B (including coxsackie B virus subtypes) |
| | | Enterovirus C (including polioviruses 1, 2, and 3) |
| | | Rhinovirus A |
| | | Rhinovirus B |
| | | Rhinovirus C |
| | Alphainfluenzavirus | Influenza A |
| | Betainfluenzavirus | Influenza B |
| | Gammainfluenzavirus | Influenza C |
| | Deltainfluenzavirus | Influenza D |
| | Isavirus | Infectious Salmon Anemia Virus |
| | Quaranjavirus | Johnston Atoll Virus |
| | | Quaranfil virus |
| | Thogotovirus | Dhori thogotovirus |
| | | Thogoto thogotovirus |
| | Morbilivirus | Measles morbillivirus |
| | | Canine morbillivirus (distemper) |
| | | Cetacean morbillivirus |
| | | Feline morbillivirus |
| | | Ovine rinderpest |
| | | Phocine morbillivirus |
| | | Rinderpest morbillivirus |
| | Rubivirus | Rubivirus rubellae |
| | | Rubivirus ruteetense |
| | | Rubivirus strelense |
| | Orthorubulavirus | Mumps orthorubulavirus |
| | Metapneumovirus | Avian metapneumovirus |
| | | Human metapneumovirus |
| | Orthopneumovirus | Human orthopneumovirus |
| | Alphapapillomavirus | Human alphapapillomavirus (all subtypes by L1 gene) |
| | Betapapillomavirus | Human betapapillomavirus (all subtypes by L1 gene) |
| | Gammapapillomavirus | Human gammapapillomavirus (all subtypes by L1 gene) |
| | Deltapapillomavirus | Bos taurus deltaapapillomavirus (all subtypes by L1 gene) |
| | Epsilonpapillomavirus | Bos taurus episilonpapillomavirus (all subtypes by L1 gene) |
| | Xipapillomavirus | Bos taurus Xipapillomavirus (all subtypes by L1 gene) |
| | Lentivirus | Human immunodeficiency virus 1 |
| | | Human immunodeficiency virus 2 |
| | Orthohantavirus | Andes orthohantavirus |
| | | Asama orthohantavirus |
| | | Asikkala orthohantavirus |
| | | Bayou orthohantavirus |
| | | Black Creek Canal orthohantavirus |
| | | Bowe orthohantavirus |
| | | Bruges orthohantavirus |
| | | Cano Delgadito orthohantavirus |
| | | Cao Bang orthohantavirus |
| | | Choclo orthohantavirus |
| | | Dabieshan orthohantavirus |
| | | Dobrava-Belgrade orthohantavirus |
| | | El Moro Canyon orthohantavirus |
| | | Fugong orthohantavirus |
| | | Fusong orthohantavirus |
| | | Hantaan orthohantavirus |
| | | Jeju orthohantavirus |
| | | Kenkeme orthohantavirus |
| | | Khabarovsk orthohantavirus |
| | | Laguna Negra orthohantavirus |
| | | Luxi orthohantavirus |
| | | Maporal orthohantavirus |
| | | Montano orthohantavirus |
| | | Necocli orthohantavirus |
| | | Oxbow orthohantavirus |
| | | Prospect Hill orthohantavirus |
| | | Puumala orthohantavirus |
| | | Robina orthohantavirus |
| | | Rockport orthohantavirus |
| | | Sangassou orthohantavirus |
| | | Seewis orhtohantavirus |
| | | Seoul orthohantavirus |
| | | Sin Nombre orthohantavirus |
| | | Tatenale orthohantavirus |
| | | Thailand orthohantavirus |
| | | Tigray orthohantavirus |
| | | Tula orthohantavirus |
| | | Yakeshi orthohantavirus |
| | Orthopoxvirus | Abatino macacapox virus |
| | | Akhmeta virus |
| | | Alaskapox virus |
| | | Camelpox virus |
| | | Cowpox virus |
| | | Ectromelia virus |
| | | Monkeypox virus |
| | | Raccoonpox virus |
| | | Skunkpox virus |
| | | Taterapox virus |
| | | Variola virus |
| | | Volepox virus |
| | Lyssavirus | Aravan lyssavirus |
| | | Australian bat lyssavirus |
| | | Bokeloh bat lyssavirus |
| | | Duvenhage lyssavirus |
| | | European bat 1 lyssavirus |
| | | European bat 2 lyssavirus |
| | | Gannoruwa bat lyssavirus |
| | | Irkut lyssavirus |
| | | Khujand lyssavirus |
| | | Madagascar bat lyssavirus |
| | | Rabies lyssavirus |
| | | Lagos bat lyssavirus |
| | | Mokola lyssavirus |
| | | Shimoni bat lyssavirus |
| | | West Caucasian bat lyssavirus |
| | | Ikoma lyssavirus |
| | | Lleida bat lyssavirus |
| | Mammarenavirus | Lymphocytic choriomeningitis virus |
| | Mastadenovirus | Human adenovirus A |
| | | Human adenovirus B |
| | | Human adenovirus C |
| | | Human adenovirus D |
| | | Human adenovirus E |
| | | Human adenovirus F |
| | | Human adenovirus G |

In some embodiments, the antigen comprises a viral polypeptide. In some embodiments, the viral polypeptide comprises a coronavirus polypeptide described herein. In some embodiments, the coronavirus polypeptide comprises a SARS-CoV-2 polypeptide. In some embodiments, the SARS-Cov-2 polypeptide comprises a Spike protein or fragment thereof. In some embodiments, the Spike protein or fragment thereof is a full-length Spike protein. In some embodiments, the Spike protein or fragment thereof is a truncated Spike protein. In some embodiments, the truncated Spike protein comprises N-terminal domain of the Spike protein or S2 domain of the Spike protein. In some embodiments, the truncated Spike protein comprises N-terminal domain of the Spike protein and S2 domain of the Spike protein. In some embodiments, the Spike protein or fragment thereof is a recombinant Spike protein. In some embodiments, the Spike protein or fragment thereof comprises at least one modification. In some embodiments, the at least one modification comprises at least one amino acid mutation. In some embodiments, the at least one amino acid mutation eliminates a cleavage site such as a furin cleavage or serine protease cleavage site in the Spike protein. In some embodiments, the furin cleavage site comprises amino acid residues 682-685, amino acid residues 679-682, or amino acid residue 811 in SEQ ID NO: 21 (full-length Spike protein) or SEQ ID NO: 22 (Omicron mutant Spike protein).

In some embodiments, the serine protease cleavage site comprises amino acid residues 986 and 987; or 983 and 984 in SEQ ID NO: 21 (full-length Spike protein) or SEQ ID NO: 22 (Omicron mutant Spike protein). In some embodiments, the at least one amino acid mutation comprises amino acid substitution at amino acid residue 814, 889, 896, 939, 682-685, 679-682, 811, 986, 987, 983, 984, or a combination thereof in SEQ ID NO: 21 (full-length Spike protein) or SEQ ID NO: 22 (Omicron mutant Spike protein). In some embodiments, the at least one amino acid mutation comprises amino acid substitution at amino acid residue 814, 889, 896, and 939 in SEQ ID NO: 21 (full-length Spike protein) or SEQ ID NO: 22 (Omicron mutant Spike protein). In some embodiments, the Spike protein or fragment thereof comprises a signal peptide. In some embodiments, the signal peptide comprises an amino acid sequence of SEQ ID NO: 13: MDAMKRGLCCVLLLCGAVFVSASQEIHARFRR. In some embodiments, the signal peptide is a secretory peptide comprising an amino acid sequence that is at least 70%, at least 75%, at least 80%, at least 85%, at least 90%, at least 95%, or at least 99% identical to IgE Fc receptor alpha. In some embodiments, the secretory peptide is IgE Fc receptor alpha.

In some embodiments, the viral polypeptide comprises an influenza polypeptide. In some embodiments, the influenza polypeptide comprises an influenza A polypeptide, an influenza B polypeptide, an influenza C polypeptide, or an influenza D polypeptide. In some embodiments, the influenza polypeptide is the influenza A polypeptide. In some embodiments, the influenza A polypeptide comprises neuraminidase (NA) or fragment thereof or hemagglutinin (HA) or fragment thereof. In some embodiments, the influenza A polypeptide comprises the hemagglutinin (HA) or fragment thereof. In some embodiments, the hemagglutinin (HA) or fragment thereof is a full-length hemagglutinin (HA). In some embodiments, the hemagglutinin (HA) or fragment thereof is a truncated hemagglutinin (HA). In some embodiments, the truncated hemagglutinin (HA) comprises a Stalk domain. In some embodiments, the hemagglutinin (HA) or fragment thereof is a recombinant hemagglutinin (HA) comprising at least one modification. In some embodiments, the at least one modification comprises at least one amino acid mutation. In some embodiments, the at least one modification comprises the hemagglutinin (HA) or fragment thereof comprising an amino acid sequence of extracellular domain of M2 protein (M2e) of influenza A: SEQ ID NO: 14: MSLLTEVETPIRNEWGCRCNDSSD.

In some embodiments, the recombinant retroviral vector encodes at least one envelope protein. In some embodiments, the envelope encoded by the recombinant retroviral vector is an amphotropic envelope. In some embodiments, the recombinant retroviral vector encodes the at least one envelope protein for making the amphotropic envelope. In some embodiments, the at least one envelope protein comprises at least one alphavirus envelope protein. In some embodiments, at least one Sindbis virus envelope protein, where the at least one Sindbis virus envelope protein comprises E3 protein, E2 protein, 6K protein, E1 protein, or a combination thereof. In some embodiments, the at least one Sindbis virus envelope protein comprises at least one mutation. In some embodiments, the at least one mutation increases binding affinity between the at least one Sindbis virus envelope protein and a human cell such as a dendritic cell. In some embodiments, the at least one mutation is E160G of the E2 protein.

In some embodiments, the vector encodes a targeting moiety such as an antibody for targeting a cell surface marker (e.g., an antigen expressed on the cell surface of a cell associated with the disease or condition). In some embodiments, the cell surface marker is a tumor-associated antigen such as Her2. In some embodiments, the targeting moiety comprises an antibody, a nanobody (e.g., a single-chain variable fragment or scFv), or a combination thereof. In some embodiments, the targeting moiety is expressed on the surface of the viral envelope, where the vector described herein is encapsulated in the viral envelope. In some embodiments, the targeting moiety increases the targeting or delivering of the vector to the cell or microenvironment associated with the disease or condition such as cancer or lesion.

In some embodiments, the vector encodes a non-interleukin enzyme. In some aspects, the vector encodes an enzyme that can convert a nucleoside agent into a cytotoxic drug for killing a cell associated with the disease or condition described herein. In some embodiments, the enzyme comprises a kinase with nucleic acid nucleotide as a substrate. In some embodiments, the kinase is a thymidine kinase, where the thymidine kinase is salvage pathway enzyme which phosphorylates natural nucleoside substrates as well as nucleoside analogues. Generally, viral thymidine kinase can be exploited therapeutically by administration of a nucleoside analogue such as ganciclovir or acyclovir to a cell expressing viral thymidine kinase, wherein the viral thymidine kinase phosphorylates the nucleoside analogue, creating a toxic product capable of killing the cell. Viral thymidine kinase of the present disclosure can be prepared from a wide variety of viral thymidine kinases. In some embodiments, the viral thymidine kinase mutant is derived from Herpesviridae thymidine kinase including, for example, both primate herpes viruses, and non-primate herpes viruses such as avian herpes viruses. Representative examples of suitable herpes viruses include, for example, Herpes Simplex Virus (HSV) Type 1, Herpes Simplex Virus Type 2, Varicella zoster Virus, marmoset herpes virus, feline herpes virus type 1, pseudorabies virus, equine herpes virus type 1, bovine herpes virus type 1, turkey herpes virus, Marek's disease virus, herpesvirus saimiri, or Epstein-Barr virus.

In some aspects, the thymidine kinase described herein can be a mutant thymidine kinase, where the mutant thymidine kinase comprises at least one amino acid mutation. In some aspects, the mutant thymidine kinase is a mutant Herpes Simplex Virus type 1 thymidine kinase (HSV1-TK) comprising at least one amino acid mutation compared to wild-type amino acid sequence of HSV1-TK: MASYPGHQHASAFDQAARSRGHSNRRTALR-PRRQQEATEVRPEQKMPTLLRVYIDGPHGM GKTTTTQLLVALGSRDDIVYVPEPMTYWRVLGAS-ETIANIYTTQHRLDQGEISAGDAAVVM TSAQITMGMPYAVTDAVLAPHIGGEAGSSHAPPPAL- TLIFDRHPIAALLCYPAARYLMGSMT PQAVLAFVALIPPTLPGTNIVLGALPEDRHIDRLAKRQRPGERLDLAMLAAIRRVYGLLANT VRYLQCGGSWREDWGQL SGTAVPPQGAEPQ SNAGPRPHIGDTLFTLFRAPELLAPNGDLYN VFAWALDVLAKRLR (SEQ ID NO: 11). In some aspects, the mutant HSV1-TK comprises an amino acid sequence that is at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more sequence identity to the HSV1-TK amino acid sequence (e.g., SEQ ID NO: 11). In some embodiments, the mutant HSV-1-TK comprises a nuclear export sequence (NES). In some aspects, the NES comprises an amino acid sequence of LQKKLEELELDG (SEQ ID NO: 12).

Herpes viruses may be readily obtained from commercial sources such as the American Type Culture Collection ("ATCC", Rockville, Md.). Herpes viruses may also be isolated from naturally occurring courses (e.g., an infected animal).

In some embodiments, the mutant HSV1-TK comprises at least one amino acid mutation at amino acid residue 25, 26, 32, 33, 167, 168, or a combination thereof compared to the wild-type amino acid sequence of HSV1-TK (SEQ ID NO: 11). In some embodiments, the mutation comprises substituting a wild-type amino acid with a polar, non-polar, basic or acidic amino acid. In some embodiments, the mutant HSV1-TK is mutated at amino acid residues 167, 168, or both. In one example, the sequence is mutated at amino acid residue 167. In another example, the sequence is mutated at amino acid residue 168. In another example, the sequence is mutated at amino acid residues 167 and 168. Amino acid residue 167 may be mutated to histidine, lysine, cysteine, serine, and phenylalanine. Amino acid residue 168 may be mutated to histidine, lysine, cysteine, serine, or phenylalanine. In some embodiments, the mutant HSV1-TK is mutated at amino acid residues 25 and/or 26. In amino acid residues 25 and/or 26 may be mutated to an amino acid chosen from the group consisting of: glycine, serine, and glutamate. In some embodiments, the mutant HSV1-TK is mutated at amino acid residues 32 and/or 33. Amino acid residues 32 and/or 33 may be mutated to an amino acid chosen from the group consisting of: glycine, serine, cysteine, glutamic acid, and aspartic acid. In some embodiments, the mutant HSV1-TK is mutated at amino acid residues 25, 26, 32, and/or 33. Amino acid residues 25, 26, 32, and/or 33, may be mutated to an amino acid chosen from the group consisting of: glycine, serine, cysteine, glutamic acid, and aspartic acid.

In some embodiments, the mutant HSV1-TK is mutated at amino acid residue: 25 and/or 26; and 167, where the mutation at amino acid residue 25 and/or 26 comprises glycine, serine, cysteine, glutamic acid, or aspartic acid; and the mutation at amino acid residue 167 comprises histidine, lysine, cysteine, serine, or phenylalanine. In some embodiments, the mutant HSV1-TK is mutated at amino acid residue: 25 and/or 26; and 168, where the mutation at amino acid residue 25 and/or 26 comprises glycine, serine, cysteine, glutamic acid, or aspartic acid; and the mutation at amino acid residue 168 comprises histidine, lysine, cysteine, serine, or phenylalanine. In some embodiments, the mutant HSV1-TK is mutated at amino acid residue: 25 and/or 26; and 167 and/or 168, where the mutation at amino acid residue 25 and/or 26 comprises glycine, serine, cysteine, glutamic acid, or aspartic acid; and the mutation at amino acid residue 167 and/or 168 comprises histidine, lysine, cysteine, serine, or phenylalanine.

In some embodiments, the mutant HSV1-TK is mutated at amino acid residue: 32 and/or 33; and 167, where the mutation at amino acid residue 32 and/or 33 comprises glycine, serine, cysteine, glutamic acid, or aspartic acid; and the mutation at amino acid residue 167 comprises histidine, lysine, cysteine, serine, or phenylalanine. In some embodiments, the mutant HSV1-TK is mutated at amino acid residue: 32 and/or 33; and 168, where the mutation at amino acid residue 32 and/or 33 comprises glycine, serine, cysteine, glutamic acid, or aspartic acid; and the mutation at amino acid residue 168 comprises histidine, lysine, cysteine, serine, or phenylalanine. In some embodiments, the mutant HSV1-TK is mutated at amino acid residue: 32 and/or 33; and 167 and/or 168, where the mutation at amino acid residue 32 and/or 33 comprises glycine, serine, cysteine, glutamic acid, or aspartic acid; and the mutation at amino acid residue 167 and/or 168 comprises histidine, lysine, cysteine, serine, or phenylalanine.

In some embodiments, the mutant HSV1-TK is mutated at amino acid residue: 25, 26, 32, and 33; and 167, where the mutation at amino acid residue 25, 26, 32, and 33 comprises glycine, serine, cysteine, glutamic acid, or aspartic acid; and the mutation at amino acid residue 167 comprises histidine, lysine, cysteine, serine, or phenylalanine. In some embodiments, the mutant HSV1-TK is mutated at amino acid residue: 25, 26, 32, and 33; and 168, where the mutation at amino acid residue 25, 26, 32, and 33 comprises glycine, serine, cysteine, glutamic acid, or aspartic acid; and the mutation at amino acid residue 168 comprises histidine, lysine, cysteine, serine, or phenylalanine. In some embodiments, the mutant HSV1-TK is mutated at amino acid residue: 25, 26, 32, and 33; and 167 and/or 168, where the mutation at amino acid residue 25, 26, 32, and 33 comprises glycine, serine, cysteine, glutamic acid, or aspartic acid; and the mutation at amino acid residue 167 and/or 168 comprises histidine, lysine, cysteine, serine, or phenylalanine.

In some embodiments, the mutant HSV1-TK is mutated at amino acid residue: 25 and 26 or 32 and 33; and 167, where the mutation at amino acid residue 25 and 26 or 32 and 33 comprises glycine, serine, cysteine, glutamic acid, or aspartic acid; and the mutation at amino acid residue 167 comprises histidine, lysine, cysteine, serine, or phenylalanine. In some embodiments, the mutant HSV1-TK is mutated at amino acid residue: 25 and 26 or 32 and 33; and 168, where the mutation at amino acid residue 25 and 26 or 32 and 33 comprises glycine, serine, cysteine, glutamic acid, or aspartic acid; and the mutation at amino acid residue 168 comprises histidine, lysine, cysteine, serine, or phenylalanine. In some embodiments, the mutant HSV1-TK is mutated at amino acid residue: 25 and 26 or 32 and 33; and 167 and/or 168, where the mutation at amino acid residue 25 and 26 or 32 and 33 comprises glycine, serine, cysteine, glutamic acid, or aspartic acid; and the mutation at amino acid residue 167 and/or 168 comprises histidine, lysine, cysteine, serine, or phenylalanine.

In some embodiments, the mutant HSV1-TK is mutated at amino acid residue: any one or more of 25, 26, 32 and/or 33; and 167, where the mutation at amino acid residue any one or more of 25, 26, 32 and/or 33 comprises glycine, serine, cysteine, glutamic acid, or aspartic acid; and the mutation at amino acid residue 167 comprises histidine, lysine, cysteine, serine, or phenylalanine. In some embodiments, the mutant HSV1-TK is mutated at amino acid residue: any one or more of 25, 26, 32 and/or 33; and 168, where the mutation at amino acid residue any one or more of 25, 26, 32 and/or 33 comprises glycine, serine, cysteine, glutamic acid, or aspartic acid; and the mutation at amino acid residue 168 comprises histidine, lysine, cysteine, serine, or phenylalanine. In some embodiments, the mutant HSV1-TK is mutated at amino acid residue: any one or more of 25, 26, 32 and/or 33; and 167 and/or 168, where the mutation at amino acid residue any one or more of 25, 26, 32 and/or 33 comprises glycine, serine, cysteine, glutamic acid, or aspartic acid; and the mutation at amino acid residue 167 and/or 168 comprises histidine, lysine, cysteine, serine, or phenylalanine.

In some embodiments, the vector, in addition to encoding mutant HSV1-TK, can encode PiT-2, PiT-1, mCat-1 (murine cationic receptor-1; target of ecotropic Moloney MLV), or other receptors used by gamma retroviruses.

In some embodiments, the mutant HSV1-TK, compared to wild-type HSV1-TK, comprises increased enzymatic activity of converting a nucleoside agent into a cytotoxic drug. In some embodiments, the mutant HSV1-TK increases enzymatic activity of converting a nucleoside agent into a cytotoxic drug by at least 0.1 fold, 0.2 fold, 0.3 fold, 0.4 fold, 0.5 fold, 1.0 fold, 2.0 fold, 5.0 fold, 10.0 fold, or more compared to the enzymatic activity of a wild-type HSV1-TK converting the same nucleoside agent (e.g., a prodrug) into the cytotoxic drug.

In some embodiments, the mutant HSV1-TK increases bystander effect of cells capable of this phenomenon for killing the cell associated with the disease or condition. As used herein, the "bystander effect" refers to the phenomenon by which a HSV1-TK positive cell (e.g., cell contacted with vector described herein) exerts a kill effect on neighboring HSV1-TK negative cells following induction of HSV1-TK expression in the HSV1-TK positive cells. In some embodiments, the mutant HSV1-TK increases the bystander effect by at least 0.1 fold, 0.2 fold, 0.3 fold, 0.4 fold, 0.5 fold, 1.0 fold, 2.0 fold, 5.0 fold, 10.0 fold, or more compared to the bystander effect induced by a wild-type HSV1-TK positive cell.

Vaccination

Described herein, in some embodiments, is a vector (e.g., a recombinant viral vector) comprising a mutant integrase described herein. In some embodiments, the mutant integrase prevents the insertion of the vector into the genome of the host cell comprising the vector. In some embodiments, the vector comprises a mutant reverse transcriptase, wherein the mutant reverse transcriptase prevents converting of the vector into DNA for insertion into the genome of the cell. In some embodiments, the vector comprises both the mutant integrase and the mutant reverse transcriptase. Such vectors comprising mutant integrase and/or mutant reverse transcriptase can be particularly useful for vaccinating a subject in need thereof, where an antigen encoded by the vector can be expressed into the subject for a prolonged period of time. The prolonged expression of the antigen can induce sufficient immune response against the antigen, thus vaccinating the subject against a disease or condition. In some embodiments, the expression of the antigen can be inducible, where the antigen is only expressed (thereby vaccinating the subject) when needed. For example, the expression of the antigen can be induced when the immunity against the antigen is waning, creating a booster vaccination.

In some cases, the antigen can include a polypeptide sequence of a viral protein. In some embodiments, the antigen may be a viral protein of a coronavirus. In some embodiments, the coronavirus may be severe acute respiratory syndrome-related virus (SARS-CoV). In some embodiments, the SARS-CoV is SARS-CoV-2. In some embodiments, the epitope may be a viral protein selected from ORF1a, ORF1ab, Spike protein (S protein), 3a, 3b, envelope protein (E protein), matrix protein (M protein), p6, 7a, 7b, 8b, 9b, nucleocapsid protein (N protein), ORF14, Nsp1 (leader protein), Nsp2, Nsp3, Nsp4, Nsp5 (3C-like proteinase), Nsp6, Nsp7, Nsp8, Nsp9, Nsp10 (growth-factor-like protein), Nsp12 (RNA-dependent RNA polymerase, or RdRp), Nsp13 (RNA 5'-triphosphatase), Nsp14 (3'-to-5' exonuclease), Nsp15 (endoRNAse), and Nsp16 (2'-O-ribose methyltransferase), a portion thereof, or combinations thereof.

In some embodiments, the antigen can include a polypeptide sequence of a viral protein of an influenza virus. In some embodiments, the influenza virus is selected from the genera consisting of Influenza virus A, Influenza virus B, Influenza virus C and Influenza virus D. In further embodiments, the influenza A virus is of the subtype H1N1, H2N2, H3N2, H5N1, H7N7, H1N2, H9N2, H7N2, H7N3, H10N7, H7N9, or H6N1. In further embodiments, the influenza virus comprises influenza B virus of the B/Yamagata/16/88-like lineage or the B/Victoria/2/87-like lineage. In further embodiments, the influenza virus comprises influenza A virus of the A/California/04/2009-like lineage or the A/Brisbane/59/2007-like lineage. In some embodiments, the influenza may be any strain of the influenza virus or any serotypes within a stain of influenza virus. In some cases, the influenza virus comprises any combination viral surface glycoproteins haemagglutinin (H or HA) and neuraminidase (N or NA). In some embodiments, the antigen comprises modified influenza protein comprising hemagglutinin (HA) Stalk (conserved region) domain. In some embodiments, the HA stalk comprises at least one modification. Non-limiting examples of the HA stalk modification can include head removal; glycine linker loop; intra-Cys bridge; transmembrane removal; loop fusion peptide; GCN4 position; or inter-Cys bridge. In some embodiments, the antigen comprises Extracellular domain of the M2 protein (M2e) of influenza A has an amino acid sequence of: MSLLTEVETPIRNEWGCRCNDSSD (SEQ ID NO: 14).

In some embodiments, the antigen can include a polypeptide sequence of a pathogen protein such as other viral protein, bacterial protein, parasite protein, fungus protein, or a combination thereof. In some embodiments, the antigen can include a tumor antigen such as Her2, where the subject is subsequently immunized against cancer.

Method of Treatment

Disclosed herein, in some embodiments, are methods of using the vector described herein. In some embodiments, the method comprises treating a disease or condition in a subject in need thereof by administering a vector or pharmaceutical composition comprising the vector described herein to the subject. In some embodiments, the method comprises contacting a cell with the vector and subsequently administering the cell to the subject. In some embodiments, the cell contacted with the vector is an autologous cell. For example, the cell can be first isolated from the subject and optionally cultured or expanded prior to being contacted with the vector. In some embodiments, expression of the interleukin (e.g., P40 or P35 of IL-12, IL-7, or interferon) or HSV1-TK encoded by the vector can be verified in the cell prior to administering the cell to the subject.

In some embodiments, the method comprises administering two or more vectors to the subject, where a first of the two or more vectors encode an interleukin (e.g., P40 or P35 of IL-12, IL-7, or interferon) described herein and a second of the two or more vectors encode a thymidine kinase (e.g., the mutated HSV1-TK) described herein. In some embodiments, the method comprises first contacting a cell with the two or more vectors and subsequently administering the cell of the subject. In embodiments, the interleukin (e.g., P40 or P35 of IL-12, IL-7, or interferon) and the thymidine kinase (e.g., the mutated HSV1-TK) are encoded by the same vector. In some embodiments, administration is by any suitable mode of administration, including systemic administration (e.g., intravenous, inhalation, etc.). In some embodiments, the subject is human. In some embodiments, the disease or condition is cancer or lesion. In some embodiments, the disease or condition is metabolic disease.

In some embodiments, the vector, the cell comprising the vector, the recombinant virus encoded by the vector, or the pharmaceutical composition delivers an interleukin to a cell or microenvironment associated with the disease or condition. In some embodiments, the vector, the cell comprising the vector, the recombinant virus encoded by the vector, or the pharmaceutical composition delivering the interleukin decreases toxicity (e.g., as determined by decreased cell death of cells not associated with the disease or condition or decreased expression of hot tumor genes) in the subject compared to direct administration of interleukin to the subject. In some embodiments, the toxicity of delivering the interleukin by the vector, the cell comprising the vector, the recombinant virus encoded by the vector, or the pharmaceutical composition described herein is decreased by at least 0.1 fold, 0.2 fold, 0.5 fold, 1.0 fold, 2.0 fold, 5.0 fold, 10.0 fold, 50.0 fold, or more compared to toxicity induced by directly administering the interleukin to the subject.

In some embodiments, the vector, the cell comprising the vector, the recombinant virus encoded by the vector, or the pharmaceutical composition delivers an IL-12 to a cell or microenvironment associated with the disease or condition. In some embodiments, the vector, the cell comprising the vector, the recombinant virus encoded by the vector, or the pharmaceutical composition delivering the IL-12 (either as P40 subunit and P35 subunit or as a recombinant IL-12) decreases toxicity (e.g., as determined by decreased cell death of cells not associated with the disease or condition or decreased expression of hot tumor genes) in the subject compared to direct administration of IL-12 to the subject. In some embodiments, the toxicity of delivering the IL-12 by the vector, the cell comprising the vector, the recombinant virus encoded by the vector, or the pharmaceutical composition described herein is decreased by at least 0.1 fold, 0.2 fold, 0.5 fold, 1.0 fold, 2.0 fold, 5.0 fold, 10.0 fold, 50.0 fold, or more compared to toxicity induced by directly administering the IL-12 to the subject.

In some embodiments, the IL-12 encoded by the vector is expressed or secreted by the cell. In some embodiments, the IL-12 expressed or secreted by the cell can stimulate innate immune signaling or response in the subject. In some embodiments, the method comprises stimulating the production of endogenous cytokines (e.g., IFN-7) with the expressed or secreted interleukin (e.g., P40 or P35 of IL-12) for treating the disease or condition. Hot tumor gene expression can refer to expression of gene products such as the cytokines described herein that triggers endogenous immune response. As such, the expression of the hot tumor gene can lead to killing of the cell (e.g., a cancer or a tumor cell) associated with the disease or condition by the endogenous immune response.

In some embodiments, the vector, the cell comprising the vector, the recombinant virus encoded by the vector, or the pharmaceutical composition delivering the interleukin increases efficacy for treating the disease or condition (e.g., as determined by increased cell death of tumor cells or increased expression of hot tumor genes) in the subject compared to direct administration of interleukin to the subject. In some embodiments, the efficacy for treating the disease or condition by delivering the interleukin by the vector, the cell comprising the vector, the recombinant virus encoded by the vector, or the pharmaceutical composition described herein is decreased by at least 0.1 fold, 0.2 fold, 0.5 fold, 1.0 fold, 2.0 fold, 5.0 fold, 10.0 fold, 50.0 fold, or more compared to efficacy for treating the disease or condition by directly administering the interleukin to the subject.

In some embodiments, the vector, the cell comprising the vector, the recombinant virus encoded by the vector, or the pharmaceutical composition delivering the IL-12 (either as P40 subunit and P35 subunit or as a recombinant IL-12) increases efficacy for treating the disease or condition (e.g., as determined by increased cell death of tumor cells or increased expression of hot tumor genes) in the subject compared to direct administration of IL-12 to the subject. In some embodiments, the efficacy for treating the disease or condition by delivering the IL-12 by the vector, the cell comprising the vector, the recombinant virus encoded by the vector, or the pharmaceutical composition described herein is decreased by at least 0.1 fold, 0.2 fold, 0.5 fold, 1.0 fold, 2.0 fold, 5.0 fold, 10.0 fold, 50.0 fold, or more compared to efficacy for treating the disease or condition by directly administering the IL-12 to the subject.

In some embodiments, the vector, the cell comprising the vector, the recombinant virus encoded by the vector, or the pharmaceutical composition is administered at least once during a period of time (e.g., every 2 days, twice a week, once a week, every week, three times per month, two times per month, one time per month, every 2 months, every 3 months, every 4 months, every 5 months, every 6 months, every 7 months, every 8 months, every 9 months, every 10 months, every 11 months, once a year). In some embodiments, the composition is administered two or more times (e.g., 2, 3, 4, 5, 6, 7, 8, 9, 10, 11, 12, 13, 14, 15, 16, 17, 18, 19, 20, 30, 40, 50, 60, 70, 80, 90, 100 times) during a period of time.

Described herein, in some aspects, is a method of treating or preventing a disease or condition in a subject by vaccinating the subject, the method comprising administering to the subject a recombinant retroviral vector described herein, a recombinant virus encoded by the retroviral vector described herein, the cell transduced by the retroviral vector described herein, or the pharmaceutical composition described herein. In some embodiments, the at least one payload encoded by the retroviral vector comprises an antigen that induces immune response in the subject, thereby treating or preventing the disease or condition in the subject by vaccinating the subject. In some embodiments, the immune response comprises induction of neutralizing antibody targeting the antigen, thereby generating immunity against the antigen in the subject. In some embodiments, the immune response comprises induction of immunoglobulin antibody targeting the antigen, thereby generating immunity against the antigen in the subject. In some embodiments, the immunoglobulin antibody comprises IgG antibody, IgM antibody, IgA antibody, IgD antibody, IgE antibody, or a combination thereof. In some embodiments, the immunoglobulin antibody comprises IgG antibody.

In some embodiments, the at least one payload is expressed and secreted in the subject for at least 12 hours, at least one day, at least two days, at least three days, at least four days, at least five days, at least six days, at least seven days, at least eight days, at least nine days, at least 10 days, at least 11 days, at least 12 days, or for a longer duration. In some embodiments, the at least one payload is expressed or secreted in the subject for at least 12 hours, at least one day, at least two days, at least three days, at least four days, at least five days, at least six days, at least seven days, at least eight days, at least nine days, at least 10 days, at least 11 days, at least 12 days, or for a longer duration. In some embodiments, a duration of the immune response induced by the at least one payload expressed or secreted for at least 12 hours is increased by at least 10%, at least 20%, at least 50%, at least 100%, at least 5 fold, at least 10 fold, or more compared to a duration of an immune response induced by a comparable payload that is expressed or secreted for fewer than 12 hours. In some embodiments, a duration of the immune response induced by the at least one payload expressed or secreted for at least one day is increased by at least 10%, at least 20%, at least 50%, at least 100%, at least 5 fold, at least 10 fold, or more compared to a duration of an immune response induced by a comparable payload that is expressed or secreted for fewer than one day. In some embodiments, a duration of the immune response induced by the at least one payload expressed or secreted for at least two days is increased by at least 10%, at least 20%, at least 50%, at least 100%, at least 5 fold, at least 10 fold, or more compared to a duration of an immune response induced by a comparable payload that is expressed or secreted for fewer than two days. In some embodiments, a duration of the immune response induced by the at least one payload expressed or secreted for at least three days is increased by at least 10%, at least 20%, at least 50%, at least 100%, at least 5 fold, at least 10 fold, or more compared to a duration of an immune response induced by a comparable payload that is expressed or secreted for fewer than three days. In some embodiments, a duration of the immune response induced by the at least one payload expressed or secreted for at least four days is increased by at least 10%, at least 20%, at least 50%, at least 100%, at least 5 fold, at least 10 fold, or more compared to a duration of an immune response induced by a comparable payload that is expressed or secreted for fewer than four days. In some embodiments, a duration of the immune response induced by the at least one payload expressed or secreted for at least five days is increased by at least 10%, at least 20%, at least 50%, at least 100%, at least 5 fold, at least 10 fold, or more compared to a duration of an immune response induced by a comparable payload that is expressed or secreted for fewer than five days. In some embodiments, a duration of the immune response induced by the at least one payload expressed or secreted for at least five days is increased by at least 10%, at least 20%, at least 50%, at least 100%, at least 5 fold, at least 10 fold, or more compared to a duration of an immune response induced by a comparable payload that is expressed or secreted for fewer than six days. In some embodiments, a duration of the immune response induced by the at least one payload expressed or secreted for at least seven days is increased by at least 10%, at least 20%, at least 50%, at least 100%, at least 5 fold, at least 10 fold, or more compared to a duration of an immune response induced by a comparable payload that is expressed or secreted for fewer than seven days. In some embodiments, a duration of the immune response induced by the at least one payload expressed or secreted for at least eight days is increased by at least 10%, at least 20%, at least 50%, at least 100%, at least 5 fold, at least 10 fold, or more compared to a duration of an immune response induced by a comparable payload that is expressed or secreted for fewer than eight days. In some embodiments, a duration of the immune response induced by the at least one payload expressed or secreted for at least eight days is increased by at least 10%, at least 20%, at least 50%, at least 100%, at least 5 fold, at least 10 fold, or more compared to a duration of an immune response induced by a comparable payload that is expressed or secreted for fewer than nine days. In some embodiments, the immune response persists in the subject for at least one month, at least two months, at least three months, at least four months, at least five months, at least six months, at least 12 months, at least two years, at least three years or longer.

In some embodiments, the vector, the cell comprising the vector, the recombinant virus encoded by the vector, or the pharmaceutical composition is administered in a therapeutically-effective amount by various forms and routes including, for example, oral, or topical administration. In some embodiments, the vector, the cell comprising the vector, the recombinant virus encoded by the vector, or the pharmaceutical composition may be administered by bronchial lavage, sublingual, intratumoral, parenteral, intravenous, subcutaneous, intramuscular, intradermal, intraperitoneal, intracerebral, subarachnoid, intraocular, intrasternal, ophthalmic, endothelial, local, intranasal, intrapulmonary, rectal, intraarterial, intrathecal, inhalation, intralesional, intradermal, epidural, intracapsular, subcapsular, intracardiac, transtracheal, subcuticular, or intraspinal administration, e.g., injection or infusion. In some embodiments, a composition may be administered by absorption through epithelial or mucocutaneous linings (e.g., oral mucosa, rectal and intestinal mucosa administration). In some embodiments, the vector, the cell comprising the vector, the recombinant virus encoded by the vector, or the pharmaceutical composition is delivered via multiple administration routes.

In some embodiments, the vector, the cell comprising the vector, the recombinant virus encoded by the vector, or the pharmaceutical composition is administered by intravenous infusion. In some embodiments, the vector, the cell comprising the vector, the recombinant virus encoded by the vector, or the pharmaceutical composition comprising the vector is administered by slow continuous infusion over a long period, such as more than 24 hours. In some aspects, the vector, the cell comprising the vector, the recombinant virus encoded by the vector, or the pharmaceutical composition can be administered in a local manner, for example, via injection of the agent directly into an organ, optionally in a depot or sustained release formulation or implant.

In some embodiments, the method comprises monitoring expression of interleukin such as IL-12 in the subject after the subject has been treated. In some aspects, the method comprises monitoring the expression level of IL-12, where, if the IL-12 expression reaches a predetermined threshold in the subject, an interleukin inhibitor can be administered to the subject.

In some embodiments, the vector, the cell comprising the vector, the recombinant virus encoded by the vector, or the pharmaceutical composition provided herein can be administered in conjunction with at least one additional therapeutic, for example, an antiviral therapy, a chemotherapy, an antibiotic, a cell therapy, a cytokine therapy, or an anti-inflammatory agent. In some embodiments, the at least one additional therapeutic comprises a nucleoside agent (e.g., a prodrug). Non-limiting example of the prodrug can include FHBG (9-[4-fluoro-3-(hydroxymethyl)butyl]guanine), FHPG (9-([3-fluoro-1-hydroxy-2-propoxy]methyl)guanine), FGCV (fluoroganciclovir), FPCV (fluoropenciclovir), FIAU (1-(2'-deoxy-2'-fluoro-1-β-D-arabinofuranosyl)-5-iodouracil), FEAU (fluoro-5-ethyl-1-beta-D-arabinofuranosyluracil), FMAU (fluoro-5-methyl-1-beta-D-arabinofuranosyluracil), FHOMP (6-((1-fluoro-3-hydroxypropan-2-yloxy)methyl)-5-methylpryrimidine-2,4(1H,3H)-dione), ganciclovir, valganciclovir, acyclovir, valacivlovir, penciclovir, radiolabeled pyrimidine with 4-hydroxy-3-(hydroxymethyl)butyl side chain at N-1 (HHG-5-FEP) or 5-(2-) hydroxyethyl)- and 5-(3-hydroxypropyl)-substituted pyrimidine derivatives bearing 2,3-dihydroxypropyl, acyclovir-, ganciclovir- and penciclovir-like side chains for thymidine kinase; ifosfamide for oxidoreductase; 6-methoxypurine arabinoside for VZV-TK; 5-fluorocytosine for cytosine deaminase; doxorubicin for beta-glucuronidase; CB1954 for nitroreductase; and N-(Cyanoacetyl)-L-phenylalanine, or N-(3-chloropropionyl)-L-phenylalanine for carboxypeptidase A. In some embodiments, the nucleoside agent comprises ganciclovir, valganciclovir, acyclovir, valacyclovir, or penciclovir.

In some embodiments, the vector, the cell comprising the vector, the recombinant virus encoded by the vector, or the pharmaceutical composition provided herein can be administered before, during, or after occurrence of the disease or condition. In some embodiments, the vector, the cell comprising the vector, the recombinant virus encoded by the vector, or the pharmaceutical composition can be used as a prophylactic and may be administered continuously to subjects. In some embodiments, the vector, the cell comprising the vector, the recombinant virus encoded by the vector, or the pharmaceutical composition can be administered to a subject before the onset of the symptoms associated with the disease or condition.

Actual dosage levels of an agent of the disclosure (e.g., the vector, the cell comprising the vector, the recombinant virus encoded by the vector, or the pharmaceutical composition) can be varied so as to obtain an amount of the agent to achieve the desired therapeutic response for a particular subject, composition, and mode of administration, without being toxic to the subject (e.g., the subject for immunization or the subject for treatment). The selected dosage level may depend upon a variety of pharmacokinetic factors including the activity of the particular compositions of the present invention employed, the route of administration, the time of administration, the rate of excretion, the duration of the treatment, other drugs, compounds and/or materials used in combination with the particular compositions employed, the age, sex, weight, condition, general health and prior medical history of the patient being treated, and like factors well known in the medical arts.

Dosage regimens may be adjusted to provide the optimum desired response (e.g., a therapeutic and/or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects (e.g., the subjects for immunization or the subjects for treatment); each unit contains a predetermined quantity of active agent calculated to produce the desired therapeutic effect in association with the required pharmaceutical carrier. The specification for the dosage unit forms of the disclosure may be determined by and directly dependent on (a) the unique characteristics of the active agent and the particular therapeutic effect to be achieved, and (b) the limitations inherent in the art of compounding such an active agent for the treatment of sensitivity in individuals. A dose may be determined by reference to a plasma concentration or a local concentration of the circular polyribonucleotide or antibody or antigen-binding fragment thereof. A dose may be determined by reference to a plasma concentration or a local concentration of the linear polyribonucleotide or antibody or antigen-binding fragment thereof.

In some embodiments, the vector, the cell comprising the vector, the recombinant virus encoded by the vector, or the pharmaceutical composition described herein can be in a unit dosage form suitable for a single administration of a precise dosage. In unit dosage form, the formulation may be divided into unit doses containing appropriate quantities of the compositions. In unit dosage form, the formulation may be divided into unit doses containing appropriate quantities of one or more linear polyribonucleotides, antibodies or the antigen-binding fragments thereof, and/or therapeutic agents. The unit dosage may be in the form of a package containing discrete quantities of the formulation. Non-limiting examples are packaged injectables, vials, and ampoules. An aqueous suspension composition disclosed herein may be packaged in a single-dose non-reclosable container. Multiple-dose reclosable containers may be used, for example, in combination with or without a preservative. A formulation for injection disclosed herein may be present in a unit dosage form, for example, in ampoules, or in multi dose containers with a preservative.

The dosage of the vector, the cell comprising the vector, the recombinant virus encoded by the vector, or the pharmaceutical composition lies preferably within a range of circulating concentrations that include the ED50 with little or no toxicity. The dosage may vary within this range depending upon the dosage form employed and the route of administration utilized. A therapeutically effective dose can be estimated initially from cell culture assays. A dose may be formulated in animal models to achieve a circulating plasma concentration range that includes the IC50 (i.e., the concentration of the test compound which achieves a half-maximal infection or a half-maximal inhibition) as determined in cell culture. Such information can be used to determine useful doses more accurately in humans. Levels in plasma may be measured, for example, by RT-qPCR or ddPCR methods.

An effective amount or therapeutically effective of the vector, the cell comprising the vector, the recombinant virus encoded by the vector, or the pharmaceutical composition disclosed herein to be administered to a subject in need of treatment may be determined in a variety of ways. By way of example, the amount may be based on viral titer or efficacy in an animal model. Alternatively, the dosing regimens used in clinical trials may be used as general guidelines.

In some embodiments, the daily dose may be administered in a single dose or in portions at various hours of the day. In some embodiments, a higher dosage may be required and may be reduced over time when the optimal initial response is obtained. In some embodiments, treatment may be continuous for days, weeks, or years, or may be at intervals with intervening rest periods. In some embodiments, the dosage is modified in accordance with other treatments the individual may be receiving. However, the method of treatment is in no way limited to a particular concentration or range of the retroviral particle and may be varied for each individual being treated and for each derivative used. Individualization of dosage may be required to achieve the maximum effect for a given individual. In some embodiments, the dosage administered to an individual being treated varies depending on the individual's age, severity or stage of the disease and response to the course of treatment. In some embodiments, clinical parameters for determining dosage include, but are not limited to, tumor size, alteration in the level of tumor markers used in clinical testing for particular malignancies. In some embodiments, the treating physician determines the therapeutically effective amount to be used for a given individual. In some embodiments, the therapies disclosed herein are administered as often as necessary and for the period of time judged necessary by the treating physician.

In some embodiments, multiple therapeutic courses (e.g., first and second therapeutic course) are administered to a subject in need of treatment. In some embodiments, the first and/or second therapeutic course is administered intravenously. In other embodiments, the first and/or second therapeutic course is administered via intra-arterial infusion, including but not limited to infusion through the hepatic artery, cerebral artery, coronary artery, pulmonary artery, iliac artery, celiac trunk, gastric artery, splenic artery, renal artery, gonadal artery, subclavian artery, vertebral artery, axillary artery, brachial artery, radial artery, ulnar artery, carotid artery, femoral artery, inferior mesenteric artery and/or superior mesenteric artery. Intra-arterial infusion may be accomplished using endovascular procedures, percutaneous procedures or open surgical approaches. In some embodiments, the first and second therapeutic course may be administered sequentially. In yet other embodiments, the first and second therapeutic course may be administered simultaneously. In still other embodiments, the optional third therapeutic course may be administered sequentially or simultaneously with the first and second therapeutic courses.

In some embodiments, the vector, the cell comprising the vector, the recombinant virus encoded by the vector, or the pharmaceutical composition disclosed herein may be administered in conjunction with a sequential or concurrently administered therapeutic course(s) in high doses on a cumulative basis. For example, in some embodiments, a patient in need thereof may be systemically administered, e.g., intravenously administered, with a therapeutic course on a cumulative basis. A first therapeutic course may be systemically administered. Alternatively, the first therapeutic course may be administered in a localized manner, e.g., intra-arterially, for example a patient in need thereof may be administered via intra-arterial infusion on a cumulative basis.

In yet other embodiments, a subject in need thereof may receive a combination, either sequentially or concurrently, of systemic and intra-arterial infusions administration of high doses of the vector, the cell comprising the vector, the recombinant virus encoded by the vector, or the pharmaceutical composition. For example, a patient in need thereof may be first systemically administered with the vector, the cell comprising the vector, the recombinant virus encoded by the vector, or the pharmaceutical composition on a cumulative basis, followed by an additional therapeutic course of intra-arterial infusion, e.g., hepatic arterial infusion, administered delivery on a cumulative basis.

A subject in need of treatment may also be administered, either systemically or localized (for example intra-arterial infusion, such as hepatic arterial infusion) a therapeutic course of delivering the vector, the cell comprising the vector, the recombinant virus encoded by the vector, or the pharmaceutical composition for a defined period of time. In some embodiments, the period of time may be at least one day, at least two days, at least three days, at least four days, at least five days, at least six days, at least seven days, at least one week, at least two weeks, at least three weeks, at least four weeks, at least five weeks, at least six weeks, at least seven weeks, at least eight weeks, at least 2 months, at least three months, at least four months, at least five months, at least six months, at least seven months, at least eight months, at least nine months, at least ten months, at least eleven months, at least one year, at least two years, at least three years, at least four years, or at least five years. Administration could also take place in a chronic manner, i.e., for an undefined or indefinite period of time.

Administration of the vector, the cell comprising the vector, the recombinant virus encoded by the vector, or the pharmaceutical composition may also occur in a periodic manner, e.g., at least once a day, at least twice a day, at least three times a day, at least four times a day, at least five times a day. Periodic administration of the delivery of the vector, the cell comprising the vector, the recombinant virus encoded by the vector, or the pharmaceutical composition may be dependent upon the time of delivery as well as the mode of administration. For example, parenteral administration may take place only once a day over an extended period of time, whereas oral administration of the delivery of the vector, the cell comprising the vector, the recombinant virus encoded by the vector, or the pharmaceutical composition may take place more than once a day wherein administration of the delivery of the vector, the cell comprising the vector, the recombinant virus encoded by the vector, or the pharmaceutical composition takes place over a shorter period of time.

In one embodiment, the subject is allowed to rest 1 to 2 days between the first therapeutic course and second therapeutic course. In some embodiments, the subject is allowed to rest 2 to 4 days between the first therapeutic course and second therapeutic course. In other embodiments, the subject is allowed to rest at least 2 days between the first and second therapeutic course. In yet other embodiments, the subject is allowed to rest at least 4 days between the first and second therapeutic course. In still other embodiments, the subject is allowed to rest at least 6 days between the first and second therapeutic course. In some embodiments, the subject is allowed to rest at least 1 week between the first and second therapeutic course. In yet other embodiments, the subject is allowed to rest at least 2 weeks between the first and second therapeutic course. In one embodiment, the subject is allowed to rest at least one month between the first and second therapeutic course. In some embodiments, the subject is allowed to rest at least 1-7 days between the second therapeutic course and the optional third therapeutic course. In yet other embodiments, the subject is allowed to rest at least 1-2 weeks between the second therapeutic course and the optional third therapeutic course.

In some embodiments, the vector, the cell comprising the vector, the recombinant virus encoded by the vector, or the pharmaceutical composition is administered to increase local concentration of an interleukin (e.g., P40 or P35 of IL-12) and a thymidine kinase (e.g., the mutated HSV1-TK) in the cell or the microenvironment associated with the disease or condition (e.g., cancer or lesion) described herein. In some embodiments, the vector, the cell comprising the vector, the recombinant virus encoded by the vector, or the pharmaceutical composition is administered via intra-arterial infusion, which increases local concentration of the therapeutic vector to a specific organ system. In yet other embodiments, the vector, the cell comprising the vector, the recombinant virus encoded by the vector, or the pharmaceutical composition is administered intratumorally. Dependent upon the location of the target lesions, in some embodiments, catheterization of the hepatic artery is followed by infusion into the pancreaticoduodenal, right hepatic, and middle hepatic artery, respectively, in order to locally target hepatic lesions. In some embodiments, localized distribution to other organ systems, including the lung, gastrointestinal, brain, reproductive, splenic or other defined organ system, of the polypeptide or delivery vector is accomplished via catheterization or other localized delivery system. In some embodiments, intra-arterial infusions are accomplished via any other available arterial source, including but not limited to infusion through the hepatic artery, cerebral artery, coronary artery, pulmonary artery, iliac artery, celiac trunk, gastric artery, splenic artery, renal artery, gonadal artery, subclavian artery, vertebral artery, axillary artery, brachial artery, radial artery, ulnar artery, carotid artery, femoral artery, inferior mesenteric artery and/or superior mesenteric artery. In some embodiments, intra-arterial infusion is accomplished using endovascular procedures, percutaneous procedures or open surgical approaches.

Pharmaceutical Composition

Described herein is a pharmaceutical composition comprising a therapeutic agent (e.g., the vector or the cell comprising the vector described herein) or an antigen for vaccinating a subject. In some aspects, the cell contacted with the vector described herein expresses an interleukin (e.g., P40 or P35 of IL-12), a thymidine kinase (e.g., the mutated HSV1-TK), or an antigen described herein in vivo or in vitro. In some aspects, the cell is: obtained from a subject; expanded in an in vitro environment; and administer back to the subject for treating the disease or condition in the subject or vaccinating the subject. In some embodiments, at least one vector or cell contacted with the at least one vector described herein can be formulated into a vaccine. In some embodiments, the at least one vector described herein is formulated into an RNA vaccine. In some embodiments, the at least one vector described is formulated into a mRNA vaccine, where the antigen is encoded by mRNA as the payload of the vector. In some embodiments, the pharmaceutical composition comprises a recombinant virus encoded by a vector described herein. For example, the pharmaceutical composition can comprise a modified Sindbis virus for targeting dendritic cells. In some embodiments, the vaccine comprises at least two vectors described herein, where the at least two vectors can encode different payloads. In some embodiments, the vector comprises the mutant integrase described herein, where the vector can no longer be inserted into the genome of the cell. In some embodiments, the vector comprises the mutant reverse transcriptase, where the nucleic acid (e.g., RNA) of the vector can no longer be converted into DNA and subsequently inserted into the genome of the cell. In some embodiments, the vector comprises both the mutant integrase and the mutant reverse transcriptase. In some aspects, the cell is obtained from a source that is not from the subject. In some aspect, the cell is obtained from a cell line. In some embodiments, the cell is formulated into the pharmaceutical composition. In some embodiments, the pharmaceutical composition comprises a nucleoside agent described herein.

In some aspects, the pharmaceutical composition comprises a pharmaceutically acceptable: carrier, excipient, or diluent. In some aspects, the pharmaceutical composition described herein includes at least one additional active agent other than the cell described herein. In some aspects, the at least one additional active agent is a chemotherapeutic agent, cytotoxic agent, cytokine, growth-inhibitory agent, anti-hormonal agent, anti-angiogenic agent, or checkpoint inhibitor.

In some aspects, the pharmaceutical composition comprises an adjuvant for augmenting immune response for vaccinating the subject in need thereof. In some embodiments, the adjuvant can comprise analgesic adjuvants. In some embodiments, the adjuvant can comprise inorganic compounds such as alum, aluminum hydroxide, aluminum phosphate, or calcium phosphate hydroxide. In some embodiments, the adjuvant can comprise mineral oil or paraffin oil. In some embodiments, the adjuvant can comprise bacterial products such as inactivated *Bordetella pertussis, Mycobacterium bovis*, tor oxoids. In some embodiments, the adjuvant can comprise nonbacterial organics like squalene. In some embodiments, the adjuvant can comprise the use of delivery systems such as detergents (Quil A). In some embodiments, the adjuvant can comprise plant saponins such as saponin derived from Quillaja, soybean, or Polygala senega. In some embodiments, the adjuvant can comprise Freund's complete adjuvant or Freund's incomplete adjuvant. In some embodiments, the adjuvant can comprise food-based oil like peanut oil.

In practicing the methods of treatment or use provided herein, therapeutically effective amount of pharmaceutical composition described herein is administered to a mammal having a disease or condition to be treated, e.g., cancer or lesion. In some aspects, the mammal is a human. A therapeutically effective amount may vary widely depending on the severity of the disease, the age and relative health of the subject, the potency of the therapeutic agent used and other factors. The therapeutic agents, and in some cases, compositions described herein, may be used singly or in combination with one or more therapeutic agents as components of mixtures.

The pharmaceutical composition described herein may be administered to a subject by appropriate administration routes, including but not limited to bronchial lavage, sublingual, intravenous, intraarterial, oral, parenteral, buccal, topical, transdermal, rectal, intramuscular, subcutaneous, intraosseous, transmucosal, inhalation, or intraperitoneal administration routes. The composition described herein may include, but not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

The pharmaceutical composition including a therapeutic agent may be manufactured in a conventional manner, such as, by way of example only, by means of conventional mixing, dissolving, granulating, dragee-making, levigating, emulsifying, encapsulating, entrapping or compression processes.

The pharmaceutical composition may include at least an exogenous therapeutic agent as an active ingredient in free-acid or free-base form, or in a pharmaceutically acceptable salt form. In addition, the methods and compositions described herein include the use of N-oxides (if appropriate), crystalline forms, amorphous phases, as well as active metabolites of these compounds having the same type of activity. In some aspects, therapeutic agents exist in unsolvated form or in solvated forms with pharmaceutically acceptable solvents such as water, ethanol, and the like. The solvated forms of the therapeutic agents are also considered to be disclosed herein.

In certain embodiments, the pharmaceutical composition provided herein includes one or more preservatives to inhibit microbial activity. Suitable preservatives include mercury-containing substances such as phenylmercuric borate and thiomersal; stabilized chlorine dioxide; and quaternary ammonium compounds such as benzalkonium chloride, cetyltrimethylammonium bromide and cetylpyridinium chloride.

In some aspects, pharmaceutical composition described herein benefits from antioxidants, metal chelating agents, thiol containing compounds and other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, I about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (1) pentosan polysulfate and other heparinoids, (m) divalent cations such as magnesium and zinc; or (n) combinations thereof.

The pharmaceutical composition described herein can be formulated into any suitable dosage form, including but not limited to, aqueous oral dispersions, liquids, gels, syrups, elixirs, slurries, suspensions, solid oral dosage forms, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations. In one aspect, a therapeutic agent as discussed herein, e.g., therapeutic agent is formulated into a pharmaceutical composition suitable for intramuscular, subcutaneous, or intravenous injection. In one aspect, formulations suitable for intramuscular, subcutaneous, or intravenous injection include physiologically acceptable sterile aqueous or non-aqueous solutions, dispersions, suspensions or emulsions, and sterile powders for rehydration into sterile injectable solutions or dispersions. Examples of suitable aqueous and non-aqueous carriers, diluents, solvents, or vehicles include water, ethanol, polyols (propyleneglycol, polyethylene-glycol, glycerol, cremophor and the like), suitable mixtures thereof, vegetable oils (such as olive oil) and injectable organic esters such as ethyl oleate. Proper fluidity may be maintained, for example, by the use of a coating such as lecithin, by the maintenance of the required particle size in the case of dispersions, and by the use of surfactants. In some aspects, formulations suitable for subcutaneous injection also contain additives such as preserving, wetting, emulsifying, and dispensing agents. Prevention of the growth of microorganisms may be ensured by various antibacterial and antifungal agents, such as parabens, chlorobutanol, phenol, sorbic acid, and the like. In some cases, it is desirable to include isotonic agents, such as sugars, sodium chloride, and the like. Prolonged absorption of the injectable pharmaceutical form may be brought about by the use of agents delaying absorption, such as aluminum monostearate and gelatin.

For intravenous injections or drips or infusions, a pharmaceutical composition described herein is formulated in aqueous solutions, preferably in physiologically compatible buffers such as Hank's solution, Ringer's solution, or physiological saline buffer. For transmucosal administration, penetrants appropriate to the barrier to be permeated are used in the formulation. For other parenteral injections, appropriate formulations include aqueous or nonaqueous solutions, preferably with physiologically compatible buffers or excipients.

Parenteral injections may involve bolus injection or continuous infusion. Pharmaceutical composition for injection may be presented in unit dosage form, e.g., in ampoules or in multi dose containers, with an added preservative. The pharmaceutical composition described herein may be in a form suitable for parenteral injection as a sterile suspensions, solutions or emulsions in oily or aqueous vehicles, and may contain formulatory agents such as suspending, stabilizing and/or dispersing agents. In one aspect, the active ingredient is in powder form for constitution with a suitable vehicle, e.g., sterile pyrogen-free water, before use.

For administration by inhalation, a therapeutic agent is formulated for use as an aerosol, a mist or a powder. Pharmaceutical compositions described herein are conveniently delivered in the form of an aerosol spray presentation from pressurized packs or nebulizers, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of, such as, by way of example only, gelatin for use in an inhaler or insufflator may be formulated containing a powder mix of the therapeutic agent described herein and a suitable powder base such as lactose or starch. Formulations that include a composition are prepared as solutions in saline, employing benzyl alcohol or other suitable preservatives, fluorocarbons, and/or other solubilizing or dispersing agents known in the art. Preferably these compositions and formulations are prepared with suitable nontoxic pharmaceutically acceptable ingredients. The choice of suitable carriers is dependent upon the exact nature of the nasal dosage form desired, e.g., solutions, suspensions, ointments, or gels. Nasal dosage forms generally contain large amounts of water in addition to the active ingredient. Minor amounts of other ingredients such as pH adjusters, emulsifiers or dispersing agents, preservatives, surfactants, gelling agents, or buffering and other stabilizing and solubilizing agents are optionally present. Preferably, the nasal dosage form should be isotonic with nasal secretions.

In another aspect, dosage forms include microencapsulated formulations. In some aspects, one or more other compatible materials are present in the microencapsulation material. Non-limiting example of materials includes pH modifiers, erosion facilitators, anti-foaming agents, antioxidants, flavoring agents, and carrier materials such as binders, suspending agents, disintegration agents, filling agents, surfactants, solubilizers, stabilizers, lubricants, wetting agents, and diluents.

Liquid formulation dosage forms for oral administration are optionally aqueous suspensions selected from the group including, but not limited to, pharmaceutically acceptable aqueous oral dispersions, emulsions, solutions, elixirs, gels, and syrups. In addition to therapeutic agent the liquid dosage forms optionally include additives, such as: (a) disintegrating agents; (b) dispersing agents; (c) wetting agents; (d) at least one preservative, (e) viscosity enhancing agents, (f) at least one sweetening agent, and (g) at least one flavoring agent. In some aspects, the aqueous dispersions further include a crystal-forming inhibitor.

In some aspects, the pharmaceutical composition described herein can be self-emulsifying drug delivery systems (SEDDS). Emulsions are dispersions of one immiscible phase in another, usually in the form of droplets. Generally, emulsions are created by vigorous mechanical dispersion. SEDDS, as opposed to emulsions or microemulsions, spontaneously form emulsions when added to an excess of water without any external mechanical dispersion or agitation. An advantage of SEDDS is that only gentle mixing is required to distribute the droplets throughout the solution. Additionally, water or the aqueous phase is optionally added just prior to administration, which ensures stability of an unstable or hydrophobic active ingredient. Thus, the SEDDS provides an effective delivery system for oral and parenteral delivery of hydrophobic active ingredients. In some aspects, SEDDS provides improvements in the bioavailability of hydrophobic active ingredients.

Buccal formulations are administered using a variety of formulations known in the art. In addition, the buccal dosage forms described herein may further include a bioerodible (hydrolysable) polymeric carrier that also serves to adhere the dosage form to the buccal mucosa. For buccal or sublingual administration, the compositions may take the form of tablets, lozenges, or gels formulated in a conventional manner.

For intravenous injections, a pharmaceutical composition is optionally formulated in aqueous solutions, preferably in physiologically compatible buffers such as Hank's solution, Ringer's solution, or physiological saline buffer. For transmucosal administration, penetrants appropriate to the barrier to be permeated are used in the formulation. For other parenteral injections, appropriate formulations include aqueous or nonaqueous solutions, preferably with physiologically compatible buffers or excipients.

Parenteral injections optionally involve bolus injection or continuous infusion. Formulations for injection are optionally presented in unit dosage form, e.g., in ampoules or in multi dose containers, with an added preservative. In some aspects, a composition described herein is in a form suitable for parenteral injection as a sterile suspensions, solutions or emulsions in oily or aqueous vehicles, and contain formulatory agents such as suspending, stabilizing and/or dispersing agents. The compositions for parenteral administration include aqueous solutions of an agent that modulates the activity of a carotid body in water soluble form. Additionally, suspensions of an agent that modulates the activity of a carotid body are optionally prepared as appropriate, e.g., oily injection suspensions.

Conventional formulation techniques include, e.g., one or a combination of methods: (1) dry mixing, (2) direct compression, (3) milling, (4) dry or non-aqueous granulation, (5) wet granulation, or (6) fusion. Other methods include, e.g., spray drying, pan coating, melt granulation, granulation, fluidized bed spray drying or coating (e.g., Wurster coating), tangential coating, top spraying, tableting, extruding and the like.

In some aspects, the pharmaceutical composition can be provided that include particles of a therapeutic agent and at least one dispersing agent or suspending agent for oral administration to a subject. The formulations may be a powder and/or granule for suspension, and upon admixture with water, a substantially uniform suspension is obtained.

In some aspects, the pharmaceutical composition may include agent that facilitates vector binding and/or entry into a cell for either in vivo or ex vivo application. Certain pharmaceutical composition can comprise poly-cationic agent, either for co-administration or for pre-formulation with the vector described herein prior to administration to a patient, a subject, or to a cell derived from a patient or a subject. Such poly-cationic agents may include, but are not limited to, polybrene, protamine sulfate, or recombinant human fibronectin.

Furthermore, the pharmaceutical composition optionally includes one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Additionally, the pharmaceutical composition optionally includes one or more salts in an amount required to bring osmolality of the pharmaceutical composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite, and ammonium sulfate.

In one embodiment, the aqueous suspensions and dispersions described herein remain in a homogenous state for at least 4 hours. In one embodiment, an aqueous suspension is re-suspended into a homogenous suspension by physical agitation lasting less than 1 minute. In still another embodiment, no agitation is necessary to maintain a homogeneous aqueous dispersion.

An aerosol formulation for nasal administration is generally an aqueous solution designed to be administered to the nasal passages in drops or sprays. Nasal solutions may be similar to nasal secretions in that they are generally isotonic and slightly buffered to maintain a pH of about 5.5 to about 6.5, although pH values outside of this range may additionally be used. Antimicrobial agents or preservatives may also be included in the formulation.

An aerosol formulation for inhalations and inhalants may be designed so that the agent or combination of agents is carried into the respiratory tree of the subject when administered by the nasal or oral respiratory route. Inhalation solutions may be administered, for example, by a nebulizer. Inhalations or insufflations, comprising finely powdered or liquid drugs, may be delivered to the respiratory system as a pharmaceutical aerosol of a solution or suspension of the agent or combination of agents in a propellant, e.g., to aid in disbursement. Propellants may be liquefied gases, including halocarbons, for example, fluorocarbons such as fluorinated chlorinated hydrocarbons, hydrochlorofluorocarbons, and hydrochlorocarbons, as well as hydrocarbons and hydrocarbon ethers. Aerosol formulations may also include other components, for example, ethanol, isopropanol, propylene glycol, as well as surfactants or other components such as oils and detergents. These components may serve to stabilize the formulation and/or lubricate valve components.

Kit

Described herein, in some aspects, are kits for using the vector described herein. In some embodiments, the kit can be used to treat a disease or condition in a subject. In some embodiments, the kit can be used to vaccinate a subject. In some aspects, the kit comprises an assemblage of materials or components apart from the vector or a cell comprising the vector. In some aspects, the kit comprises the components for assaying the number of units of a biomolecule (e.g., a therapeutic agent including the vector, the cell, IL-12, the mutant HSV1-TK, the antigen such as Spike protein or HA protein or a combination thereof) synthesized, and/or released or expressed by the cell described herein. In some aspects, the kit comprises components for performing assays such as enzyme-linked immunosorbent assay (ELISA), single-molecular array (Simoa), PCR, and qPCR. The exact nature of the components configured in the kit depends on its intended purpose. For example, kits can be configured for the purpose of treating a disease or condition disclosed herein (e.g., cancer or lesion) in a subject. In some aspects, the kit is configured particularly for the purpose of treating mammalian subjects. In some aspects, the kit is configured particularly for the purpose of treating human subjects. In some aspects, the kit is configured particularly for the purpose of vaccinating mammalian subjects. In some aspects, the kit is configured particularly for the purpose of vaccinating human subjects.

Instructions for use may be included in the kit. In some aspects, the kit comprises instructions for administering the vector, the cell, or the pharmaceutical composition described herein to a subject in need thereof. In some aspects, the kit comprises instructions for further engineering the vector or cell to express a biomolecule (e.g., a therapeutic agent including the IL-12 the mutant HSV1-TK, or the antigen). In some aspects, the kit comprises instructions thawing or otherwise restoring biological activity of the cell, which may have been preserved during storage or transportation. In some aspects, the kit comprises instructions for measure viability of the preserved cell, to ensure efficacy for its intended purpose (e.g., therapeutic efficacy if used for treating a subject).

Optionally, the kit also contains other useful components, such as, diluents, buffers, pharmaceutically acceptable carriers, syringes, catheters, applicators, pipetting or measuring tools, bandaging materials or other useful paraphernalia. The materials or components assembled in the kit may be provided to the practitioner stored in any convenient and suitable ways that preserve their operability and utility. For example, the components may be in dissolved, dehydrated, or lyophilized form; they may be provided at room, refrigerated or frozen temperatures. The components are typically contained in suitable packaging material.

Use of absolute or sequential terms, for example, "will," "will not," "shall," "shall not," "must," "must not," "first," "initially," "next," "subsequently," "before," "after," "lastly," and "finally," are not meant to limit scope of the present embodiments disclosed herein but as exemplary.

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

As used herein, the phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

As used herein, "or" may refer to "and", "or," or "and/or" and may be used both exclusively and inclusively. For example, the term "A or B" may refer to "A or B", "A but not B", "B but not A", and "A and B". In some cases, context may dictate a particular meaning.

Any systems, methods, software, and platforms described herein are modular. Accordingly, terms such as "first" and "second" do not necessarily imply priority, order of importance, or order of acts.

The term "about" when referring to a number or a numerical range means that the number or numerical range referred to is an approximation within experimental variability (or within statistical experimental error), and the number or numerical range may vary from, for example, from 1% to 15% of the stated number or numerical range. In examples, the term "about" refers to ±10% of a stated number or value.

The terms "increased", "increasing", or "increase" are used herein to generally mean an increase by a statically significant amount. In some aspects, the terms "increased," or "increase," mean an increase of at least 10% as compared to a reference level, for example an increase of at least about 10%, at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, standard, or control. Other examples of "increase" include an increase of at least 2-fold, at least 5-fold, at least 10-fold, at least 20-fold, at least 50-fold, at least 100-fold, at least 1000-fold or more as compared to a reference level.

The terms "decreased", "decreasing", or "decrease" are used herein generally to mean a decrease by a statistically significant amount. In some aspects, "decreased" or "decrease" means a reduction by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g., absent level or non-detectable level as compared to a reference level), or any decrease between 10-100% as compared to a reference level. In the context of a marker or symptom, by these terms is meant a statistically significant decrease in such level. The decrease can be, for example, at least 10%, at least 20%, at least 30%, at least 40% or more, and is preferably down to a level accepted as within the range of normal for an individual without a given disease.

As used herein, "nucleic acid" refers to a polynucleotide containing at least two covalently linked nucleotide or nucleotide analog subunits. A nucleic acid is generally a deoxyribonucleic acid (DNA), a ribonucleic acid (RNA), or an analog of DNA or RNA. The nucleic acid is generally single-stranded, double-stranded, or a mixture thereof. For purposes herein, unless specified otherwise, the nucleic acid is double-stranded, or it is apparent from the context.

As used herein, "DNA" is meant to include all types and sizes of DNA molecules including cDNA, plasmids and DNA including modified nucleotides and nucleotide analogs.

As used herein, "nucleotides" include nucleoside mono-, di-, and triphosphates. Nucleotides also include modified nucleotides, such as, but are not limited to, phosphorothioate nucleotides and deazapurine nucleotides and other nucleotide analogs.

The term "polynucleotide" as used herein means a polymeric form of nucleotide of any length, and includes ribonucleotides and deoxyribonucleotides. Such term also includes single- and double-stranded DNA, as well as single- and double-stranded RNA. The term also includes modified polynucleotides such as methylated or capped polynucleotides.

As used herein, the term "subject" refers to animals, plants, insects, and birds into which the large DNA molecules are introduced. Included are higher organisms, such as mammals and birds, including humans, primates, rodents, cattle, pigs, rabbits, goats, sheep, mice, rats, guinea pigs, cats, dogs, horses, chicken and others. Subject may or may not have a disease or condition.

As used herein, "administering to a subject" is a procedure by which one or more delivery agents and/or large nucleic acid molecules, together or separately, are introduced into or applied onto a subject such that target cells which are present in the subject are eventually contacted with the agent and/or the large nucleic acid molecules.

As used herein, "delivery vector" or "delivery vehicle" or "therapeutic vector" or "therapeutic system" refers to both viral and non-viral particles that harbor and transport exogenous nucleic acid molecules to a target cell or tissue. Viral vehicles include, but are not limited to, retroviruses, adenoviruses, lentiviruses, herpes viruses and adeno-associated viruses. Non-viral vehicles include, but are not limited to, microparticles, nanoparticles, virosomes and liposomes. "Targeted," as used herein, refers to the use of ligands that are associated with the delivery vehicle and target the vehicle to a cell or tissue. Ligands include, but are not limited to, antibodies, receptors and collagen-binding domains.

As used herein, "delivery," which is used interchangeably with "transduction," refers to the process by which exogenous nucleic acid molecules are transferred into a cell such that they are located inside the cell. Delivery of nucleic acids is a distinct process from expression of nucleic acids.

As used herein, "expression" refers to the process by which nucleic acid is translated into polypeptide or is transcribed into RNA, which, for example, can be translated into polypeptide or protein. If the nucleic acid is derived from genomic DNA, expression includes, if an appropriate eukaryotic host cell or organism is selected, splicing of the mRNA. For heterologous nucleic acid to be expressed in a host cell, it must initially be delivered into the cell and then, once in the cell, ultimately reside in the nucleus. In some aspects, the expression occurs independent of gene integration.

As used herein, a "therapeutic course" refers to the periodic or timed administration of the vectors disclosed herein within a defined period of time. Such a period of time is at least one day, at least two days, at least three days, at least five days, at least one week, at least two weeks, at least three weeks, at least one month, at least two months, or at least six months. Administration could also take place in a chronic manner, i.e., for an undefined period of time. The periodic or timed administration includes once a day, twice a day, three times a day or other set timed administration.

As used herein, the terms "co-administration," "administered in combination with" and their grammatical equivalents or the like are meant to encompass administration of the selected therapeutic agents to a single patient, and are intended to include treatment regimens in which the agents are administered by the same or different route of administration or at the same or different times. In some embodiments, a therapeutic agent as disclosed in the present application will be co-administered with other agents. These terms encompass administration of two or more agents to an animal so that both agents and/or their metabolites are present in the animal at the same time. They include simultaneous administration in separate compositions, administration at different times in separate compositions, and/or administration in a composition in which both agents are present. Thus, in some embodiments, a therapeutic agent and the other agent(s) are administered in a single composition. In some embodiments, a therapeutic agent and the other agent(s) are admixed in the composition. In further embodiments, a therapeutic agent and the other agent(s) are administered at separate times in separate doses.

As used herein, the term "mutant thymidine kinase" refers to not only the specific protein described herein (as well as the nucleic acid sequences which encode these proteins), but derivatives thereof which may include various structural forms of the primary protein which retain biological activity.

As used herein, the term "mutated" or "replaced by another nucleotide" means a nucleotide at a certain position is replaced at that position by a nucleotide other than that which occurs in the unmutated or previously mutated sequence. That is, in some instances, specific modifications may be made in different nucleotides. In some embodiments, the replacements are made such that the relevant splice donor and/or acceptor sites are no longer present in a gene.

As used herein, a "polar amino acid" refers to amino acid residues Asn (N), Cys (C), Gln (Q), Gly (G), Ser (S), Thr (T) or Tyr (Y).

As used herein, a "non-polar amino acid" refers to amino acid residues Ala (A), Ile (I), Leu (L), Met (M), Phe (F), Pro (P), Trp (W), or Val (V).

As used herein, a "basic amino acid" refers to amino acid residues Arg (R), His (H), or Lys (K).

As used herein, an "acidic amino acid" refers to amino acid residues Asp (D) or Glu (E).

An "adjuvant" as described herein refers to a substance that in combination with an antigen promotes an adaptive immune response to the antigen. An "immune stimulatory compound" refers to a substance that specifically interacts with the innate immune system to initiate a "danger signal" that ultimately leads to the development of the adaptive components of the immune response (e.g., B cell, T cells). Immune stimulatory compounds include pathogen-associated molecular patterns (PAMPs) such as dsRNA, lipopolysaccharide, and CpG DNA, either naturally occurring or synthetic. Immune stimulatory compounds are agonists of various innate immune receptors including Toll-like receptors (TLRs), NOD-like receptors, RIG-1 or MDA-5 receptors, C-type lectin receptors, or the STING pathway.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

EXAMPLES

The following illustrative examples are representative of embodiments of the stimulation, systems, and methods described herein and are not meant to be limiting in any way.

Example 1. Generating Integrase Defective Vector

Simplified version of viral cycle of a retrovirus: After the enzyme reverse transcriptase (RT) has generated a cDNA of a retrovirus RNA genome, it immediately produces a double stranded DNA that binds to the viral enzyme Integrase. The integrase is the key enzyme that carries the viral DNA and catalyzes its integration into the host genome. The integrase is part of the gagpol gene which is translated into a polyprotein sequence that gets processed by the viral protease to yield 7 proteins. The integrase (INT) is a 408 aa protein at the C-Terminal of Gag-Pol (Table 2).

TABLE 2

MLV Gag-pol polyprotein representation

| Protein ID | MLV Gag-Pol polyprotein generates 7 proteins | | | | LENGTH 1737 | viralProt cleavage POS 2-1728 |
|---|---|---|---|---|---|---|
| | GAG | | POL | | | |
| Matrix protein p15 | MA | | | | 130 | 2-131 |
| RNA-binding phosphoprotein p12 | | p12 | | | 84 | 132-215 |
| Capsid protein p30 | | | CA | | 263 | 216-478 |
| Nucleocapsid protein p10-Pol | | | | NC | 56 | 479-534 |
| Protease | | | | PR | 125 | 535-659 |
| RT/ribonuclease H | | | | RT | 671 | 660-1330 |
| Integrase | | | | INT | 408 residues | 1331-1738 |

Comparative studies on integrase-defective retroviral vectors have determined the structure of their integrase and different domains. FIG. 1 illustrates the D, D, and E amino acid triad that forms the Mg2+ binding motif that is critical to integrase function.

Additionally, the comparative studies were utilized for determining amino acid residues that could be mutated in reverse transcriptase (RT) to generate reverse transcriptase-defective retroviral vectors. Two approaches were taken: three amino acid mutations at the active site of the RT enzyme; and base mutations on the RT binding region on the payload vector described herein (artificial Primer Binding site (aPBS)

Generation of 7 Mutant Integrase Sequences

Base substitutions were introduced to alter amino acids in the integrase catalytic core domain sequence of the gagpol gene of MLV. Single base mutations were introduced in the catalytic core domain by site-directed mutagenesis (using Q5 Site-Directed Mutagenesis kit, NEB) with primers designed to introduce single base mutations into the wild-type gagpol (wtGP) sequence, vector pGP340-VKS. The first mutant generated was D184A (FIG. 2). A single base was changed in the codon, from GAC to GCC. (point-mutation at base 4541 of the gagpol gene). The same procedure was used to generate the single mutants D125A (GAC to GcG) and E220A (GAG to GcG) (primer design; FIG. 3). The single mutations were confirmed by sequencing (Laragen, Inc., CA) before moving on to generate the double mutants. The double mutants were generated through a second round of site-mutagenesis carried out with the primers of choice on the single mutant previously obtained and sequenced. The Triple mutant was generated by a third round of site directed mutagenesis on the double mutant D184A/E220A. All vectors were analyzed by restriction enzyme digest and mutations were confirmed by sequencing (Laragen, Inc., CA). Table 3 illustrates seven exemplary mutant gagpol sequences described herein. Table 4 illustrates polypeptide sequences of integrase fragment spanning amino acid position 106 to amino acid position of 287 of wild-type integrase (SEQ ID NO: 1) and the seven mutant integrases (SEQ ID NO: 2-8). The last two bases of the codon were changed, from GAT to GCC (point mutations at & near base 4541 of the gagpol gene). Single point mutations were used in the mutations D184A and E220A, converting GAC to GCC and GAG to GCG, respectively.

TABLE 3

7 mutants constructed: 3 point mutations, 3 double mutants, 1 triple mutant of Gag-Pol

| | Gag-Pol Sequences | Mutation in gagpol integrase catalytic core domain |
|---|---|---|
| Wild type | GP340-VKS | none |
| Single | D125A | GAT to GCC |
| | D184A | GAC to GCC |
| | E220A | GAA to GCC |
| Double | D125A/D184A | D125A mutation introduced into mutGP-D184A |
| | D184A/E220A | E220A mutation introduced into mutGP-D184A |
| | D125A/E220A | D125A mutation introduced into mutGP-E220A |
| Triple | D125A/D184A/E220A | D125A mutation introduced into double mutGP-D184A-E220A |

TABLE 4

Polypeptide sequences of wild-type and mutant integrase

| Integrase type | SEQ ID NO: | Polypeptide sequence of integrase of amino acid positions 106-287 |
|---|---|---|
| Wild-type | 1 | AVKQG TRVRGHRPGT HWEIDFTEIK PGLYGYKYLL VFIDTFSGWI EAFPTKKETA KVVTK KLLEE IFPRFGMPQV LGTDNGPAFV SKVSQTVADL LGIDWKLHCA YRPQSSGQVE RMNRT IKETL TKLTLATGSR DWVLLLPLAL YRARNTPGPH GLTPYEILYG APPPL VNFPD PDMTR VT |
| D125A | 2 | AVKQG TRVRGHRPGT HWEIAFTEIK PGLYGYKYLL VFIDTFSGWI EAFPTKKETA |

TABLE 4-continued

Polypeptide sequences of wild-type and mutant integrase

| Integrase type | SEQ ID NO: | Polypeptide sequence of integrase of amino acid positions 106-287 |
|---|---|---|
| | | KVVTK KLLEE IFPRFGMPQV LGTDNGPAFV SKVSQTVADL LGIDWKLHCA YRPQSSGQVE RMNRT IKETL TKLTLATGSR DWVLLLPLAL YRARNTPGPH GLTPYEILYG APPPL VNFPD PDMTR VT |
| D184A | 3 | AVKQG TRVRGHRPGT HWEIDFTEIK PGLYGYKYLL VFIDTFSGWI EAFPTKKETA KVVTK KLLEE IFPRFGMPQV LGTANGPAFV SKVSQTVADL LGIDWKLHCA YRPQSSGQVE RMNRT IKETL TKLTLATGSR DWVLLLPLAL YRARNTPGPH GLTPYEILYG APPPLVNFPD PDMTR VT |
| E220A | 4 | AVKQG TRVRGHRPGT HWEIDFTEIK PGLYGYKYLL VFIDTFSGWI EAFPTKKETA KVVTK KLLEE IFPRFGMPQV LGTDNGPAFV SKVSQTVADL LGIDWKLHCA YRPQSSGQVA RMNRT IKETL TKLTLATGSR DWVLLLPLAL YRARNTPGPH GLTPYEILYG APPPL VNFPD PDMTR VT |
| D125A and D184A | 5 | AVKQG TR VRGHRPGT HWEIAFTEIK PGLYGYKYLL VFIDTFSGWI EAFPTKKETA KVVTK KLLEE IFPRFGMPQV LGTANGPAFV SKVSQTVADL LGIDWKLHCA YRPQSSGQVE RMNRT IKETL TKLTLATGSR DWVLLLPLAL YRARNTPGPH GLTPYEILYG APPPLVNFPD PDMTR VT |
| D125A and E220A | 6 | AVKQG TR VRGHRPGT HWEIAFTEIK PGLYGYKYLL VFIDTFSGWI EAFPTKKETA KVVTK KLLEE IFPRFGMPQV LGTDNGPAFV SKVSQTVADL LGIDWKLHCA YRPQSSGQVA RMNRT IKETL TKLTLATGSR DWVLLLPLAL YRARNTPGPH GLTPYEILYG APPPL VNFPD PDMTR VT |
| D184A and E220A | 7 | AVKQG TR VRGHRPGT HWEIDFTEIK PGLYGYKYLL VFIDTFSGWI EAFPTKKETA KVVTK KLLEE IFPRFGMPQV LGTANGPAFV SKVSQTVADL LGIDWKLHCA YRPQSSGQVA RMNRT IKETL TKLTLATGSR DWVLLLPLAL YRARNTPGPH GLTPYEILYG APPPL VNFPD PDMTR VT |
| D125A, D184A, and E220A | 8 | AVKQG TR VRGHRPGT HWEIAFTEIK PGLYGYKYLL VFIDTFSGWI EAFPTKKETA KVVTK KLLEE IFPRFGMPQV LGTANGPAFV SKVSQTVADL LGIDWKLHCA YRPQSSGQVA RMNRT IKETL TKLTLATGSR DWVLLLPLAL YRARNTPGPH GLTPYEILYG APPPL VNFPD PDMTR VT |

Comparison with Wild-Type Gag-Pol Produced Particles

Viral supernatants were produced with each integrase-defective vector (using triple transfection of 293T cells with envelope plasmid and a payload/reporter plasmid) and properties were compared to particles made with wtGP vector. Similar titers were obtained (FIG. 4), demonstrating that integrase mutations do not interfere with other functions of Gag-pol needed to generate viral particles.

Infectivity and Payload Expression Over Time

Routine target cell line A375 (human melanoma) were transduced with the viral vector supernatants. Expression of payloads were analyzed visually (GFP payload), by FACS (for vTK), or payload activity (Luciferase reporter gene in payload) or vTK activity (GCV-induced cell kill assay). The results demonstrated that the mutation did not interfere with viral envelope production. Level of payload protein expression demonstrated that integrase mutations did not interfere with payload level of expression (examined by cell kill, reflecting payload vTK expression and activity; as well as by Western blotting for vTK protein; FIG. 5 and FIG. 6). Timing of payload protein expression demonstrated that, due to mutations rendering the integrase dysfunctional, the payload gene could not integrate into host genome and consequently the level of payload protein expression decreased over time (loss of GCV sensitivity in cell kill assays, FIG. 5; fading of vTK protein band intensity in Western Blotting, FIG. 6). Lack of vTK gene integration over time was demonstrated by Relative Integration qPCR, confirming the mutation(s) disables the integrase (FIG. 7 and FIG. 8). The single mutant (D184A) and the double-mutant (D125A-

D184A) were selected after careful evaluation of the characteristics recorded for each mutant integrase sequence generated.

Generation of Manufacturing Vector Integrase-Defective Cell Line

In order to facilitate generation of packaging cell lines with each integrase-defective vector. the gagpol sequence with the integrase mutation selected were cloned into gagpol vector constructs and sequenced. The envelope expressing 293T packaging cell line was transformed with the integrase-defective gagpol retroviral vectors and tested.

Testing the Packaging Cell Lines

The integrase-defective packaging lines were compared with wtGP by transfecting all three packaging cell lines with a vector described herein. Titers obtained were in similar range (Table 5). The viral vector supernatants were used to transduce routine target cell line A375 with 2e7 vector genomes/mL in order to follow vTK expression and observe non-integration from the integrase-defective particles. The expression of vTK is reflected by cell kill assays in which cells were exposed to GCV at given time post transduction. At Day 3 post transduction, the cell kill percentages were 79%, 59% and 69% for wtGP, mutGP-D184A and mutGP-D125A/D184A, respectively. At Day 7, there is approximately 80% less cell kill activities in cells transduced with the integrase-defective particles which reached nearly zero by Day 23.

TABLE 5

Titers of vectors with integrase-defective mutants

| ENV-GP Packaging lines Transfected with GMSTK | Vector Genomes/mL |
|---|---|
| Env-G8/wtGP + GMSTK | 7.26E+07 |
| Env-G8/mutGP D184A + GMSTK | 5.74E+07 |
| Env-G8/mutGP-D125A-D184A + GMSTK | 7.80E+07 |

Generation of Integrase-Defective Vector Manufacturing Cell Line

Envelope and integrase-defective gagpol expressing 293T packaging cell line was transformed with the payload vectors described herein to generate the integrase-defective vector manufacturing cell line(s), followed by single cell cloning, as the payload sequence bears no drug selection marker.

The same integrase-defective packaging cell line with D184A vector was also used for preclinical studies by introducing retroviral vector expressing murine GMCSF, followed by cell cloning.

Integrase-Defective D184A Vector Line

Figure 10:
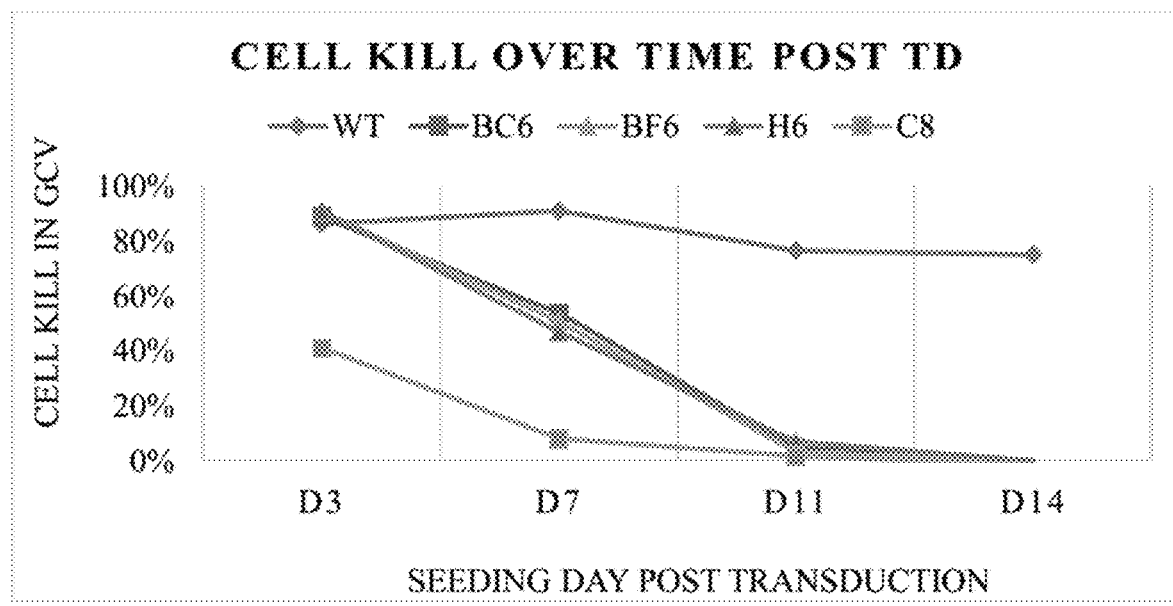
FIG. 10 illustrates vTK/GCV cell kill activity of integrase-defective vector cell lines.
Figure 11:
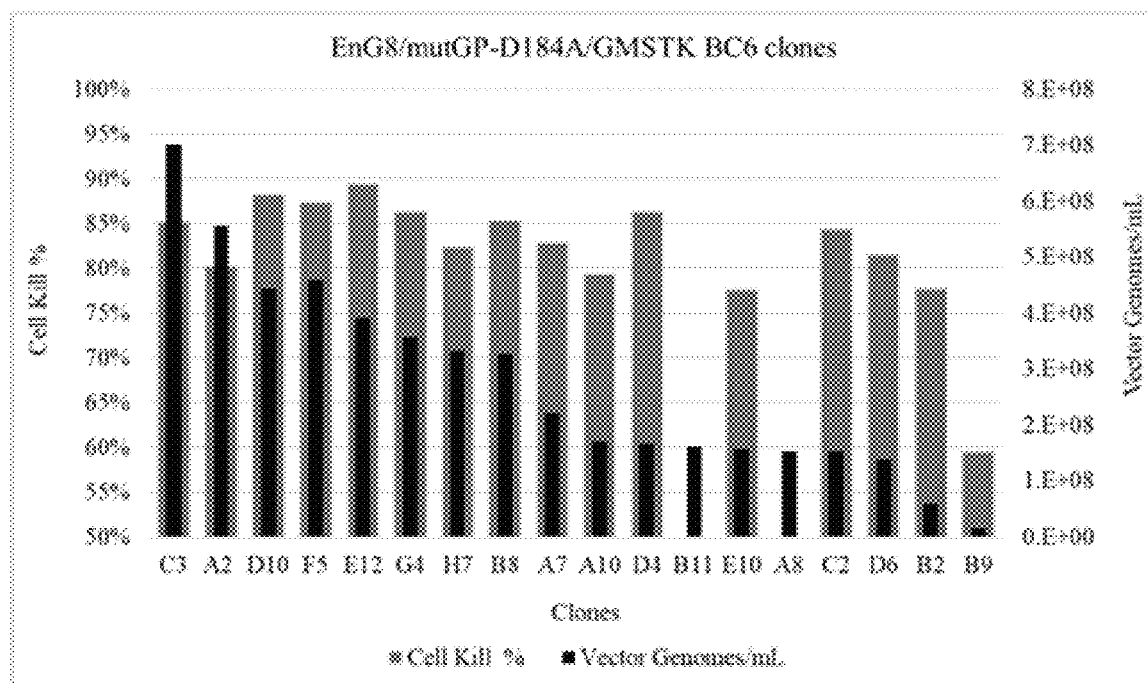
FIG. 11 illustrates viral vector titer and vTK/GCV cell kill of integrase-defective BC6 vector clones.

The first round of cloning resulted in the selection of 4 positive clones (BC6, BF6, H6, C8). Viral supernatants generated by these manufacturing cell lines were compared for titer, and vTK expression over time in transduced A375 cells by cell kill assays exposing cells to GCV at different times post-transduction (Table 6; FIG. 10).

TABLE 6

Viral vector titer of integrase-defective-D184A retroviral vector GMSTK cell lines

| IDRV-D184A GMSTK Clone | Vector Genomes/mL |
|---|---|
| BC6 | 1.22E+09 |
| BF6 | 4.18E+08 |
| C8 | 1.69E+08 |
| H6 | 1.53E+09 |

Based on titer, vTK expression profile, cell growth and morphology, clone BC6 was selected for second round of cloning. Second clones BC6-C3 and BC6-E12 were selected out of 18 tested (FIG. 11) based on titer and cell kill level of transduced A375 cells. The clone BC6-C3 was expanded and adapted to suspension.

Integrase-Defective D184A Vector Line with Murine GMCSF

The first round of cloning resulted in selection of 4 infectious clones (Table 7). Of all, clone G7 was picked to be the best with a titer of 1.25E+09 vector genomes/mL and 20 psi sequence copies integrated.

TABLE 7

Viral vector titer of mGMSTK integrase-defective cell lines

| IDRV-D184A mGMSTK Clone | Vector Genomes/mL |
|---|---|
| 2D9 | 4.64E+08 |
| 2G5 | 4.34E+08 |
| G7 | 4.87E+08 |
| 2D6 | 6.49E+06 |

Figure 12A:
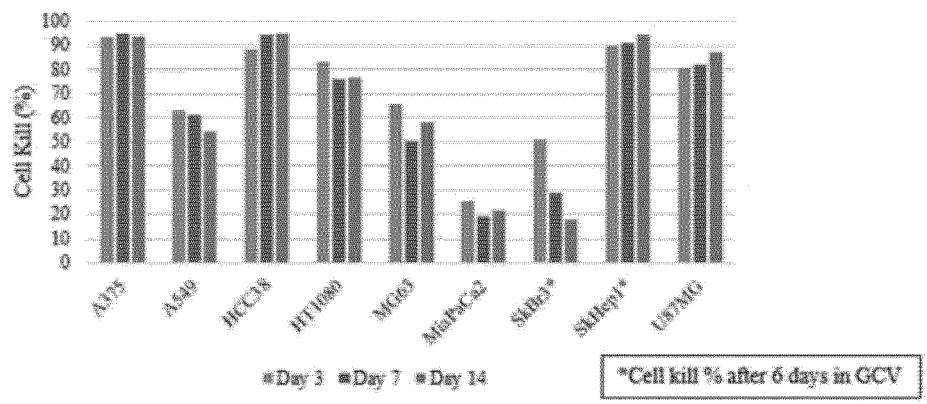
FIG. 12A-C illustrate vTK/GCV cell kill activities of various cancer cell lines between wtGP (FIG. 12A) and integrase-defective mutants (FIG. 12B).
Figure 12B:
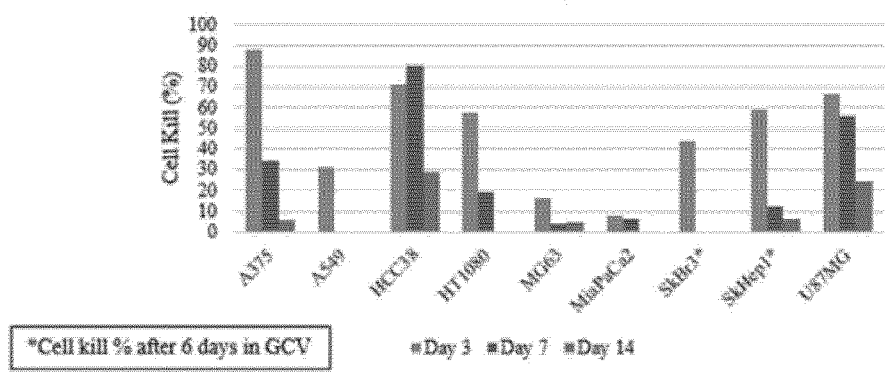
Figure 12C:
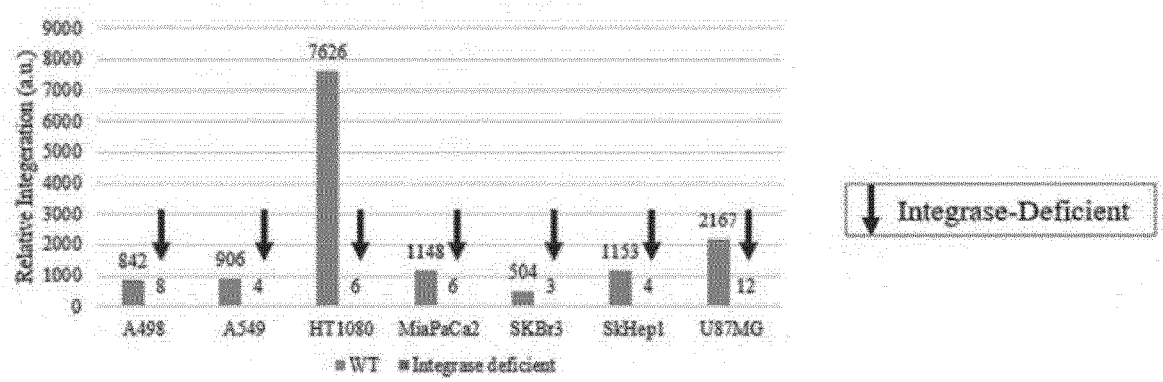

Integrase-Defective Vectors Elicit Expression of Payload in Various Cancer Cell Lines Tested A range of cancer cell lines were tested with integrase-defective vectors. When the cells were successfully transduced with the integrase-defective retroviral vector, the expression of payload disappeared between D7-D14 for most lines tested, as demonstrated by WB, GCV-Cell kill assays, and Relative Integration qPCR. FIG. 12A-C illustrate vTK/GCV cell kill activities of various cancer cell lines, from wtGP vector (FIG. 12A) and integrase-defective mutant vector (FIG. 12B). FIG. 12C illustrates relative integration of the vector payload by qPCR in cells treated with wtGP vector and integrase-defective mutant vector.

Example 2. Expression of SARS-CoV-2 Antigen

Figure 13:
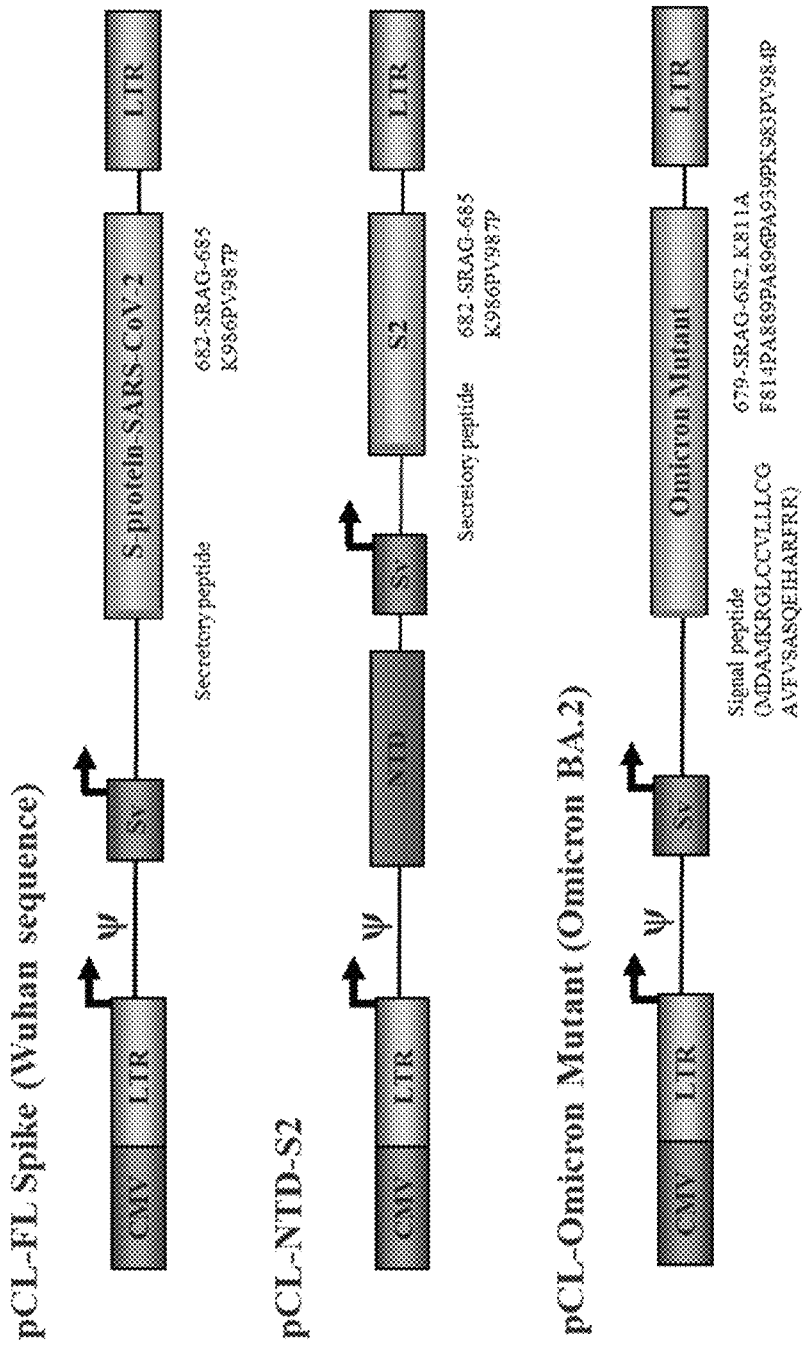
FIG. 13 illustrates exemplary schematic diagrams of the recombinant retroviral vectors comprising nucleic acid sequences encoding Spike protein or fragment thereof of SARS-CoV-2. Top: diagram of retroviral vector encoding SARS-CoV-2 full-length Spike protein (Wuhan sequence with modifications). Middle: diagram of retroviral vector encoding SARS-CoV-2 Spike protein fragment of N-terminal domain (NTD) and S2 domain (Wuhan sequence with modifications). Bottom: diagram of retroviral vector encoding SARS-CoV-2 full-length Spike protein (Omicron BA.2 sequence with modifications).

The integrase-defective retroviral vector (IDRV) can be generated with the integrase-defective Gagpol and any payload gene of interest. Such transient protein expression of the IDRV system provides a potential vaccine use. Three SARS-CoV-2 vaccine payloads were designed and generated. Testing was performed with transient transfection of three plasmids: vaccine payload, IDRV1 (D184A), or IDRV2 (D125A/D184A) Gagpol, and amphotropic envelope or a modified Sindbis Envelope which was targeted to antigen presenting dendritic cells. FIG. 13 illustrates exemplary schematic diagrams of the recombinant retroviral vectors comprising nucleic acid sequences encoding Spike protein or fragment thereof of SARS-CoV-2. Top: diagram of retroviral vector encoding SARS-CoV-2 full-length Spike protein (Wuhan sequence with modifications). Middle: diagram of retroviral vector encoding SARS-CoV-2 Spike protein fragment of N-terminal domain (NTD) and S2 domain (Wuhan sequence with modifications). Bottom: diagram of retroviral vector encoding SARS-CoV-2 full-length Spike protein (Omicron BA.2 sequence with modifications).

The first vaccine was a retroviral vector comprising a nucleic acid sequence encoding full-length Spike protein based on Wuhan strain with modifications. The nucleic acid sequence was codon optimized for expression in a human cell. The secretory leader sequence (IgEpsylon Fc Receptor alpha) was added at the N-terminus. The furin cleavage site at residue 682 to 685 was modified from RRAR to SRAG which could stabilize the Spike protein. The serine protease cleavage site was modified to proline at residue 986 and 987, which stabilized the Spike structure's prefusion shape.

The second vaccine was a retroviral vector comprising a nucleic acid sequence encoding N-terminal domain and S2 protein based on SARS-CoV-2 Wuhan strain with modifications. The nucleic acid sequence was codon optimized for expression in a human cell. The secretory leader sequence (IgEpsylon Fc Receptor alpha) was added at the N-terminus of the S2. Furin cleavage site at residue 682 to 685 was modified from RRAR to SRAG to stabilize the spike peptide. Serine protease cleavage site was modified to proline at residue K986 and V987 to stabilize the structure's prefusion shape.

The third vaccine was a retroviral vector comprising a nucleic acid sequence encoding Spike protein of the Omicron BA.2 strain with modifications. The nucleic acid sequence was codon optimized for human. Furin cleavage site at residue 679 to 682 was modified from RRAR to SRAG to stabilize the Spike peptide. Additional furin cleavage site was removed at K811A. Serine protease cleavage site was modified to proline at residue K983 and V984 to stabilize Spike structure's prefusion shape. Additional four more residues were modified to proline at residue F814, A889, A896, and A939. The signal peptide was added to the N-terminus, where the signal peptide was a propeptide of tissue Plasminogen Activator (SEQ ID NO: 13: MDAMKR-GLCCVLLLCGAVFVSASQEIHARFRR).

Figure 15:
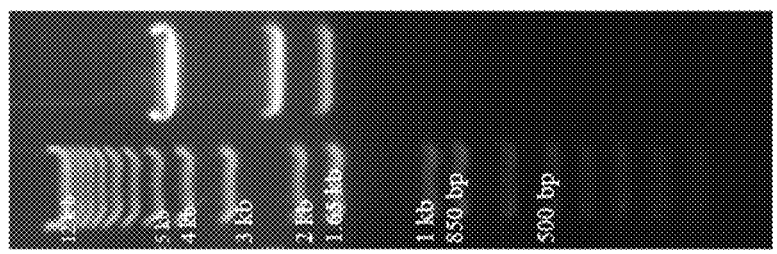
FIG. 15 illustrates presence of an E160G mutation in a Sindbis virus envelope.

In some aspects, the vaccine composition can be packaged and expressed by Sindbis virus. In some cases, the Sindbis virus can be a modified Sindbis virus. Sindbis envelope. In one of the alphavirus species, Sindbis virus (SB), the envelope gene encodes four components E3, E2, 6K, and E1 (from N-terminal to C-terminal). They are proteolytically separated and form a homotrimer. A unique characteristic of SB envelope is that these four subunits have their own functions. E3 is dissociated upon the maturation of E2 domain; E2 domain serves as a binding molecule; and fusion is regulated by E1 whereas the function of 6K is unclear. Binding and fusion of the virus particle are in two separate actions which made modifications of E2 possible without affecting the E1 structure and function. Here the residue 160 at E2 was mutated to target to human dendritic cells by pseudotyping a retroviral vector comprising a payload described herein. Modified Sindbis envelop comprising the E160G mutation was confirmed by Sanger sequencing at Laragen (Culver City, CA). E160G mutation would target the recombinant retroviral vector to antigen presenting cells (e.g., a dendritic cell) at the injection site (FIG. 15).

Figure 14A:
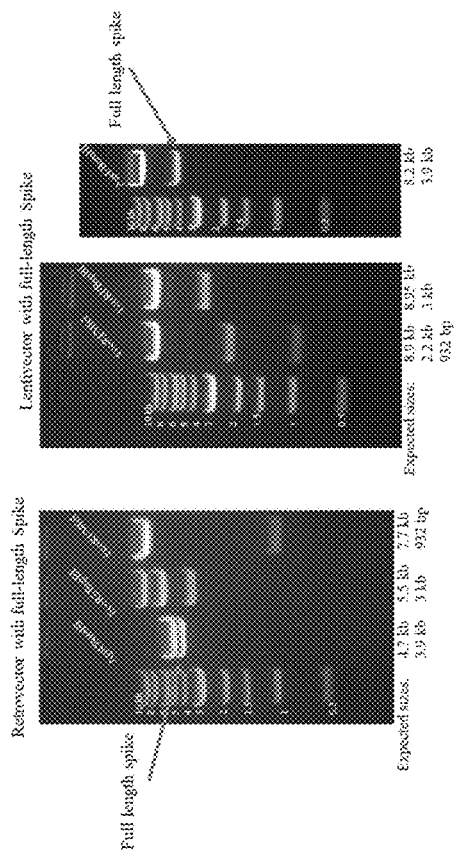
FIG. 14A illustrates presence of full-length spike transgene as a payload of a retroviral vector described herein or a lentivector.
Figure 14B:
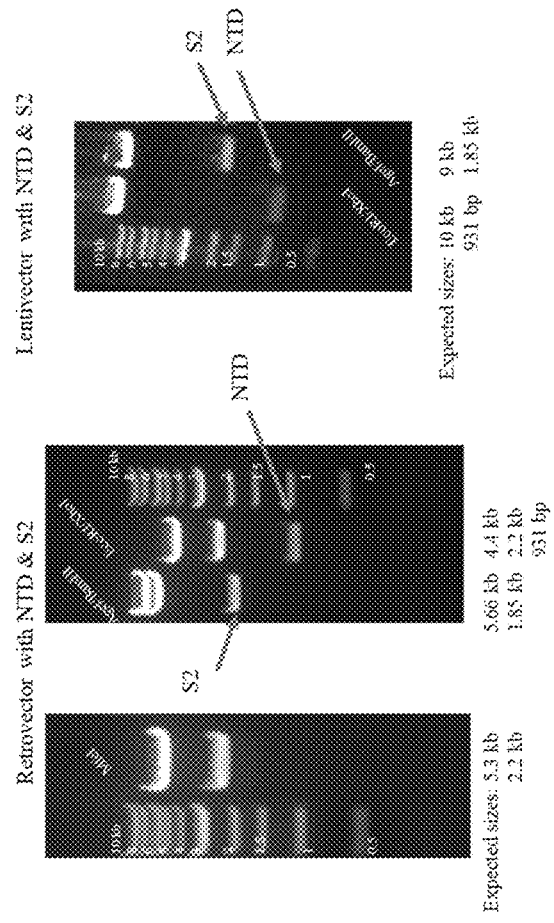
FIG. 14B illustrates presence of NTD and S2 transgene as a payload of a retroviral vector described herein or a lentivector.
Figure 14C:
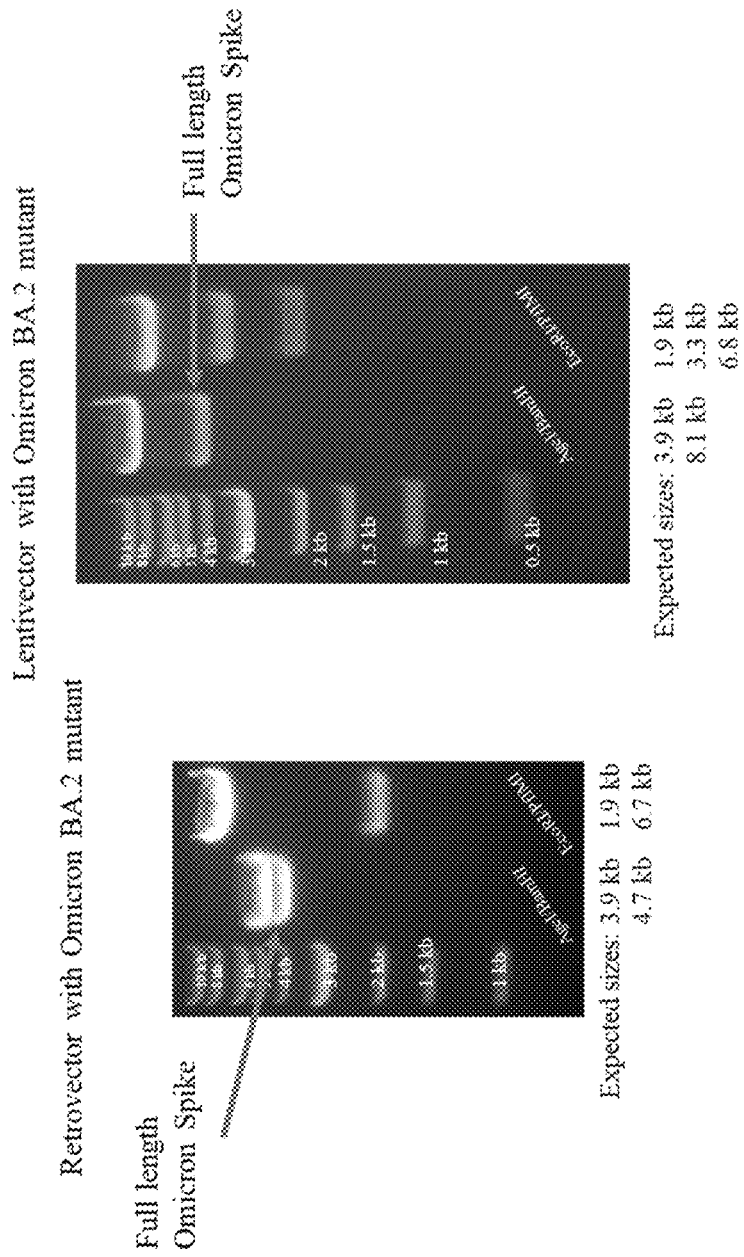
FIG. 14C illustrates presence Omicron BA.2 transgene (full-length spike) as a payload of a retroviral vector described herein or a lentivector.

All transgenes were designed as described above and synthesized at Genscript (Piscataway, NJ). Sequences were confirmed by Sanger sequencing at Genscript. The plasmids expressing transgenes were digested with appropriate restriction enzymes and inserted into a payload retroviral vector and lentivector described herein (e.g., FIGS. 14A-14C). All final plasmids were sequenced at Primordium Labs (Arcadia, CA).

Figure 17B:
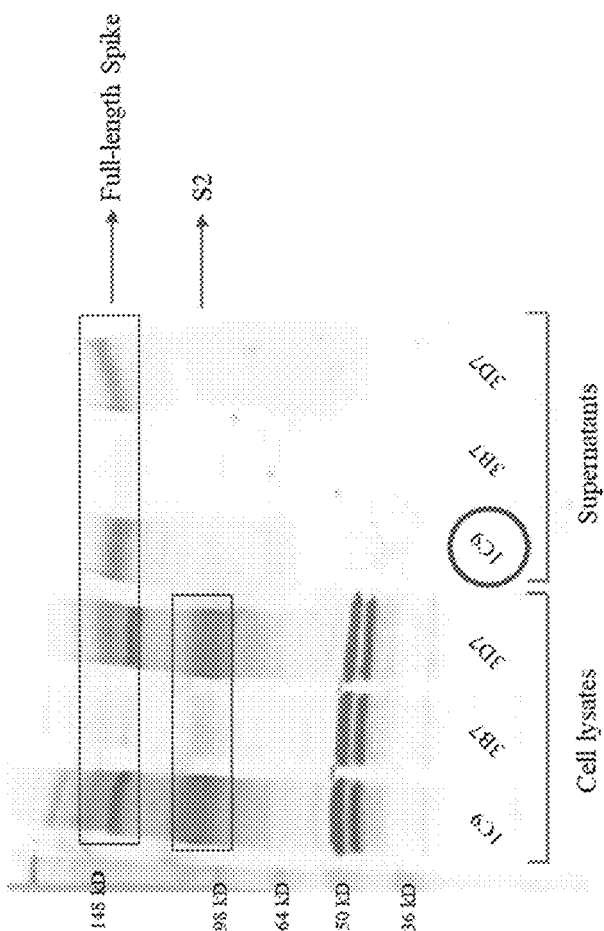
FIG. 17B illustrates Western blotting of intracellular and secreted full-length Spike proteins from A375 cells transduced with retroviral vector produced from clonal manufacturing cell lines.
Figure 17A:
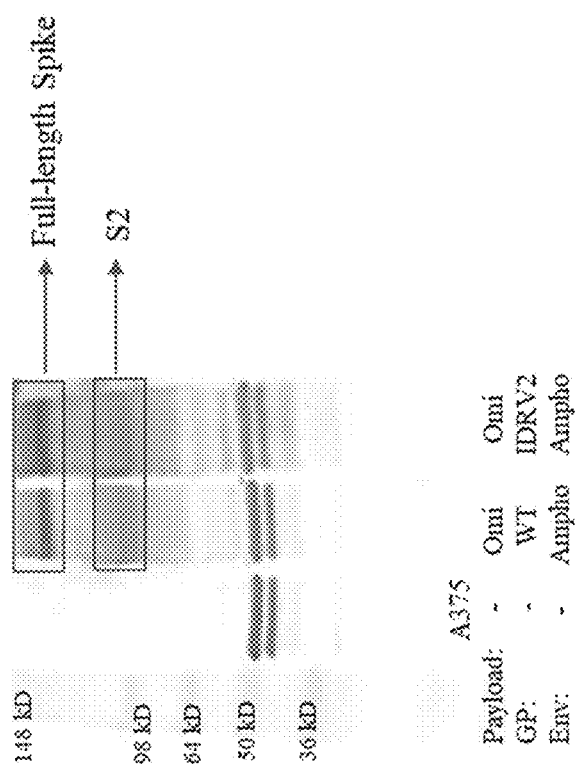
FIG. 17A illustrates Western blotting of intracellular full-length Spike proteins from A375 cells transduced with retroviral vector expressing the Omicron variant sequence with modifications and wild-type integrase or IDRV2 (IDRV2: D125A mutation and D184A mutation).

Retroviral vector was generated by calcium/phosphate transient transfection methods with wild-type gagpol or IDRV1 (D184A) gagpol with amphotropic envelope and the full-length spike payload or NTD-S2 payload. A375 cells were transduced with retroviral vector, at 1E+08 vector genomes/mL, and their culture supernatants were examined by Western blotting. The results (FIG. 16A and FIG. 16B) demonstrated stable expression of secreted Spike proteins with IDRV1 although levels of expression were lower than with wild-type gagpol. Similar results were shown with the NTD-S2 payload. Experiments were repeated with IDRV2 (D125AD184A) gagpol) vectors and similar results were obtained as shown in FIG. 16C. Both payloads showed stable expression in the supernatants. Retroviral vectors were also generated by transient transfection methods with the Omicron mutant of Spike protein, and wild-type gagpol or IDRV2 gagpol. Intracellular Spike proteins from retroviral vector transduced A375 cells were examined by Western blotting and the results demonstrated the high level of full-length Spike protein expression as shown in FIG. 17A.

The full-length Spike payload lentivector was used to generate the manufacturing cell line with fully codon optimized amphotropic envelope and wild-type gagpol, and the cell line was cloned. Table 8 shows the physical titer of the cell line clones, which was measured by RT-qPCR (reverse-transcriptase quantitative PCR) for the Psi sequence in extracted vector RNA. The results demonstrated acceptable titer of the manufacturing cell line at 9.6E+07 vector genomes/mL.

TABLE 8

| Retroviral vector (RV) titer (vector genomes/mL) of the manufacturing cell line | |
|---|---|
| Sample | Vector genomes/mL |
| T80 293T/GPwt/EnvG8/ Spike 3B7 | 4.78E+06 |
| T80 293T/GPwt/EnvG8/ Spike 3D7 | 9.62E+07 |
| T80 293T/GPwt/EnvG8/ Spike 1C9 | 9.61E+07 |

The recombinant retroviral vector produced from the cell line clones were tested on A375 melanoma cells. After transduction, cells and supernatants were examined by Western blotting for expression of Spike protein, S2 region. The results proved that full-length Spike proteins were generated in transduced cells and secreted out of the cell as shown in FIG. 17B.

Figure 18B:
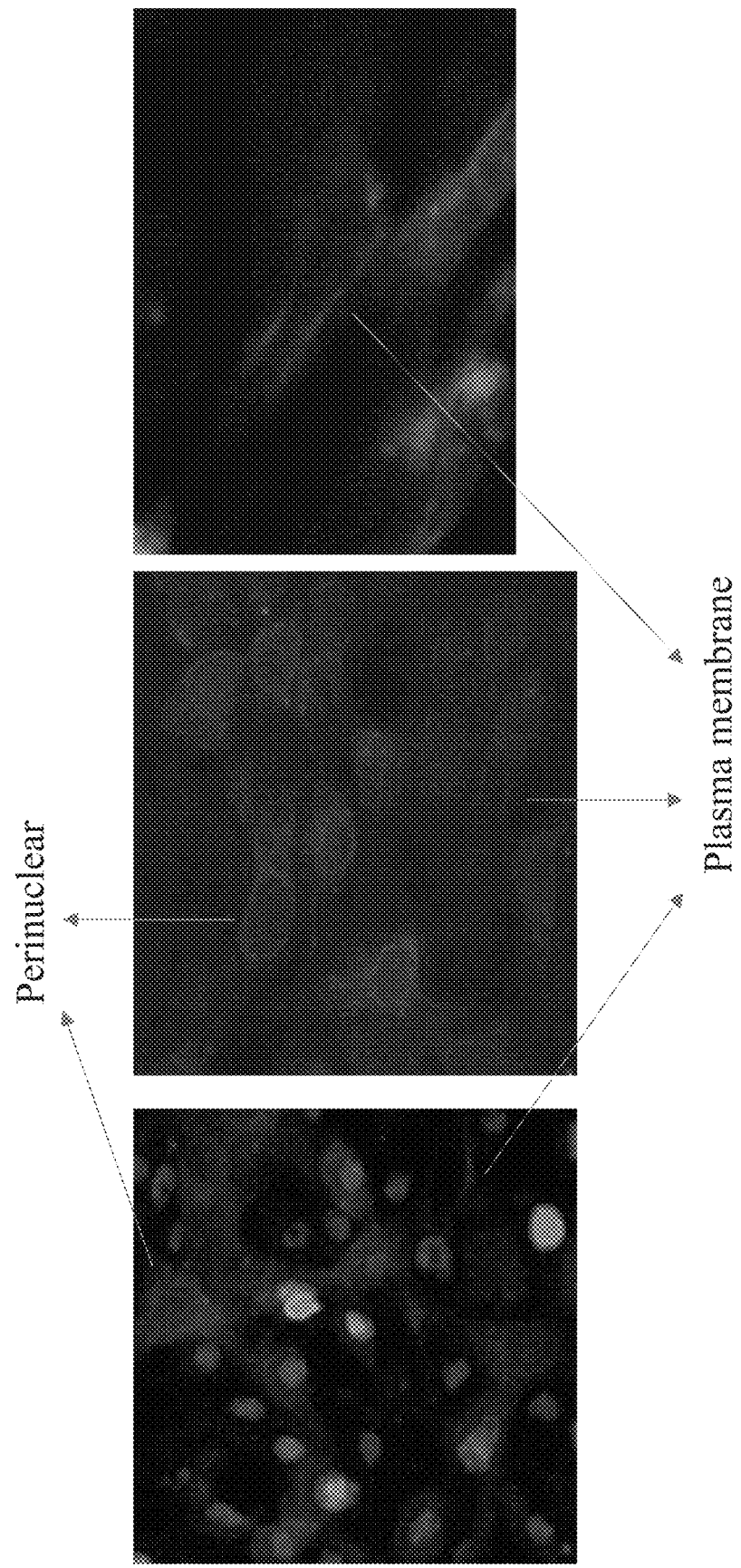
FIG. 18B illustrates expression of Omicron Spike proteins detected by immunocytochemistry (ICC) staining. Bright spots showed nuclear staining, and gray color showed the specific perinuclear and plasma membrane staining of Omicron Spike protein.
Figure 18C:
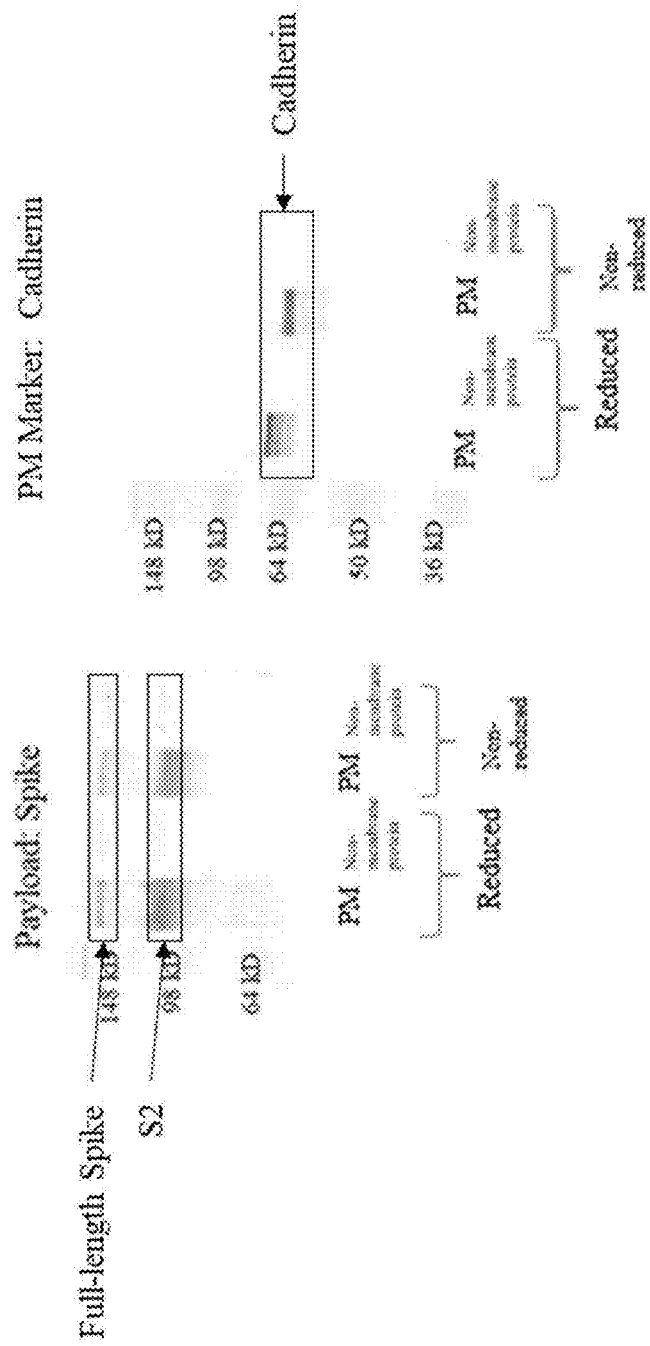
FIG. 18C illustrates Western blotting of both reduced and non-reduced Spike proteins detected by anti-S2 antibody in the plasma membrane fraction. The Western blot for the same samples probing for the plasma membrane marker, Cadherin, is also shown.

Recombinant retroviral vector with a payload encoding the Omicron mutant Spike protein was obtained by transiently co-transfecting 293T with wtGP and amphotropic envelope. The titer was 4.81E+07 vector genomes/mL, as determined by RT-qPCR. Manufacturing cell lines, expressing IDRV2 and amphotropic envelope, were generated to produce Omicron mutant payload retroviral vector particles. Titers from two exemplary clones, measured by RT-qPCR, were 1.63E+08 vector genomes/mL and 4.67E+07 vector genomes/mL, respectively. When testing cells were transduced with Omicron mutant Spike retroviral vector, the Spike protein was detected both in the cell lysates and conditioned media (cell culture supernatants) by Western Blotting (FIG. 18A). Immunocytochemistry staining for the Omicron mutant Spike protein demonstrated expression of Spike protein and presence in the perinuclear and plasma membrane region of testing cells (FIG. 18B). Omicron retroviral vector transduced A375 cells were fractionated by simple centrifugation methods, and the plasma membrane fraction and non-membrane soluble proteins were subjected to Western blotting (FIG. 18C). Spike proteins were distinctively present in the plasma membrane fraction along with the plasma membrane marker, Cadherin.

To determine the best transient transfection conditions, varying amounts of various payloads, wild-type and IDRV gagpol, and envelopes, may be being examined by transient transfection methods. Sindbis E160G expressing retroviral vector may be examined with dendrite cells (FIG. 15). The payloads of vaccine of interest can be generated as retroviral vectors in a large scale, such as in CS10 flasks, and then be column-purified. Two types of animal studies can be conducted. The purified retroviral vector can be examined in regular BALB/c and C57BL/6J mice by 4 different routes (intramuscular, sublingual, intranasal, and intradermal) for antibody generation. Both IgM and IgG generation can be tested. Following the results from the first animal studies, the purified retroviral vector can be examined in animals challenged with the real viruses. For example, hamsters which normally express ACE receptors can be challenged with COVID viruses and treated with the Omicron mutant retroviral vectors.

Experimental Methods

All transgenes were designed as described above and synthesized at Genscript. The sequences were confirmed by Sanger sequencing at Genscript. The plasmids expressing transgenes were digested with appropriate restriction enzymes and inserted into payload retroviral vector described herein (e.g., FIGS. 14A-14C). All final plasmids were sequenced at Primordium Labs (Arcadia, CA). Payload, wild-type gagpol or IDRV, and envelope were transiently transfected into 293T cells. A packaging 293T cell line platform expressing full-length amphotropic envelope with modifications and fully cloned (clone G8) and stably expressing wild-type gagpol was used to generate the full-length Spike manufacturing cell line. The cell line was further singly cloned. For Western blotting, A375 cells were transduced with retroviral vector at appropriate dilutions with 8 µg/mL polybrene for 3 days. The samples were run on 4-20% TGX (Bio-Rad) gel at 135V for 75 minutes. After transferred to a PVDF membrane (Thermo) and blocked with 3% BSA (Bovine Serum Albumin, Sigma) in 1×TBST (Tris-Buffered Saline, 0.1% Tween 20, Santa Cruz) for 1 hour at room temperature, the blot was incubated with anti-S2 antibody from R&D Systems (MAB1080100) at 0.5 mg/mL overnight at 4° C. Next day, after washed with 1×TBST three times, the blot was incubated with alkaline phosphatase-conjugated anti-rabbit antibody at 1:2000 dilution for 1 hour at room temperature and developed with NBT/BCIP substrate (Millipore) after another series of washes.

Example 3. Expression of Influenza Antigen

Figure 19:
FIG. 19 illustrates a diagram of a retroviral vector comprising a nucleic acid encoding with M2e and HA4900 (HA stalk with modifications) as an universal influenza vaccine.
Figure 20:
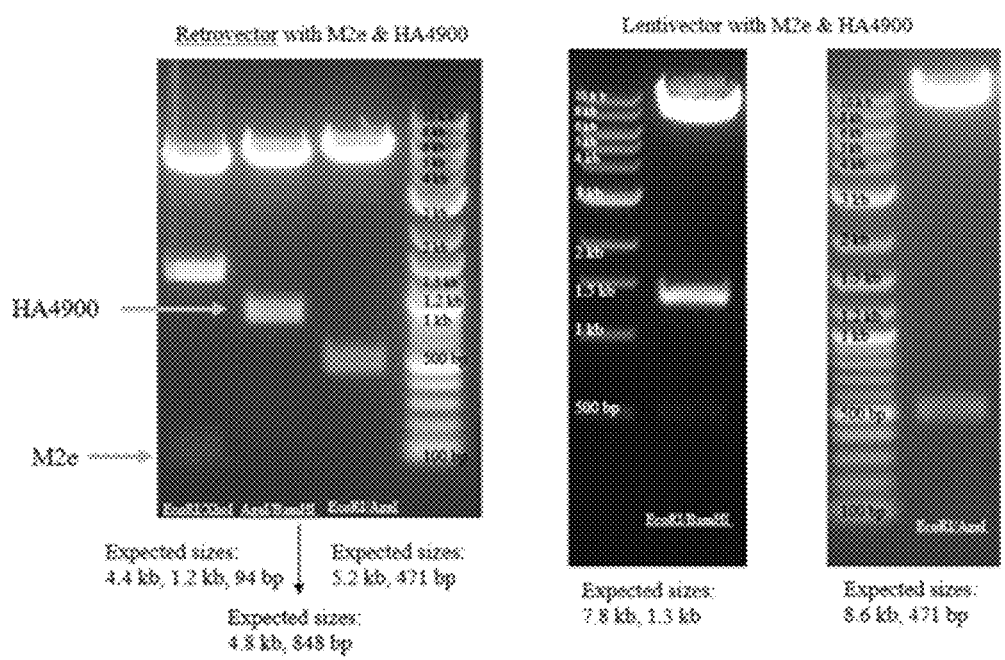
FIG. 20 illustrates presence of M2e and HA4900 (Influenza) transgene as a payload of a retroviral vector described herein or a lentivector.

FIG. 19 illustrates a retroviral vector describe herein comprising a payload for encoding M2e with Hemagglutinin (HA) Stalk (conserved region) domain with modifications. The nucleic acid sequence was codon optimized for human. Extracellular domain of the M2 protein (M2e) of influenza A has an amino acid sequence of: MSLLTEVET-PIRNEWGCRCNDSSD (SEQ ID NO: 14). Additional HA stalk with modifications included: head removal; glycine linker loop; intra-Cys bridge; transmembrane removal; loop fusion peptide; GCN4 position; and inter-Cys bridge. FIG. 20 illustrates presence of M2e and HA4900 (influenza) transgene as a payload of a retroviral vector described herein or a lentivector.

Figure 21A:
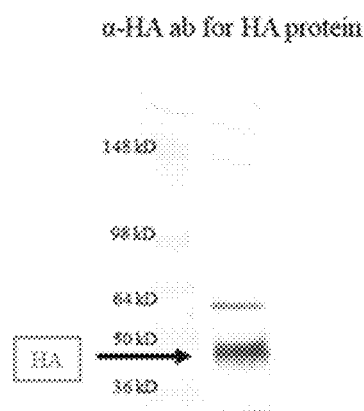
FIG. 21A illustrates expression of HA protein detected by Western blotting after testing cells were transduced with a retroviral vector described herein.
Figure 21B:
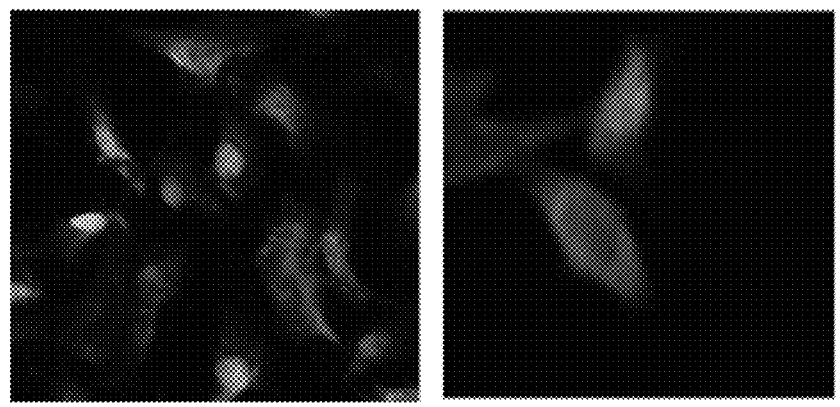
FIG. 21B illustrates expression of HA protein detected by immunocytochemistry (ICC) staining. Bright spots showed nuclear staining, and gray color showed the specific staining of HA protein.

The recombinant retroviral vector with a payload encoding M2e and HA4900 was produced by 293T transiently co-transfected with wtGP and amphotropic envelope, and vector titer was measured by RT-qPCR. The influenza antigen encoding retroviral vector exhibited 1.56E+08 vector genomes/mL. Influenza antigen vector particle titer measured by RT-qPCR produced from manufacturing clonal cell lines was measured in two exemplary clones to 1.94E+08 vector genomes/mL and 1.74E+07 vector genomes/mL. The manufacturing cell lines expressed IDRV2 and amphotropic envelope. When testing cells were transduced with such retroviral vector, the HA protein (Hemagglutinin) was detected in the cell lysates by Western Blotting (FIG. 21A). Immunocytochemistry staining for the HA protein demonstrated expression of HA protein and localization in the perinuclear region of testing cells (FIG. 21B).

While the foregoing disclosure has been described in some detail for purposes of clarity and understanding, it will be clear to one skilled in the art from a reading of this disclosure that various changes in form and detail can be made without departing from the true scope of the disclosure. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually and separately indicated to be incorporated by reference for all purposes.

| Exemplary amino acid sequence | |
|---|---|
| SEQ ID NO | amino acid sequence |
| 21 | MFVFLVLLPL VSSQCVNLTT RTQLPPAYTN SFTRGVYYPD KVFRSSVLHS TQDLFLPFFS NVTWFHAIHV SGTNGTKRFD NPVLPFNDGV YFASTEKSNI IRGWIFGTTL DSKTQSLLIV NNATNVVIKV CEFQFCNDPF LGVYYHKNNK SWMESEFRVY SSANNCTFEY VSQPFLMDLE GKQGNFKNLR EFVFKNIDGY FKIYSKHTPI NLVRDLPQGF SALEPLVDLP IGINITRFQT LLALHRSYLT PGDSSSGWTA GAAAYYVGYL QPRTFLLKYN ENGTITDAVD CALDPLSETK CTLKSFTVEK GIYQTSNFRV QPTESIVRFP NITNLCPFGE VFNATRFASV YAWNRKRISN CVADYSVLYN SASFSTFKCY GVSPTKLNDL CFTNVYADSF VIRGDEVRQI APGQTGKIAD YNYKLPDDFT GCVIAWNSNN LDSKVGGNYN YLYRLFRKSN LKPFERDIST EIYQAGSTPC NGVEGFNCYF PLQSYGFQPT NGVGYQPYRV VVLSFELLHA PATVCGPKKS TNLVKNKCVN FNFNGLTGTG VLTESNKKFL PFQQFGRDIA DTTDAVRDPQ TLEILDITPC SFGGVSVITP GTNTSNQVAV LYQDVNCTEV PVAIHADQLT PTWRVYSTGS NVFQTRAGCL IGAEHVNNSY ECDIPIGAGI CASYQTQTNS PRRARSVASQ SIIAYTMSLG AENSVAYSNN SIAIPTNFTI SVTTEILPVS MTKTSVDCTM YICGDSTECS NLLLQYGSFC TQLNRALTGI AVEQDKNTQE VFAQVKQIYK TPPIKDFGGF NFSQILPDPS KPSKRSFIED LLFNKVTLAD AGFIKQYGDC LGDIAARDLI CAQKENGLTV LPPLLTDEMI AQYTSALLAG TITSGWTFGA GAALQIPFAM QMAYRFNGIG VTQNVLYENQ KLIANQFNSA |

| Exemplary amino acid sequence | |
|---|---|
| SEQ ID NO | amino acid sequence |
| | IGKIQDSLSS TASALGKLQD VVNQNAQALN TLVKQLSSNF GAISSVLNDI LSRLDKVEAE VQIDRLITGR LQSLQTYVTQ QLIRAAEIRA SANLAATKMS ECVLGQSKRV DFCGKGYHLM SFPQSAPHGV VFLHVTYVPA QEKNFTTAPA ICHDGKAHFP REGVFVSNGT HWFVTQRNFY EPQIITTDNT FVSGNCDVVI GIVNNTVYDP LQPELDSFKE ELDKYFKNHT SPDVDLGDIS GINASVVNIQ KEIDRLNEVA KNLNESLIDL QELGKYEQYI KWPWYIWLGF IAGLIAIVMV TIMLCCMTSC CSCLKGCCSC GSCCKFDEDD SEPVLKGVKL HYT |
| 22 | MFVFLVLLPL VSSQCVNLIT RTQSYTNSFT RGVYYPDKVF RSSVLHSTQD LFLPFFSNVT WFHAIHVSGT NGTKRFDNPV LPFNDGVYFA STEKSNIIRG WIFGTTLDSK TQSLLIVNNA TNVVIKVCEF QFCNDPFLDV YYHKNNKSWM ESEFRVYSSA NNCTFEYVSQ PFLMDLEGKQ GNFKNLREFV FKNIDGYFKI YSKHTPINLG RDLPQGFSAL EPLVDLPIGI NITRFQTLLA LHRSYLTPGD SSSGWTAGAA AYYVGYLQPR TFLLKYNENG TITDAVDCAL DPLSETKCTL KSFTVEKGIY QTSNFRVQPT ESIVRFPNIT NLCPFDEVEN ATRFASVYAW NRKRISNCVA DYSVLYNFAP FFAFKCYGVS PTKLNDLCFT NVYADSFVIR GNEVSQIAPG QTGNIADYNY KLPDDFTGCV IAWNSNKLDS KVGGNYNYLY RLFRKSNLKP FERDISTEIY QAGNKPCNGV |

| Exemplary amino acid sequence | |
|---|---|
| SEQ ID NO | amino acid sequence |
| | AGFNCYFPLR SYGFRPTYGV GHQPYRVVVL SFELLHAPAT VCGPKKSTNL VKNKCVNFNF NGLTGTGVLT ESNKKFLPFQ QFGRDIADTT DAVRDPQTLE ILDITPCSFG GVSVITPGTN TSNQVAVLYQ GVNCTEVPVA IHADQLTPTW RVYSTGSNVF QTRAGCLIGA EYVNNSYECD IPIGAGICAS YQTQTKSHRR ARSVASQSII AYTMSLGAEN SVAYSNNSIA IPTNFTISVT TEILPVSMTK TSVDCTMYIC GDSTECSNLL LQYGSFCTQL KRALTGIAVE QDKNTQEVFA QVKQIYKTPP IKYFGGFNFS QILPDPSKPS KRSFIEDLLF NKVTLADAGF IKQYGDCLGD IAARDLICAQ KFNGLTVLPP LLTDEMIAQY TSALLAGTIT SGWTFGAGAA LQIPFAMQMA YRENGIGVTQ NVLYENQKLI ANQFNSAIGK IQDSLSSTAS ALGKLQDVVN HNAQALNTLV KQLSSKFGAI SSVLNDILSR LDKVEAEVQI DRLITGRLQS LQTYVTQQLI RAAEIRASAN LAATKMSECV LGQSKRVDFC GKGYHLMSFP QSAPHGVVFL HVTYVPAQEK NFTTAPAICH DGKAHFPREG VFVSNGTHWF VTQRNFYEPQ IITTDNTFVS GNCDVVIGIV NNTVYDPLQP ELDSFKEELD KYFKNHTSPD VDLGDISGIN ASVVNIQKEI DRLNEVAKNL NESLIDLQEL GKYEQYIKWP WYIWLGFIAG LIAIVMVTIM LCCMTSCCSC LKGCCSCGSC CKFDEDDSEP VLKGVKLHYT |

The invention claimed is:

1. A method of treating or preventing a disease or condition in a subject by administration of a recombinant retroviral vector with defective retroviral integration activity, comprising administering to the subject a recombinant retroviral vector comprising a first nucleic acid sequence encoding a mutant integrase and a second nucleic acid sequence encoding at least one payload comprising an antigen, said mutant integrase, when compared to a wild-type integrase having a sequence of SEQ ID NO: 1, comprises at least one mutation in a $Mg^{2+}$ binding motif of a catalytic core domain selected from the group consisting of D125A, D184A, and E220A; wherein the recombinant retroviral vector has defective retroviral integration activity as compared to a recombinant retroviral vector comprising the wild-type integrase, wherein the at least one payload is expressed in the subject for at least three days, wherein the recombinant retroviral vector is a recombinant murine leukemia virus (MLV), and wherein the antigen induces an immune response in the subject, thereby treating or preventing the disease or condition in the subject.

2. The method of claim 1, wherein the antigen comprises a pathogen polypeptide or fragment thereof or a cancer polypeptide or fragment thereof.

3. The method of claim 1, wherein the recombinant retroviral vector encodes at least one envelope protein.

4. The method of claim 3, wherein the at least one envelope protein comprises at least one alphavirus envelope protein.

5. The method of claim 4, wherein the at least one alphavirus envelope protein comprises at least one Sindbis virus envelope protein comprising E3 protein, E2 protein, 6K protein, E1 protein, or a combination thereof.

6. The method of claim 5, wherein the at least one Sindbis virus envelope protein comprises at least one mutation.

7. The method of claim 6, wherein the at least one mutation increases binding affinity between the at least one Sindbis virus envelope protein and a human cell.

8. The method of claim 7, wherein the human cell is a dendritic cell.

9. The method of claim 7, wherein the at least one mutation is E160G of the E2 protein of the Sindbis virus envelope protein when compared to a wild-type sequence.

10. The method of claim 1, wherein the recombinant retroviral vector comprises at least one modified untranslated region (UTR).

11. The method of claim 1, wherein the immune response comprises induction of neutralizing antibodies targeting the antigen, thereby generating immunity against the antigen in the subject.

12. The method of claim 1, wherein the immune response comprises induction of immunoglobulin antibodies targeting the antigen, thereby generating immunity against the antigen in the subject.

13. The method of claim 12, wherein the immunoglobulin antibodies comprise IgG antibodies, IgM antibodies, IgA antibodies, IgD antibodies, IgE antibodies, or a combination thereof.

14. The method of claim 13, wherein the immunoglobulin antibodies comprise IgG antibodies.

15. The method of claim 1, wherein the at least one payload is expressed in the subject for at least five days or at least nine days.

16. The method of claim 1, wherein the at least one payload is secreted in the subject for at least one day, at least three days, at least five days, or at least nine days.

17. The method of claim 15, wherein a duration of the immune response induced by the at least one payload is expressed for at least one day, at least three days, at least five days, or at least nine days is increased by at least 10%, at least 20%, at least 50%, at least 100%, at least 5-fold, at least 10-fold, or more compared to a duration of an immune response induced by a comparable payload that is expressed for fewer than one day, three days, five days, or nine days.

18. The method of claim 16, wherein a duration of the immune response induced by the at least one payload is secreted for at least one day, at least three days, at least five days, or at least nine days is increased by at least 10%, at least 20%, at least 50%, at least 100%, at least 5-fold, at least 10-fold, or more compared to a duration of an immune response induced by a comparable payload that is expressed for fewer than one day, three days, five days, or nine days.

19. The method of claim 1, wherein the immune response persists in the subject for at least three months, at least four months, at least five months, at least six months, or at least 12 months.

* * * * *

```
                         SEQUENCE LISTING

Sequence total quantity: 33
SEQ ID NO: 1               moltype = AA  length = 182
FEATURE                    Location/Qualifiers
source                     1..182
                           mol_type = protein
                           organism = Murine leukemia virus
SEQUENCE: 1
AVKQGTRVRG HRPGTHWEID FTEIKPGLYG YKYLLVFIDT FSGWIEAFPT KKETAKVVTK  60
KLLEEIFPRF GMPQVLGTDN GPAFVSKVSQ TVADLLGIDW KLHCAYRPQS SGQVERMNRT  120
IKETLTKLTL ATGSRDWVLL LPLALYRARN TPGPHGLTPY EILYGAPPPL VNFPDPDMTR  180
VT                                                                  182

SEQ ID NO: 2               moltype = AA  length = 182
FEATURE                    Location/Qualifiers
source                     1..182
                           mol_type = protein
                           organism = synthetic construct
SEQUENCE: 2
AVKQGTRVRG HRPGTHWEIA FTEIKPGLYG YKYLLVFIDT FSGWIEAFPT KKETAKVVTK  60
KLLEEIFPRF GMPQVLGTDN GPAFVSKVSQ TVADLLGIDW KLHCAYRPQS SGQVERMNRT  120
IKETLTKLTL ATGSRDWVLL LPLALYRARN TPGPHGLTPY EILYGAPPPL VNFPDPDMTR  180
VT                                                                  182

SEQ ID NO: 3               moltype = AA  length = 182
FEATURE                    Location/Qualifiers
source                     1..182
                           mol_type = protein
                           organism = synthetic construct
SEQUENCE: 3
AVKQGTRVRG HRPGTHWEID FTEIKPGLYG YKYLLVFIDT FSGWIEAFPT KKETAKVVTK  60
KLLEEIFPRF GMPQVLGTAN GPAFVSKVSQ TVADLLGIDW KLHCAYRPQS SGQVERMNRT  120
IKETLTKLTL ATGSRDWVLL LPLALYRARN TPGPHGLTPY EILYGAPPPL VNFPDPDMTR  180
VT                                                                  182

SEQ ID NO: 4               moltype = AA  length = 182
FEATURE                    Location/Qualifiers
source                     1..182
                           mol_type = protein
                           organism = synthetic construct
```

-continued

```
SEQUENCE: 4
AVKQGTRVRG HRPGTHWEID FTEIKPGLYG YKYLLVFIDT FSGWIEAFPT KKETAKVVTK   60
KLLEEIFPRF GMPQVLGTDN GPAFVSKVSQ TVADLLGIDW KLHCAYRPQS SGQVARMNRT  120
IKETLTKLTL ATGSRDWVLL LPLALYRARN TPGPHGLTPY EILYGAPPPL VNFPDPDMTR  180
VT                                                                182

SEQ ID NO: 5            moltype = AA   length = 182
FEATURE                 Location/Qualifiers
source                  1..182
                        mol_type = protein
                        organism = synthetic construct
SEQUENCE: 5
AVKQGTRVRG HRPGTHWEIA FTEIKPGLYG YKYLLVFIDT FSGWIEAFPT KKETAKVVTK   60
KLLEEIFPRF GMPQVLGTAN GPAFVSKVSQ TVADLLGIDW KLHCAYRPQS SGQVERMNRT  120
IKETLTKLTL ATGSRDWVLL LPLALYRARN TPGPHGLTPY EILYGAPPPL VNFPDPDMTR  180
VT                                                                182

SEQ ID NO: 6            moltype = AA   length = 182
FEATURE                 Location/Qualifiers
source                  1..182
                        mol_type = protein
                        organism = synthetic construct
SEQUENCE: 6
AVKQGTRVRG HRPGTHWEIA FTEIKPGLYG YKYLLVFIDT FSGWIEAFPT KKETAKVVTK   60
KLLEEIFPRF GMPQVLGTDN GPAFVSKVSQ TVADLLGIDW KLHCAYRPQS SGQVARMNRT  120
IKETLTKLTL ATGSRDWVLL LPLALYRARN TPGPHGLTPY EILYGAPPPL VNFPDPDMTR  180
VT                                                                182

SEQ ID NO: 7            moltype = AA   length = 182
FEATURE                 Location/Qualifiers
source                  1..182
                        mol_type = protein
                        organism = synthetic construct
SEQUENCE: 7
AVKQGTRVRG HRPGTHWEID FTEIKPGLYG YKYLLVFIDT FSGWIEAFPT KKETAKVVTK   60
KLLEEIFPRF GMPQVLGTAN GPAFVSKVSQ TVADLLGIDW KLHCAYRPQS SGQVARMNRT  120
IKETLTKLTL ATGSRDWVLL LPLALYRARN TPGPHGLTPY EILYGAPPPL VNFPDPDMTR  180
VT                                                                182

SEQ ID NO: 8            moltype = AA   length = 182
FEATURE                 Location/Qualifiers
source                  1..182
                        mol_type = protein
                        organism = synthetic construct
SEQUENCE: 8
AVKQGTRVRG HRPGTHWEIA FTEIKPGLYG YKYLLVFIDT FSGWIEAFPT KKETAKVVTK   60
KLLEEIFPRF GMPQVLGTAN GPAFVSKVSQ TVADLLGIDW KLHCAYRPQS SGQVARMNRT  120
IKETLTKLTL ATGSRDWVLL LPLALYRARN TPGPHGLTPY EILYGAPPPL VNFPDPDMTR  180
VT                                                                182

SEQ ID NO: 9            moltype =     length =
SEQUENCE: 9
000

SEQ ID NO: 10           moltype =     length =
SEQUENCE: 10
000

SEQ ID NO: 11           moltype = AA   length = 320
FEATURE                 Location/Qualifiers
source                  1..320
                        mol_type = protein
                        organism = Human alphaherpesvirus 1
SEQUENCE: 11
MASYPGHQHA SAFDQAARSR GHSNRRTALR PRRQQEATEV RPEQKMPTLL RVYIDGPHGM   60
GKTTTTQLLV ALGSRDDIVY VPEPMTYWRV LGASETIANI YTTQHRLDQG EISAGDAAVV  120
MTSAQITMGM PYAVTDAVLA PHIGGEAGSS HAPPPALTLI FDRHPIAALL CYPAARYLMG  180
SMTPQAVLAF VALIPPTLPG TNIVLGALPE DRHIDRLAKR QRPGERLDLA MLAAIRRVYG  240
LLANTVRYLQ CGGSWREDWG QLSGTAVPPQ GAEPQSNAGP RPHIGDTLFT LFRAPELLAP  300
NGDLYNVFAW ALDVLAKRLR                                             320

SEQ ID NO: 12           moltype = AA   length = 12
FEATURE                 Location/Qualifiers
source                  1..12
                        mol_type = protein
                        organism = synthetic construct
SEQUENCE: 12
LQKKLEELEL DG                                                      12
```

```
SEQ ID NO: 13            moltype = AA  length = 32
FEATURE                  Location/Qualifiers
source                   1..32
                         mol_type = protein
                         organism = synthetic construct
SEQUENCE: 13
MDAMKRGLCC VLLLCGAVFV SASQEIHARF RR                                       32

SEQ ID NO: 14            moltype = AA  length = 24
FEATURE                  Location/Qualifiers
source                   1..24
                         mol_type = protein
                         organism = Influenza A virus
SEQUENCE: 14
MSLLTEVETP IRNEWGCRCN DSSD                                                24

SEQ ID NO: 15            moltype =     length =
SEQUENCE: 15
000

SEQ ID NO: 16            moltype =     length =
SEQUENCE: 16
000

SEQ ID NO: 17            moltype =     length =
SEQUENCE: 17
000

SEQ ID NO: 18            moltype =     length =
SEQUENCE: 18
000

SEQ ID NO: 19            moltype =     length =
SEQUENCE: 19
000

SEQ ID NO: 20            moltype =     length =
SEQUENCE: 20
000

SEQ ID NO: 21            moltype = AA  length = 1273
FEATURE                  Location/Qualifiers
source                   1..1273
                         mol_type = protein
                         organism = Severe acute respiratory syndrome coronavirus 2
SEQUENCE: 21
MFVFLVLLPL VSSQCVNLTT RTQLPPAYTN SFTRGVYYPD KVFRSSVLHS TQDLFLPFFS          60
NVTWFHAIHV SGTNGTKRFD NPVLPFNDGV YFASTEKSNI IRGWIFGTTL DSKTQSLLIV         120
NNATNVVIKV CEFQFCNDPF LGVYYHKNNK SWMESEFRVY SSANNCTFEY VSQPFLMDLE         180
GKQGNFKNLR EFVFKNIDGY FKIYSKHTPI NLVRDLPQGF SALEPLVDLP IGINITRFQT         240
LLALHRSYLT PGDSSSGWTA GAAAYYVGYL QPRTFLLKYN ENGTITDAVD CALDPLSETK         300
CTLKSFTVEK GIYQTSNFRV QPTESIVRFP NITNLCPFGE VFNATRFASV YAWNRKRISN         360
CVADYSVLYN SASFSTFKCY GVSPTKLNDL CFTNVYADSF VIRGDEVRQI APGQTGKIAD         420
YNYKLPDDFT GCVIAWNSNN LDSKVGGNYN YLYRLFRKSN LKPFERDIST EIYQAGSTPC         480
NGVEGFNCYF PLQSYGFQPT NGVGYQPYRV VVLSFELLHA PATVCGPKKS TNLVKNKCVN         540
FNFNGLTGTG VLTESNKKFL PFQQFGRDIA DTTDAVRDPQ TLEILDITPC SFGGVSVITP         600
GTNTSNQVAV LYQDVNCTEV PVAIHADQLT PTWRVYSTGS NVFQTRAGCL IGAEHVNNSY         660
ECDIPIGAGI CASYQTQTNS PRRARSVASQ SIIAYTMSLG AENSVAYSNN SIAIPTNFTI         720
SVTTEILPVS MTKTSVDCTM YICGDSTECS NLLLQYGSFC TQLNRALTGI AVEQDKNTQE         780
VFAQVKQIYK TPPIKDFGGF NFSQILPDPS KPSKRSFIED LLFNKVTLAD AGFIKQYGDC         840
LGDIAARDLI CAQKFNGLTV LPPLLTDEMI AQYTSALLAG TITSGWTFGA GAALQIPFAM         900
QMAYRFNGIG VTQNVLYENQ KLIANQFNSA IGKIQDSLSS TASALGKLQD VVNQNAQALN         960
TLVKQLSSNF GAISSVLNDI LSRLDKVEAE VQIDRLITGR LQSLQTYVTQ QLIRAAEIRA        1020
SANLAATKMS ECVLGQSKRV DFCGKGYHLM SFPQSAPHGV VFLHVTYVPA QEKNFTTAPA        1080
ICHDGKAHFP REGVFVSNGT HWFVTQRNFY EPQIITTDNT FVSGNCDVVI GIVNNTVYDP        1140
LQPELDSFKE ELDKYFKNHT SPDVDLGDIS GINASVVNIQ KEIDRLNEVA KNLNESLIDL        1200
QELGKYEQYI KWPWYIWLGF IAGLIAIVMV TIMLCCMTSC CSCLKGCCSC GSCCKFDEDD        1260
SEPVLKGVKL HYT                                                          1273

SEQ ID NO: 22            moltype = AA  length = 1270
FEATURE                  Location/Qualifiers
source                   1..1270
                         mol_type = protein
                         organism = Severe acute respiratory syndrome coronavirus 2
SEQUENCE: 22
MFVFLVLLPL VSSQCVNLIT RTQSYTNSFT RGVYYPDKVF RSSVLHSTQD LFLPFFSNVT          60
WFHAIHVSGT NGTKRFDNPV LPFNDGVYFA STEKSNIIRG WIFGTTLDSK TQSLLIVNNA         120
TNVVIKVCEF QFCNDPFLDV YYHKNNKSWM ESEFRVYSSA NNCTFEYVSQ PPLMDLEGKQ         180
GNFKNLREFV FKNIDGYFKI YSKHTPINLG RDLPQGFSAL EPLVDLPIGI NITRFQTLLA         240
```

```
LHRSYLTPGD SSSGWTAGAA AYYVGYLQPR TFLLKYNENG TITDAVDCAL DPLSETKCTL  300
KSFTVEKGIY QTSNFRVQPT ESIVRFPNIT NLCPFDEVFN ATRFASVYAW NRKRISNCVA  360
DYSVLYNFAP FFAFKCYGVS PTKLNDLCFT NVYADSFVIR GNEVSQIAPG QTGNIADYNY  420
KLPDDFTGCV IAWNSNKLDS KVGGNYNYLY RLFRKSNLKP FERDISTEIY QAGNKPCNGV  480
AGFNCYFPLR SYGFRPTYGV GHQPYRVVVL SFELLHAPAT VCGPKKSTNL VKNKCVNFNF  540
NGLTGTGVLT ESNKKFLPFQ QFGRDIADTT DAVRDPQTLE ILDITPCSFG GVSVITPGTN  600
TSNQVAVLYQ GVNCTEVPVA IHADQLTPTW RVYSTGSNVF QTRAGCLIGA EYVNNSYECD  660
IPIGAGICAS YQTQTKSHRR ARSVASQSII AYTMSLGAEN SVAYSNNSIA IPTNFTISVT  720
TEILPVSMTK TSVDCTMYIC GDSTECSNLL LQYGSFCTQL KRALTGIAVE QDKNTQEVFA  780
QVKQIYKTPP IKYFGGFNFS QILPDPSKPS KRSFIEDLLF NKVTLADAGF IKQYGDCLGD  840
IAARDLICAQ KFNGLTVLPP LLTDEMIAQY TSALLAGTIT SGWTFGAGAA LQIPFAMQMA  900
YRFNGIGVTQ NVLYENQKLI ANQFNSAIGK IQDSLSSTAS ALGKLQDVVN HNAQALNTLV  960
KQLSSKFGAI SSVLNDILSR LDKVEAEVQI DRLITGRLQS LQTYVTQQLI RAAEIRASAN 1020
LAATKMSECV LGQSKRVDFC GKGYHLMSFP QSAPHGVVFL HVTYVPAQEK NFTTAPAICH 1080
DGKAHFPREG VFVSNGTHWF VTQRNFYEPQ IITTDNTFVS GNCDVVIGIV NNTVYDPLQP 1140
ELDSFKEELD KYFKNHTSPD VDLGDISGIN ASVVNIQKEI DRLNEVAKNL NESLIDLQEL 1200
GKYEQYIKWP WYIWLGFIAG LIAIVMVTIM LCCMTSCCSC LKGCCSCGSC CKFDEDDSEP 1260
VLKGVKLHYT                                                       1270

SEQ ID NO: 23         moltype = AA  length = 4
FEATURE               Location/Qualifiers
source                1..4
                      mol_type = protein
                      organism = Severe acute respiratory syndrome coronavirus 2
SEQUENCE: 23
RRAR                                                                4

SEQ ID NO: 24         moltype = AA  length = 4
FEATURE               Location/Qualifiers
source                1..4
                      mol_type = protein
                      organism = synthetic construct
SEQUENCE: 24
SRAG                                                                4

SEQ ID NO: 25         moltype = DNA  length = 100
FEATURE               Location/Qualifiers
source                1..100
                      mol_type = genomic DNA
                      organism = Murine leukemia virus
SEQUENCE: 25
actagaggag atcttcccca ggttcggcat gcctcaggta ttgggaactg acaatgggcc   60
tgccttcgtc tccaaggtga gtcagacagt ggccgatctg                       100

SEQ ID NO: 26         moltype = DNA  length = 100
FEATURE               Location/Qualifiers
source                1..100
                      mol_type = other DNA
                      organism = synthetic construct
SEQUENCE: 26
actagaggag atcttcccca ggttcggcat gcctcaggta ttgggaactg ccaatgggcc   60
tgccttcgtc tccaaggtga gtcagacagt ggccgatctg                       100

SEQ ID NO: 27         moltype = DNA  length = 100
FEATURE               Location/Qualifiers
source                1..100
                      mol_type = genomic DNA
                      organism = Murine leukemia virus
SEQUENCE: 27
cagggaacta gggtccgcgg gcatcggccc ggcactcatt gggagatcga tttcaccgag   60
ataaagcccg gattgtatgg ctataaatat cttctagttt                       100

SEQ ID NO: 28         moltype = DNA  length = 100
FEATURE               Location/Qualifiers
source                1..100
                      mol_type = other DNA
                      organism = synthetic construct
SEQUENCE: 28
cagggaacta gggtccgcgg gcatcggccc ggcactcatt gggagatcgc cttcaccgag   60
ataaagcccg gattgtatgg ctataaatat cttctagttt                       100

SEQ ID NO: 29         moltype = DNA  length = 95
FEATURE               Location/Qualifiers
source                1..95
                      mol_type = other DNA
                      organism = synthetic construct
SEQUENCE: 29
cagggaacta gggtccgcgg gcatcggccc ggcactcatg atcgccttca ccgagataaa   60
gcccggattg tatggctata aatatcttct agttt                             95
```

```
SEQ ID NO: 30          moltype = DNA  length = 97
FEATURE                Location/Qualifiers
source                 1..97
                       mol_type = other DNA
                       organism = synthetic construct
SEQUENCE: 30
cagggaacta gggtccgcgg gcatcggccc ggcacttggg agatcgcctt caccgagata   60
aagcccggat tgtatggcta taaatatctt ctagttt                            97

SEQ ID NO: 31          moltype = DNA  length = 100
FEATURE                Location/Qualifiers
source                 1..100
                       mol_type = genomic DNA
                       organism = Murine leukemia virus
SEQUENCE: 31
gtcagacagt ggccgatctg ttggggattg attggaaatt acattgtgca tacagacccc   60
aaagctcagg ccaggtagaa agaatgaata gaaccatcaa                         100

SEQ ID NO: 32          moltype = DNA  length = 99
FEATURE                Location/Qualifiers
source                 1..99
                       mol_type = other DNA
                       organism = synthetic construct
SEQUENCE: 32
gtcagacagt ggccgatctg ttggggattg attggaaatt acattgtgca tacagacccc   60
aaagctcggc caggtagcca gaatgaatag aaccatcaa                          99

SEQ ID NO: 33          moltype = DNA  length = 100
FEATURE                Location/Qualifiers
source                 1..100
                       mol_type = other DNA
                       organism = synthetic construct
SEQUENCE: 33
gtcagacagt ggccgatctg ttggggattg attggaaatt acattgtgca tacagacccc   60
aaagctcagg ccaggtagcc agaatgaata gaaccatcaa                         100
```